Figure 1:
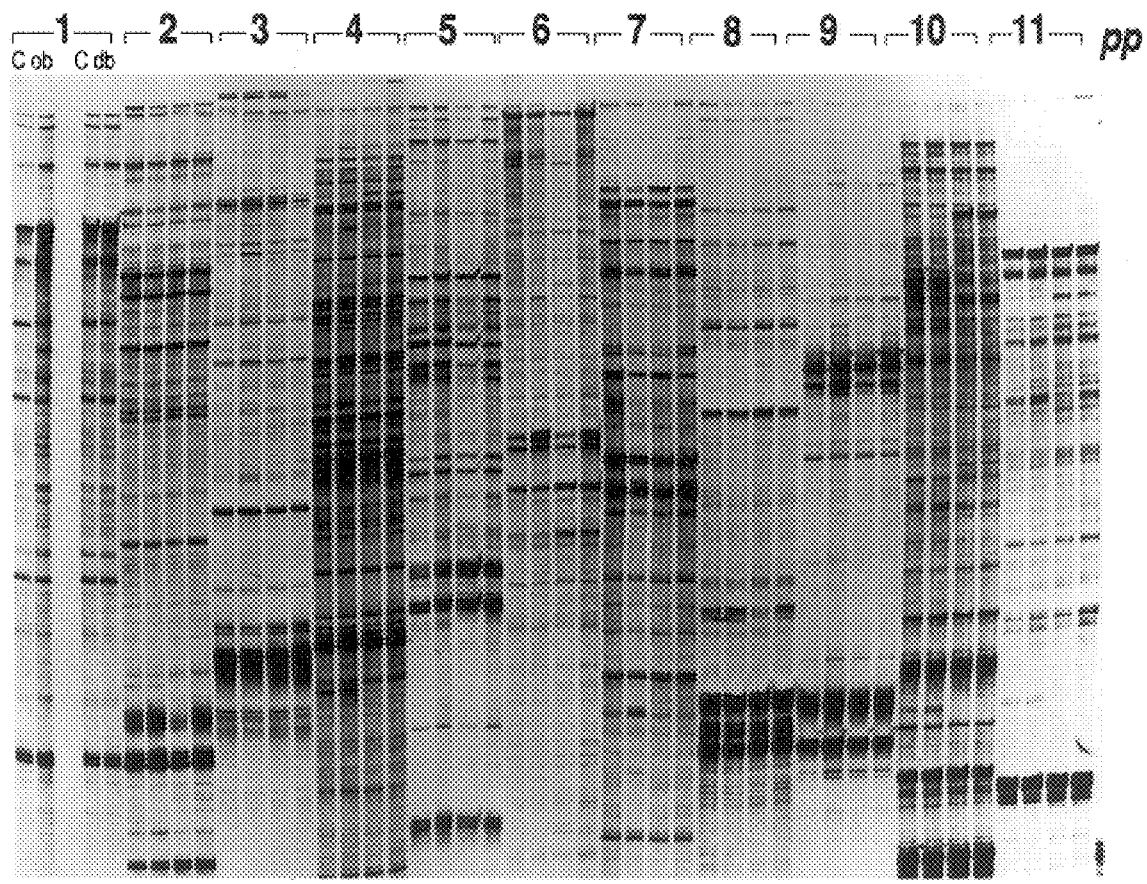

United States Patent [19]
Tartaglia

[11] Patent Number: 6,057,109
[45] Date of Patent: May 2, 2000

[54] COMPOSITIONS FOR THE TREATMENT OF BODY WEIGHT DISORDERS INCLUDING OBESITY

[75] Inventor: Louis Anthony Tartaglia, Watertown, Mass.

[73] Assignee: Millennium Pharmaceuticals, Inc., Cambridge, Mass.

[21] Appl. No.: 09/210,681

[22] Filed: Dec. 14, 1998

Related U.S. Application Data

[62] Division of application No. 08/946,719, Oct. 8, 1997, which is a division of application No. 08/807,861, Feb. 26, 1997, Pat. No. 5,853,975, which is a continuation-in-part of application No. 08/518,878, Aug. 23, 1995, Pat. No. 5,702,902, which is a continuation-in-part of application No. 08/470,868, Jun. 6, 1995, Pat. No. 5,861,485, which is a continuation-in-part of application No. 08/294,522, Aug. 23, 1994, Pat. No. 5,741,666.

[51] Int. Cl.⁷ ..................................................... C12Q 1/68
[52] U.S. Cl. ................................ 435/6; 530/350; 530/351
[58] Field of Search ................................. 435/6; 530/350, 530/351

[56] References Cited

U.S. PATENT DOCUMENTS

| | | | |
|---|---|---|---|
| 4,190,496 | 2/1980 | Rubenstein | 435/7.9 |
| 5,093,246 | 3/1992 | Cech et al. | 435/6 |

FOREIGN PATENT DOCUMENTS

| | | |
|---|---|---|
| WO 88/04300 | 6/1988 | WIPO . |
| WO90/11364 | 10/1990 | WIPO . |

OTHER PUBLICATIONS

Astrup A. et al., 1989, "Epinephrine mediates facultative carbohydrate–induced thermogenesis in human skeletal muscle", Am. J. Physiol. 257:E340–E345.
Been and Cech, 1986, "One binding site determines sequence specificity of Tetrahymena pre–rRNA self–splicing, trans–splicing, and RNA enzyme activity", Cell, 47:207–216.
Bhandari et al., 1991, "A functional promoter flanks an intronless glutamine synthetase gene", J. Biol. Chem. 266:7784–7792.
Bibb et al., 1981, "Sequence and gene organization of mouse mitochondrial DNA", Cell 26:167–180.
Block BA., 1994, "Thermogenesis in muscle", Ann. Rev. Physiol. 56:535–577.
Borjeson, M., 1976, "The aetiology of obesity in children. A study of 101 twin pairs", Acta. Paediatr. Scand. 65:279–287.
Bouillaud F. et al., 1994, "A sequence related to a DNA recognition element is essential for the inhibition by nucleotides of proton transport through the mitochondrial uncoupling protein", EMBO J. 13:1990–1997.
Cannon & Nedergaard, 1985, "The biochemistry of an inefficient tissue: brown adipose tissue", Essays in Biochem. 20:110–165.
Cassard AM. et al., 1990, "Human uncoupling protein gene: structure, comparison with rat gene, and assignment to the long arm of chromosome 4", J. Cell Biochem. 43:255–64.

Coleman, D.L., and Eicher, E.M., 1990, "Fat (fat) and tubby (tub): two autosomal recessive mutations causing obesity syndromes in the mouse", J. Heredity 81:424–427.
Coleman, D.L., 1978, "Obese and diabetes: two mutant genes causing diabetes–obesity syndromes in mice", Diabetologia 14:141–148.
Cummings D.E. et al., 1996, "Genetically lean mice result from targeted disruption of the RII beta subunit of protein kinase A", Nature 382:622–626.
Cunningham S. et al., 1985, "The characterization and energetic potential of brown adipose tissue in man", Clin. Sci. 69:343–348.
Davis T.R.A., 1963, "Contribution of skeletal muscle to non–shivering thermogenesis in the dog", Am. J. Physiol. 213:1423–1426.
Duchamp C. et al., 1993, "Skeletal muscle as the major site of non–shivering thermogenesis in cold–acclimated ducklings", Am. J. Physiol. 265:R1076–R1083.
Esner, M., 1979, "The role of insulin in the regulation of stearic acid desaturase activity in liver and adipose tissue from obese–hyperglycemic (ob/ob) and lean mice", Biochem. J. 180:551–558.
Flier et al., 1987, "Severely impaired adipslin expression in genetic and acquired obesity", Science 237:405–408.
Flower, D.R. et al., 1991, "Mouse oncogene protein 24p3 is a member of the lipocalin protein family", Biochem. Biophys. Res. Comm. 180:69–74.
Forman et al., 1994, "Cross–talk amoung RORα1 and the rev–erb family of orphan nuclear receptors", Mol. Endocrinol. 8:1253–1261.
Friedman, J.M. et al., 1991, "Molecular mapping of obesity genes", Mammalian Gene 1:130–144.
Genbank Accession No. L00993, 1993.
Genbank Accession No. P16036, 1996.
Genbank Accession No. P12242, 1997.

(List continued on next page.)

*Primary Examiner*—Remy Yucel
*Attorney, Agent, or Firm*—Pennie & Edmonds LLP

[57] ABSTRACT

The present invention relates to methods and compositions for the treatment of body weight disorders, including, but not limited to, obesity. Specifically, the present invention identifies and describes genes which are differentially expressed in body weight disorder states, relative to their expression in normal, or non-body weight disorder states, and/or in response to manipulations relevant to appetite and/or weight regulation. Further, the present invention identifies and describes genes via the ability of their gene products to interact with gene products involved in body weight disorders and/or appetite and/or body weight regulation. Still further, the present invention provides methods for the identification and therapeutic use of compounds as treatments of body weight disorders. Additionally, the present invention describes methods for the diagnostic evaluation and prognosis of various body weight disorders, and for the identification of subjects exhibiting a predisposition to such conditions.

4 Claims, 25 Drawing Sheets

OTHER PUBLICATIONS

Gonzalez–Barioso MM. et al., 1996, "Activation of the uncoupling protein by fatty acids is modulated by mutations in the C–terminal region of the protein", Eur. J. Biochem. 239:445–450.

Hamann et al., 1996, "Decreased brown fat markedly enhances susceptibility to diet induced obesity, diabetes, and hyperlipidemia", Endocrinol. 137:21–29.

Haseloff and Gerlach, 1988, "Simple RNA enzymes with new and highly specific endoribonuclease", Nature, 334:585–591.

Herberg, L. and Coleman, D.L., 1977, "Laboratory animals exhibiting obesity and diabetes syndromes", Metabolism 26:59–99.

Himms–Hagen J., 1989, "Brown adipose tissue thermogenesis and obesity", Prog. Lipid Res. 28:67–115.

Hou, J. et al., 1994, "Molecular cloning and expression of the gene for a major leucine–rich protein from human hepatoblastoma cells (HEPG2)", In Vitro Cell. Dev. Biol. Anim. 30A:111–114.

Houghten, R. et al., 1991, "Generation and use of synthetic peptide combinatorial libraries for basic research and drug discovery", Nature 354:84–86.

Hraba–Renevey, S. et al., 1989, "SV40 induced expression of mouse gene 24p3 involves a posttranscritional mechanism", Oncogene 4:601–608.

Huttunen P. et al., 1981, "The occurrence of brown adipose tissue in outdoor workers", Eur. J. Appl. Physiol. 46:339–345.

Jensen M.D. et al., 1995, "Thermogenesis after a mixed meal: role of leg and splanchnic tissues in men and women", Am. J. Physiol. 268:E433–438.

Kaestner, K.H. et al., 1989, "Differentiation–induced gene expression in 3T3–L1 preadipocytes", J. Biol. Chem. 264:14755–14761.

Klaus S. et al., 1991, "The uncoupling protein UCP: a membraneous mitochondrial ion carrier exclusively expressed in brown adipose tissue", Int. J. Biochem. 23:791–801.

Klingenberg M., 1990, "Mechanism and evolution of uncoupling protein of brown adipose tissue", Trends Biochem. Sci. 15:108–112.

Kopecky J. et al., 1995, "Expression of the mitochondrial uncoupling protein gene from the aP2 gene promoter prevents genetic obesity", J. Clin. Invest. 96:2914–2923.

Kouba, M. et al., 1993, "Liver stearyl–coA desaturase activity and fatness in birds. In vitro studies in the growing turkey and chicken", Comp. Biochem. Physiol. 105A:359–362.

Kuan & Saler, 1993, "The mitochondrial carrier family of transport proteins: structural, functional, evolutionary relationships", Crit. Rev. Biochem. Mol. Biol. 18:209–233, 1993.

Lam et al., 1991, "A new type of synthetic peptide library for identifying ligand binding activity", Nature 354:82–84.

Legrand, P. et al., 1987, "Hepatic lipogenesis in genetically lean and fat chickens in vitro studies", Comp. Biochem. Physiol. 87B:789–792.

Lowell, 1990, "Reduced adipsin expression in urine obesity: effect of age and treatment with the sympathomimetic–thermogenic drug mixture ephedrine and caffeine", Endocrinology 126:1514–1520.

Lowell B.B. et al., 1993, "Development of obesity in transgenic mice after genetic ablation of brown adipose tissue", Nature 366:740–742.

Matsunaga, E. et al., 1990, "The rat P450 IID subfamily: complete sequences of four closely linked genes and evidence that gene conversions maintained sequence homogeneity at the heme–binding region of the cytochrome P450", J. Mol. Evol. 30:155–169.

McFarlane–Anderson, 1992, "Levels of G–proteins in liver and brain of lean and obese (ob/ob) mice", Biochem. J. 282:15–23.

Moll et al. 1991, "The genetic and environmental sources of body mass index variability: the muscatine ponderosity family study", Am. J. Hum. Gen. 49:1243–1255.

Murdza–Inglis, D.L. et al., 1994, "A single mutation in uncoupling protein of rat brown adipose tissue mitochondria abolishes GDP sensitivity $H^+$ transport", J. Biol. Chem. 269:7435–7438.

Murdza–Inglis, D.L. et al., 1991, "Functional reconstitution of rat uncoulpling protein following its high level expression in yeast", J. Biol. Chem. 260:11871–11875.

Myers & Miller, 1988, "Optimal alignments in liner space", CABIOS 4:11–17.

Nicholls & Locke, 1984, "Thermogenic mechanisms in brown fat", Physiol. Rev. 64:1–64.

Ntambi, J.M. et al., 1988, "Differentiation–induced gene expression in 3T3–L1 preadipocytes", J. Biol. Chem. 263:17291–17300.

Ntambi, J.M., 1992, "Dietary regulation of Stearoyl–CoA desaturase 1 gene expression in mouse liver", J. Biol. Chem. 267:10925–10930.

Ohneda, 1993, "Glut2 expression and function in $\beta$–cells of GK rats with NIDDM", Diabetes 42:1065–1072.

Platt, 1989, "Obesity–linked regulation of the adipsin gene promoter in transgenic mice",Proc. Natl. Acad. Sci. USA 86:7490–7494.

Pon & Schatz, "Biogenesis of yeast mitochondria" in The Molecular and Cellular Biology of the Yeast Saccharomyces, vol. 1, Broach J.R. et al., eds., Cold Spring Harbor Laboratory Press, Cold Spring Harbor, New York, 1991.

Pringle. et al., 1989, "Fluorescence microscopy methods for yeast", Methods Cell Biol. 31:357–435.

Rossi, J., 1994, "Making ribozymes work in cells", Current Biology 4:469–471.

Rothwell & Stock, 1986, "Brown adipose tissue and diet–induced thermogenesis", In Brown Adipose Tissue. Trayhurn P., Nicholls D.G., Eds., London, Arnold, p. 269–298.

Rothwell & Stock, 1981, "Regulation of energy balance", Annu. Rev. Nutr. 1:235–56.

Santos G.C. et al., 1992, "Accumulation of brown adipose tissue and nutritional status", Arch. Pathol. Lab Med. 116:1152–1154.

Sarver et al., 1990, "Ribozymes as potential anti–HIV–1 therapeutic agents", Science 247:1222–1225.

Schibler et al., 1982, "The mouse $\alpha$–amylase multigene family", J. Mol. Biol. 155:247–266.

Schibler, U. et al., 1986, "Structural arrangement and tissue–specific expression of the two murine alpha–amylase loci amy–1 & amy–2", in "Oxford Surveys on Eukaryotic Genes", Maclean, N., ed. 3:210, Oxford Univ. Press, New York.

Schulz L., 1987, "Brown adipose tissue: regulation of thermogenesis and implications for obesity", J. Am. Diet Assoc. 87:761–764.

Segal K.R. et al., 1992, "Independent effects of obesity and insulin resistance of postprandial thermogenesis in men",J. Clin. Invest. 89:824–833.

Shahan, K. et al., 1987, "Nucleotide sequences of liver, lachrymal, submaxillar gland mouse major urinary protein mRNAs: mosaic structure and construction of panels of gene–specific synthetic oligoncleotide probes", Mol. Cell. Biol. 1:1938–1946.

Simonsen J. et al., 1993, "Contribution of skeletal muscle and adipose tissue to adrenaline–induced thermogenesis in man", Int. J. Obes. Relat. Metab. Disord. 17(Suppl. 3):S47–S51.

Simonsen L. et al., 1992, "Thermogenic response to epinephrine in the forearm and abdominal subcutaneous adipose tissue", Am. J. Physiol. 263:E850–E855.

Simopoulos, A.P. & Childs B., eds., 1989, "Genetic variation and nutrition in obesity: approaches to the molecular genetics of obesity", in "Genetic Variation and Nutrition in Obesity", World Review of Nutrition and Diabetes 63, S. Karger, Basel, Switzerland.

Songyang, Z. et al., 1993, "SH2 domains recognize specific phosphopeptide sequences", Cell 72:767–778.

Spiegelman & Flier, 1996, "Adipogenesis and obesity: rounding out the big picture", Cell 87:377–389.

Squires E.J. and Negism M., 1988, "Reciprocal regulation of sex–dependent expression of testerone 15α–hydroxylase (P–450$_{15\alpha}$) in liver and kidney of male mice by androgen", J. Biol. Chem. 263:4166–4171.

Stunkard, 1990, "The body–mass index of twins who have been reared apart", N. Eng. J. Med. 322:1483.

Terazono, K. et al., 1988, "A novel gene activated in regenerating islets", J. Biol. Chem. 263:2111–2114.

Unno, M. et al., 1987, "Structure, chromosomal localisation, and expression of mouse reg genes, reg I and reg II", J. Biol. Chem. 268:15974–15982.

Wahle, K.W.J. and Radcliffe, J.D., 1977, "Effect of a diet rich in sunflower oil on aspects of lipid metabolism in the genetically–obese rat", Lipids 12:135–139.

Walker & Runswick, 1993, "The mitochondrial transport protein superfamily", J. Bioenergetics Biomembranes 25:435–446.

Watanabe, T., 1990, "Complete nucleotide sequence of human reg gene and its expression in normal and tumoral tissues", J. Biol. Chem. 265:7432–7439.

West, D.B. et al., 1992, "Dietary obesity in nine inbred mouse strains", Am. J. Physiol. 262:R1025–R1032.

Wilding, 1993, "Increased neuropeptide–Y messenger ribonucleic acid (mRNA) and decreased neurotnsin mRNA in the hypothalamus of the obese (ob/ob) mouse", Endocrinology 132:1939–1944.

Yamasaki, N. et al., 1987, "Sequence analysis of a cDNA clone of a gene encoding a component of a putative phophorylcholine–specific T suppressor factor and functional property of its gene product", Eur. J. Immunol. 17:247–253.

Zaug, et al., 1984, "A labile phosphodiester bond at the ligation junction in a circular intervening sequence RNA", Science, 224:574–578.

Zaug, et al., 1986, "The tetrahymena ribozyme acts like an RNA restriction endonuclease", Nature, 324:429–433.

Zaug and Cech, 1986, "The intervening sequence RNA of tetrahymena is an enzyme", Science, 231:470–475.

```
         10        20        30        40
    ....|....|....|....|....|....|....|....|
    GGGCAGTACAACCAGATCCACTTTTATTAGGAACAAATAC   40
    AATCTCAATCAGTACAAGTAGGCTTCAAGAGTTGATATTA   80
    ATGGAAATCATCCAAATTACACTTGGGTCACAAATAATTA  120
    CCCCACATAAAAAGGGAAAAAAAAAaTCTCATTCAGGGgA  160
    AGGGAAAGGTTTCCTGCAATGGTTTTCATGGCAGTGGGTA  200

210       220       230       240
    ....|....|....|....|....|....|....|....|
    GGTAGTCTTGCACTTTgGACTGGTCATATCTGTCAGTCTC  240
    TGGGCAGAGCAAA                             253
```

FIG.3A

```
 157  CCTGAATGAGATTTTTTTTTTCCCTTTTTATGTGGGGTAATTATTTGTGACCCAAGTGTA   98
      ||||||||||||||||||||||||||||||||||||||||||||||||||||||||||||
3505  CCTGAATGAGATTTTTTTTTTCCCTTTTTATGTGGGGTAATTATTTGTGACCCAAGTGTA 3564

97  ATTTGGATGATTTCCATTAATATCAACTCTTGAAGCCTACTTGTACTGATTGAGATTGTA   38
      ||||||||||||||||||||||||||||||||||||||||||||||||||||||||||||
3565  ATTTGGATGATTTCCATTAATATCAACTCTTGAAGCCTACTTGTACTGATTGAGATTGTA 3624

37  TTTGTTCCTAATAAAAGTGGATCTGGTTGTACTGCC    2
      ||||||||||||||||||||||||||||||||||| |
3625  TTTGTTCCTAATAAAAGTGGATCTGGTTGTACTGTC  3660

217  CAAAGTGCAAGACTACCTACCCACTGCCATGAAAACCATTGCAGGAAACCTTTCCCTTCC  158
      ||||||||||||||||||||||||||||||||||||||||||||||||||||||||||||
3447  CAAAGTGCAAGACTACCTACCCACTGCCATGAAAACCATTGCAGGAAACCTTTCCCTTCC 3506

157  CCTGAATGAGATTTTTTTTTTCCCTTTTTATGTGG  123
      ||  |||||||||  |  ||| ||  || ||
3507  TGAATGAGATTTTTTTTTTCCCTTTTTATGTGGGG 3541
```

FIG.3B

```
   8  CCCTTCCAATACAAGAACTAAGTGACTAGACTTCCAGTGATCCCTCTCCCAGCTCTTCC   67
         |||||||||||||||||||  |||||||||||||||||||||||||||||||||||||
2347  CCCTTCCAATACAAGAACTAAGCAGACTAGACTTCCAGTGATCCCTCTCCCAGCTCTTCC  2406

68  CTTCCCAGTTGTCCCCACTGTAACTCAAAAG   99
        || |||||||||||||||||||||||||| |
2407  CTCTCCCAGTTGTCCCCACTGTAACTCAAAGG  2438

96  AAAGGATGGAATACCAAGGTCTTTTATTCCTCGTGAAAAAAAAAAAA   143
        ||||||||||||||||||||||||| ||||  ||||  |||||| |
2434  AAAGGATGGAATACCAAGGTCTTTTTATTCTTCGTGCCAAAAAAAGA  2481
```

FIG.4

```
  69 ATCTCTTTTGGCAGAACATGAATGCAGGTCACCTGGTGTCAATACTCAGCCAGGCTGAGA 128
     | |||||||| ||||||||||||||||||||||||||||||||||||||||||||||||
1848 AGCTCTTTTGCCAGAACATGAATGCAGGTCACCTGGTGTCAATACTCAGCCAGGCTGAGA 1907

129 GCAACTTGGTGGCCTCGCTGGTTAAGGAGAGTGGTACTACAGCTTCCAATGTCTGGACTG 188
     ||||||| ||||||||||||||||||||||||||||||||||||||||||||||||||||
1908 GCAACTTTGTGGCCTCGCTGGTTAAGGAGAGTGGTACTACAGCTTCCAATGTCTGGACTG 1967

189 GACTTCATGACCCTAAAAGT 208
     ||||||||||||||||||||
1968 GACTTCATGACCCTAAAAGT 1987

209 AACCGTCGNTGGCACTGGAGCAGTGGCTCCCTATTTCTCTTCAAGTCATGGGCCACTGGA 268
     |||||||| |||||||||||||||||||||||||||||||||||||||||||||||||||
2979 AACCGTCGTTGGCACTGGAGCAGTGGCTCCCTATTTCTCTTCAAGTCATGGGCCACTGGA 3038

269 GCTCCAAGCACTGCCAACCGGGTT 292
     ||||||||||||||||||||| ||
3039 GCTCCAAGCACTGCCAACCGTGGT 3062

8 AACGCCTATGGTTCCTACTGTTATTATCTAATTGAAGACCGCTTGACCTGGGGGGAGGCT 67
     |||||||||||||||||||||||||||||||||||||||| |||||||||||||||||||
1563 AACGCCTATGGTTCCTACTGTTATTATCTAATTGAAGACCGTTTGACCTGGGGGGAGGCT 1622

68 GATCT 72
     ||| |
1623 GATGT 1627

318 AGGATACAAAAAATGGGAGGACGAAAACTGTGAGGCACAGTACTCCTTGGTCTTGAAGTT 377
     || ||||||||||||| |||||||||||||||||||||||||||||||| |||| |||||
3279 AGCATACAAAAAATGGAAGGACGAAAACTGTGAGGCACAGTACTCCTTTGTCTGCAAGTT 3338

378 CAGAGGCTAA 387
     ||||| ||||
3339 CAGAGCCTAA 3348
```

FIG.5

```
   2 GGCTTAGTCAGCCACTTTACAGACTGGTCTTCCTGCTGGCACATACTGTGATGTCATCTC   61
     |||||  |||||||||||||||||||||||||||||||||||||||||||||||||||||
1355 GGCTTTGTCAGCCACTTTACAGACTGGTCTTCCTGCTGGCACATACTGTGATGTCATCTC 1414

62 TGGAGATAAGGTCGATGGCAATTGCACTGGACTTAGAGTGAATGTTGGCAGTGATGGCAA  121
     ||||||||||||||||||||||||||||||||||||||||||||||||||||||||||||
1415 TGGAGATAAGGTCGATGGCAATTGCACTGGACTTAGAGTGAATGTTGGCAGTGATGGCAA 1474

122 AGCTCACTTTTCCATTAGTAACTCTGCTGAGGACCCATTTATTGCAATCCATGCTGACTC  181
     ||||||||||||||||||||||||||||||||||||||||||||||||||||||||||||
1475 AGCTCACTTTTCCATTAGTAACTCTGCTGAGGACCCATTTATTGCAATCCATGCTGACTC 1534

182 AAAATTGTAAGAATCTATATTAAAGAGATTTGGATTAGGAA  222
     ||||||||||||||||||||||||||||||||||||| | |
1535 AAAATTGTAAGAATCTATATTAAAGAGATTTGGATTAAGCA 1575
```

FIG.6

```
  24 AGAGTCAAGGGCTAGTGCGCACCGCAGCCAGCGCCCAGTACCGTGGCGTTCTGGGTACCA   83
     |||  |||||    |   |||    |    || |  ||||  ||  || ||||||  | |
 247 AGATCCAAGGCGAGTTCCCGATCACCAGCGGCATCAGGTACAAAGGTGTCCTGGGGACAA  306

84 TCCTAACCATGGTGCGCACTGAGGGTCCACGCAGCCTCTACAATGGGCTGGTCGCCGGCC  143
     ||   |||  |||   ||    || ||   || ||    |   ||||||| || |||||||
 307 TCACCACCCTGGCAAAAACGGAAGGGCCCCTGAAACTCTACAGCGGGTTGCCCGCCGGCC  366

144 TGCAGCGCCAGATGAGCCTTGCCTCCGTCCGCATTGGCCTCTACGACTCTGTCAAACAGT  203
     | ||| | ||  || ||| |  |||| |  || || | |||||||||| |  |  | |||
 367 TCCAGAGACAAATCAGCTTCGCCCTCGCTCAGGATCGGCCTCTACGACACGGTGCAGGAGT  426

204 TCTACACCAAGGGCTCAGAGCATGGAGGCATCGGGAGCCGCCTCCTGGCAGGTAGCACCA  263
     ||| ||||   |||    |||   ||||   |    | || ||   || ||   ||  ||
 427 TCTTCACCTCGGGGGAAGAAACACCGAGTTTAGGAAGCAAGATCTCGGCCGGCCTAACAA  486

264 CAGGTGCCCTGGCCGTGGTTGTAGCCCAGCCTACAGATGTGGTAAAGGTCCGCTTCCAGG  323
     | || | ||||||| ||| |  ||||||||||||||| |||| | || || || |  || |
 487 CTGGAGGCGTGGCGGTGTTCATCGGGCAGCCCACAGAGGTCGTGAAAGTCAGGCTGCAAG  546

324 CTCCAGGCC  332
     | |   |||
 547 CGCAGAGCC  555
```

FIG.7

```
 42 AAGATGCTGCTGCTGCTGTGTTTGGGACTGACCCTAGTCTGTGTCCATGCAGAAGAA 101
    | || |  ||||||||||||||||||||||||||||||||||||||||||||||||||
 59 ATGAAGATGCTGCTGCTGCTGTGTTTGGGACTGACCCTAGTCTGTGTCCATGCAGAAGAA 118

102 GCTAGTTCTACGGGAAGGAACTTTAATGTAGAAAAGATTAATGGGGAATGGCATACTATT 161
    ||||||||||||||||||||||||||||||||||||||||||||||||||||||||||||
119 GCTAGTTCTACGGGAAGGAACTTTAATGTAGAAAAGATTAATGGGGAATGGCATACTATT 178

162 ATCCTGGCCTCTGACAAAAGAGAAAAGATAGAAGATAATGGCAACTTTAGACTTTTTCTG 221
    ||||||||||||||||||||||||||||||||||||||||||||||||||||||||||||
179 ATCCTGGCCTCTGACAAAAGAGAAAAGATAGAAGATAATGGCAACTTTAGACTTTTTCTG 238

222 GAGCAAATCCATGTCTTGGAGAAATCCTTAGTTCTTAAAATCCATCCTGTAAGAGATGAA 281
    |||||||||||||||||||||||||||||||||||||| ||||| |||||||||||||||
239 GAGCAAATCCATGTCTTGGAGAAATCCTTAGTTCTTAAATTCCATACTGTAAGAGATGAA 298

282 GAGTGCTCCGAATTATCTATGGTTGCTGACAAAACAGAAAAGGCTGGTGAATATTCTGTG 341
    ||||||||||||||||||||||||||||||||||||||||||||||||||||||||||||
299 GAGTGCTCCGAATTATCTATGGTTGCTGACAAAACAGAAAAGGCTGGTGAATATTCTGTG 358

342 ACGTATGATGGATTCAATACATTTACTATACCTAAGACAGACTATGATAACTTTCTTATG 401
    ||||||||||||||||||||||||||||||||||||||||||||||||||||||||||||
359 ACGTATGATGGATTCAATACATTTACTATACCTAAGACAGACTATGATAACTTTCTTATG 418

402 GCTCATCTCATTAACGAAAAGGATGGGGAAACCTTCCAGCTGATGGGGCTCTATGGCCGA 461
    ||||||||||||||||||||||||||||||||||||||||||||||||||||||||||||
419 GCTCATCTCATTAACGAAAAGGATGGGGAAACCTTCCAGCTGATGGGGCTCTATGGCCGA 478

462 GAACCAGATTTGAGTTCAGACATCAAGGAAAGGTTTGCACAACTATGTGAGGAGCATGGA 521
    ||||||||||||||||||||||||||||||||||||||||| |||||||||||||||||
479 GAACCAGATTTGAGTTCAGACATCAAGGAAAGGTTTGCAAAACTATGTGAGGAGCATGGA 538

522 ATCCTTAGAGAAAATATCATTGACCTATCCAATGCCAATCGCTGCCTCCAGGCCCGAGAA 581
    ||||||||||||||||||||||||||||||||||||||||||||||||||||||||||||
539 ATCCTTAGAGAAAATATCATTGACCTATCCAATGCCAATCGCTGCCTCCAGGCCCGAGAA 598

582 TGAAGATTGGCCTGAGCCTCCAGTGTTGAGTGGAGACTTCTCACCAGGACTCCACCATCA 641
    ||||| ||||||||||||||||||||||||||||||||||||||||||||||||||||||
599 TGAAGAATGGCCTGAGCCTCCAGTGTTGAGTGGAGACTTCTCACCAGGACTCCACCATCA 658
```

FIG.8A

642 TCCCTTCCTATCCATACAGCATCCCCAGTATAAATTCTGTGATCTGCATTCCATCCTGTC 701
    ||||||||||||||||||||||||||||||||||||||||||||||||||||||||||||
659 TCCCTTCCTATCCATACAGCATCCCCAGTATAAATTCTGTGATCTGCATTCCATCCTGTC 718

702 TCACTGAGAAGTCCAATTCCAGTCTATCCACATGTTACCTAGGATACCTCATCAAGAATC 761
    ||||||||||||||||||||||||||||||||||||||||||||||||||||||||||||
719 TCACTGAGAAGTCCAATTCCAGTCTATCCACATGTTACCTAGGATACCTCATCAAGAATC 778

762 AAAGACTTCTTTAAATTTCTCTTTGATATACCCATGACAATTTTTCATGAATTTCTTCCT 821
    ||||||||||||||||||||||||||||||||||||||||||||||||||||||||||||
779 AAAGACTTCTTTAAATTTCTCTTTGATATACCCATGACAATTTTTCATGAATTTCTTCCT 838

822 CTTCCTGTTCAATAAATGATTACCCTTGCACTTA 855
    ||||||||||||||||||||||||||||||||||
839 CTTCCTGTTCAATAAATGATTACCCTTGCACTTA 872

FIG.8B

282  TGACCCGTACTTATTACAGCCGTACTGCTCCTATTATCACTACCAGTGCTAGCCGCAGGC 223
     ||| ||||||||||||||||||||||||||||||||||||||||||||||||||||||||
5883 TGATCCGTACTTATTACAGCCGTACTGCTCCTATTATCACTACCAGTGCTAGCCGCAGGC 5942

222  ATTACTATACTACTAACAGACCGCAACCTAAACACAACTTTCTTTGATCCCGCTGGAGGA 163
     ||||||||||||||||||||||||||||||||||||||||||||||||||||||||||||
5943 ATTACTATACTACTAACAGACCGCAACCTAAACACAACTTTCTTTGATCCCGCTGGAGGA 6002

162  GGGGACCCAATTCTCTACCAGCATCTGTTCTGATTCTTTGGGCACCCAGAAGTTTATATT 103
     ||||||||||||||||||||||||||||||||||||||||||||||||||||||||||||
6003 GGGGACCCAATTCTCTACCAGCATCTGTTCTGATTCTTTGGGCACCCAGAAGTTTATATT 6062

102  CTTATCCTCCCAGGATTTGGAATTATTTCACATGTAGTTACTTACTACTCCGGAAAAAAA 43
     ||||||||||||||||||||||||||||||||||||||||||||||||||||||||||||
6063 CTTATCCTCCCAGGATTTGGAATTATTTCACATGTAGTTACTTACTACTCCGGAAAAAAA 6122

42   GAACCTTTCGGCTATATAGGAATAGTATGAAAAAAAA 6
     ||||||||||||||||||||||||||||||||| || ||
6123 GAACCTTTCGGCTATATAGGAATAGTATGAGCAATAA 6159

FIG.9

```
  1  TTGTTGCGATCCCACCAACCTACACTATGAGTTTCTTGTCCCGTTGATCCTGGGCTGCAT   60
     ||||  |||||||||||||||||||||||||||||||||||||||||||||||||||||
237  TTGTCACGATCCCACCAACCTACACTATGAGTTTCTTGTCCCGTTGATCCTGGGCTGCAT  296

61  GAGGTTAAAGGGAATGATTGAGACCAGACAAGTCAGGGGTTGAAACTTAGAAAAGGTCAA  120
     ||||||||||||||||||||||||||||||||||||||||||||||||||||||||||||
297  GAGGTTAAAGGGAATGATTGAGACCAGACAAGTCAGGGGTTGAAACTTAGAAAAGGTCAA  356

121  AGGTACAGAAGAAACAGAGGACACTTCGTAGACTTGCAGAGGATATTTCAAAGGTAGCCA  180
     ||||||||||||||||||||||||||||||||||||||||||||||||||||||||||||
357  AGGTACAGAAGAAACAGAGGACACTTCGTAGACTTGCAGAGGATATTTCAAAGGTAGCCA  416

181  GAGAAGGGGGAAATTATACTATGTTGTCAATAGGAATAATAAAATAATAAAAGTAGATAT  240
     ||||||||||||||||||||||||||||||||||||||||||||||||||||||||||||
417  GAGAAGGGGGAAATTATACTATGTTGTCAATAGGAATAATAAAATAATAAAAGTAGATAT  476

241  TATTTATGAA   251
     |||||||||  |
477  TATTTATGCA   487
```

FIG.10

```
237  GGTKGTTGAGTGTGGCTGACTGGGATGCGCAGAGACCCAATGGTTCAGGCGCTGCCTGTC  178
     ||   |||||||||||||||||||||||||||||||||||||||||||||||||||||||
628  GGGTGGTGAGTGTGGCTGACTGGGATGCGCAGAGACCCAATGGTTCAGGCGCTGCCTGTC  687

177  TGTCTGCCACTCCATCTTTCCTGTTGCCAGAGAGCCACCTGGCTGCCCCACCAGCCACCA  118
     ||||||||||||||||||||||||||||||||||||||||||||||||||||||||||||
688  TGTCTGCCACTCCATCTTTCCTGTTGCCAGAGAGCCACCTGGCTGCCCCACCAGCCACCA  747

117  TACCAAGGAGCATCTGGAGCCTCTTCTTATTTGGCCAGCACTCCCCATCCACCTGTCTTA   58
     ||||||||||||||||||||||||||||||||||||||||||||||||||||||||||||
748  TACCAAGGAGCATCTGGAGCCTCTTCTTATTTGGCCAGCACTCCCCATCCACCTGTCTTA  807

57  ACACCACCAATGGCGTCCCCTTTCTGCTGAATAAATACATGCCCCC   12
     ||||||||||||||||||||||||||||||||||||||||||||||
808  ACACCACCAATGGCGTCCCCTTTCTGCTGAATAAATACATGCCCCC  853

263  CCGACCAATGCATTGACAACTGAATGGGTKGT  232
     ||||||||||||||||||||||||||||||  ||
603  CCGACCAATGCATTGACAACTGAATGGGTGGT  634
```

FIG.11

```
  1 TCCGCTCTGGATGCCAGGGTGATTCTGGGGGACCCCTCCACTGCATGGTGAACGGTCAGT  60
    ||||||||||||||||||||||||||||||||||||||||||||||||||||||||||||
527 TCCGCTCTGGATGCCAGGGTGATTCTGGGGGACCCCTCCACTGCATGGTGAACGGTCAGT 586

61 ATGCTGTCCACGGAGTGACCAGCTTTGTGTCCAGCATGGGCTGTAATGTCGCCAGGAAGC 120
    ||||||||| ||||||||||||||||||||||||||||||||||||||||||||||||||
587 ATGCTGTCGACGGAGTGACCAGCTTTGTGTCCAGCATGGGCTGTAATGTCGCCAGGAAGC 646

121 CCACCGTCTTCACCAGAGTCTCTGCTTACATTTTC  155
    ||||||||||||||||||| |||||||||||||| |
647 CCACCGTCTTCACCAGACTCTCTGCTTACATTTCC  681

315 AGCCTTGGGCTCCATCCCTAATACTGCAACAGGAGCAGGGGAATGCTGCTGGTGTCTTGG 374
    ||||||||||||||||||||||||||||||||||||||||||||||||||||||||||||
839 AGCCTTGGGCTCCATCCCTAATACTGCAACAGGAGCAGGGGAATGCTGCTGGTGTCTTGG 898

375 TATCTGGGGCAAAGGTGGGGGG  396
    ||||||||||||||||||||||
899 TATCTGGGGCAAAGGTGGGGGG  920

391 GGGGGGGGTTCATGAAAAGCAACTCAGACTACTGAATCAGATACAGAAAGGCAAATAAAA 450
    | ||||||||| ||||||||||||||||||||||||||||||||||||||||||||||||
913 GTGGGGGGTTAATGAAAAGCAACTCAGACTACTGAATCAGATACAGAAAGGCAAATAAAA 972

451 ATCAATGTGTTA  462
    ||||||||||||
973 ATCAATGTGTTA  984
```

FIG.12

```
  39 GGGGCAGGGGATCTGCTCAGCTCTATGTTTGAGTTCAGTGAGAAGCTGAATGCCCTCCAG  98
     || |||||||||||||||||||||||||||||||||||||||||||||||||||||||||
1321 GGAGCAGGGGATCTGCTCAGCTCTATGTTTGAGTTCAGTGAGAAGCTGAATGCCCTCCAG 1380

99 CTCAGTGATGAGGAAATGAGCTTGTTCACAGCAGTTGTTCTGGTATCTGCAG  150
     ||||||||||||||||||||||||||||||||||||||||||||||||||||
1381 CTCAGTGATGAGGAAATGAGCTTGTTCACAGCAGTTGTTCTGGTATCTGCAG 1432

151 GATCGATCTGGAATTGAAAATGTCAACTCAGTGGAGGCTTTGCAGGAAACACTCATCCGT  210
     ||||||||||||||||||||||||||||||||||||||||||||||||||||||||||||
1432 GATCGATCTGGAATTGAAAATGTCAACTCAGTGGAGGCTTTGCAGGAAACACTCATCCGT 1491

211 GCACTAAGGACCTTAATAATGRAAAAACCATCCAAATGAGGCCTCCATTTTTACAAAAT  269
     |||||||||||||||||||||| |||| |  | ||    |  |  |  ||||   ||| |
1492 GCACTAAGGACCTTAATAATGAAAAACCATCCAAATGAGGCCTCCATTTTTACAAAATT 1550

233 AAAAACCATCCAAATGAGGCCTCCATTTTTACAAAATTACTTCTAAAGTTGCCAGRTCTT  292
     |||||||||||||||||||||||||||||||||||||||||||||||||||||||| ||||
1513 AAAAACCATCCAAATGAGGCCTCCATTTTTACAAAATTACTTCTAAAGTTGCCAGATCTT 1572

293 CGATCTTTAAACAACATGCACTC  315
     |||||||||||||||||||||||
1573 CGATCTTTAAACAACATGCACTC 1595

4 GGTAAGAAGTACAGTGTGGATGACCTGCACTCAATGGG   41
     ||||||||||||||||||||||||||||||||||||||
1285 GGTAAGAAGTACAGTGTGGATGACCTGCACTCAATGGG 1322
```

FIG.13

```
1/1                                   31/11
CGC TGT CTC GGG AGG TCT GAA GAC ATG AAG CTG CTT CAG GTT CTC CTT GTT TTG CTG TTT
                                met lys leu leu gln val leu leu val leu leu phe
61/21                                 91/31
GTG GCA CTT GCA GAT GGT GCA CAG CCC AAA AGA TGT TTT AGC AAC GTA GAA GGC TAC TGT
val ala leu ala asp gly ala gln pro lys arg cys phe ser asn val glu gly tyr cys
121/41                                151/51
AGG AAG AAA TGC AGA TTA GTG GAG ATA TCT GAG ATG GGA TGC CTG CAT GGG AAA TAC TGT
arg lys lys cys arg leu val glu ile ser glu met gly cys leu his gly lys tyr cys
181/61                                211/71
TGT GTT AAT GAG CTG GAG AAC AAA AAG CAC AAG GAG CAC TCA GTC GTT GAG GAG ACA GTC
cys val asn glu leu glu asn lys lys his lys glu his ser val val glu glu thr val
241/81                                271/91
AAA CTC CAA GAC AAG TCA AAA GTA CAA GAC TAT ATG ATC CTG CCC ACG GTC ACA TAC TAC
lys leu gln asp lys ser lys val gln asp tyr met ile leu pro thr val thr tyr tyr
301/101                               331/111
ACC ATC ACT ATC TGA ATG AAC CAC TTG TTC ACG AAG GCC GTT GTC CCC TGC AGC CCC ATG
thr ile ser ile OPA
361/121                               391/131
GAA TCC AGT GGG CTG CTT CTG TCC TGT CTC TTT CCT TCT GTG AAA CTT GAG TCT GCA CAC 421/141                               451/151
AAT AAA GTT CGA CCC TTT TGG CTG AAA AAA AAA AAA A
```

FIG.14

START

| 1/1 | | | | | | | | 31/11 | | | | | | |
|---|---|---|---|---|---|---|---|---|---|---|---|---|---|---|
| atg | gtt | ggt | ttc | aag | gcc | aca | gat | gtg | ccc | cca | aca | gcc | act | gtg | aag | ttc | ctg | ggg | gct |
| Met | val | gly | phe | lys | ala | thr | asp | val | pro | pro | thr | ala | thr | val | lys | phe | leu | gly | ala |

61/21                                                      91/31
ggg aca gct gcc tgc att gca gat ctc atc act ttc cct ctg gat acc gcc aag gtc cgg
gly thr ala ala cys ile ala asp leu ile thr phe pro leu asp thr ala lys val arg 121/41                                                     151/51
ctg cag atc caa ggg gag agt caa ggg cta gtg cgc acc gca gcc agc gcc cag tac cgt
leu gln ile gln gly glu ser gln gly leu val arg thr ala ala ser ala gln tyr arg 181/61                                                     211/71
ggc gtt ctg ggt acc atc cta acc atg gtg cgc act gag ggt cca cgc agc ctc tac aat
gly val leu gly thr ile leu thr met val arg thr glu gly pro arg ser leu tyr asn 241/81                                                     271/91
ggg ctg gtc gcc ggc ctg cag cgc cag atg agc ctt gcc tcc gtc cgc att ggc ctc tac
gly leu val ala gly leu gln arg gln met ser leu ala ser val arg ile gly leu tyr 301/101                                                    331/111
gac tct gtc aaa cag ttc tac acc aag ggc tca gag cat gga ggc atc ggg agc cgc ctc
asp ser val lys gln phe tyr thr lys gly ser glu his gly gly ile gly ser arg leu 361/121                                                    391/131
ctg gca ggt agc acc aca ggt gcc ctg gcc gtg gtt gta gcc cag cct aca gat gtg gta
leu ala gly ser thr thr gly ala leu ala val val val ala gln pro thr asp val val 421/141                                                    451/151
aag gtc cgc ttc cag gct cca ggc cgg gct ggt ggt ggt cgg aga tac aga gca ctg tcg
lys val arg phe gln ala pro gly arg ala gly gly gly arg arg tyr arg ala leu ser 481/161                                                    511/171
agc tac aag aac atc acg aga gga ggg atc cgg ggc ctc tgg aag gga ctc tcc caa tgt
ser tyr lys asn ile thr arg gly gly ile arg gly leu trp lys gly leu ser gln cys 541/181                                                    571/191
gcc cgt aat gcc att gtc aac tgt gct gag ctg gtg acc tat gac ctc atc aaa gat act
ala arg asn ala ile val asn cys ala glu leu val thr tyr asp leu ile lys asp thr 601/201                                                    631/211
ctc ctg agc cac ctc atg aca gat gac ctc cct tgc cac ttc act tct gcc ttc ggg gcg
leu leu ser his leu met thr asp asp leu pro cys his phe thr ser ala phe gly ala 661/221                                                    691/231
ggc ttc tgc acc acc gtc atc gcc tcc cct gtg gat gtg gtc aag acg aga tac atg act
gly phe cys thr thr val ile ala ser pro val asp val val lys thr arg tyr met thr 721/241                                                    751/251
ctg ctg ggc cag tac cac agc gca ggt cac tgt gcc ctt aca tgc tcg gag gag gga ccc
leu leu gly gln tyr his ser ala gly his cys ala leu thr cys ser glu glu gly pro

FIG.16A

781/261                              811/271
gcg ctc ttc aac cag ggg gtt atg cct tcc ttt ctc cgc ttg gga tcc tgg aac gta gtg
ala leu phe asn gln gly val met pro ser phe leu arg leu gly ser trp asn val val
841/281                              871/291
atg ttt gtc acc tat gag cag ctc caa aga gcc cta atg gct gcc tac caa tct cgg gag
met phe val thr tyr glu gln leu gln arg ala leu met ala ala tyr gln ser arg glu
901/301                              931/311
gca cct ttc |tga| gcc tct cca tgc tga cct gga ccc tgc ttc cca gcc ctg ccc tgt ctt
ala pro phe |OPA|
961/321        STOP                  991
ttt ctt cat cct ctg ccc agt ccc att ctc ttc cca ttt cct gca ccc cga ttt act tcc 1021                                 1051
cac ctc acc tcc ctg tgc ctc tgt act gat gac tca cag tga gga ggc ctg aca cca gac 1081                                 1111
cct gag ccc tca gcc ctt tct aca gct aag ccc aca tct tca tct tca tcc cca gcc cag 1141                                 1171
ccc agc cca gct cag cca gcc ttc acc cat aaa gca agc tca atg tta aaa aaa aaa aaa 1201
aaa aa

FIG.16B

```
mC5   MVGFKATDVPPTATVKFLGAGTAACIADLITFPLDTAKVRLQIQGESQGLVRTAASAQYR    60
      ||·   ···|·||  ||···||··||·||·||||||||||||||||||·|    ···· ·|·
mUCP  MVNPTTSEVQPTMGVKIFSAGVSACLADIITFPLDTAKVRLQIQGEGQ----ASSTIRYK    56 mC5   GVLGTILTMVRTEGPRSLYNGLVAGLQRQMSFASVRIGLYDSVKQFYTKGSE-HAGIGSR   119
      ||||||  |···|||    ||·||  ||·|||  ||·|||·||||·|||||||·····  || ||  |··|··
mUCP  GVLGTITTLAKTEGLPKLYSGLPAGIQRQISFASLRIGLYDSVQEYFSSGRETPASLGNK   116 mC5   LLAGSTTGALAVAVAQPTDVVKVRFQAQARAGGGR-RYQSTVEAYKTIAREEGIRGLWKG   178
      ·||  ||··||  ··|||·|||||  |||··   |·||·|·||··||  |··  ||||
mUCP  ISAGLMTGGVAVFIGQPTEVVKVRMQAQSHLHGIKPRYTGTYNAYRVIATTESLSTLWKG   176 mC5   TSPNVARNAIVNCAELVTYDLIKDTLLKANLMTDDLPCHFTSAFGAGFCTTVIASPVDVV   238
      |·||·  ||·|·||·||||||||·|··|······||·|||·  ||·  ||||||··||||||
mUCP  TTPNLMRNVIINCTELVTYDLMKGALVNNKILADDVPCHLLSALVAGFCTTLLASPVDVV   236 mC5   KTRYMNSALGQYHSAGHCALTMLRK<u>EGPRAFYKG</u>FMPSFLRLGSWNVVMFVTYEQLKRAL   298
      |||··||   |||  |·   ||··|    ||||  ||·|||··|||||||||||·|||   ||||··|
mUCP  KTRFINSLPGQYPSVPSCAMSMYTK<u>EGPTAFFKG</u>FVASFLRLGSWNVIMFVCFEQLKKEL   296 mC5   MAAYQSREAPF   309
      |·|··
mUCP  MKSRQTVDCTT   307
```

FIG.17A

```
mC5  MVGFKATDVPPTATVKFLGAGTAACIADLITFPLDTAKVRLQIQGESQGLVRTAASAQYR  60
     ||||||||||||||||||||||||||||||||||||||||||||||||| ||...|||||
hC5  MVGFKATDVPPTATVKFLGAGTAACIADLITFPLDTAKVRLQIQGESQGPVRATVSAQYR  60 mC5  GVLGTILTMVRTEGPRSLYNGLVAGLQRQMSFASVRIGLYDSVKQFYTKGSEHAGIGSRL  120
     ||·|||||||||||||||||||||||||||||||||||||||||||||||||·|||||
hC5  GVMGTILTMVRTEGPRSLYNGLVAGLQRQMSFASVRIGLYDSVKQFYTKGSEHASIGSRL  120 mC5  LAGSTTGALAVAVAQPTDVVKVRFQAQARAGGGRRYQSTVEAYKTIAREEGIRGLWKGTS  180
     |||||||||||||||||||||||||||||||||||||||||·|||||||||·||||||||
hC5  LAGSTTGALAVAVAQPTDVVKVRFQAQARAGGGRRYQSTVNAYKTIAREEGFRGLWKGTS  180 mC5  PNVARNAIVNCAELVTYDLIKDTLLKANLMTDDLPCHFTSAFGAGFCTTVIASPVDVVKT  240
     |||||||||||||||||||||||·||||||||||||||||||||||||||||||||||||
hC5  PNVARNAIVNCAELVTYDLIKDALLKANLMTDDLPCHFTSAFGAGFCTTVIASPVDVVKT  240 mC5  RYMNSALGQYHSAGHCALTMLRK<u>EGPRAFYKG</u>FMPSFLRLGSWNVVMFVTYEQLKRALMA  300
     ||||||||| |||||||||||·||||||||||||||||||||||||||||||||||||||
hC5  RYMNSALGQYSSAGHCALTMLQK<u>EGPRAFYKG</u>FMPSFLRLGSWNVVMFVTYEQLKRALMA  300 mC5  AYQSREAPF  309
     |  ||||||
hC5  ACTSREAPF  309
```

FIG.17B

```
    CCT CCG CCA GCC GAC ATT AGC CGC ACG CAC TGC CGT GTT CTC CCT GCG GCT CGG
ACA CAT AGT ATG ACC ATA GCC ACT TGT TTC GTC TCC CAC CCA TTT TCT ATG GAA AAC CAA GGG
GAT CGG GCC ATG CCT GAG GGT GGC AGC TTT GAA GAA CGG GAC ACC TTT AGA GAA GCT TGA
TCT TGG AGG CAC CGT CAC GGT GCC ACC TTA CAA GGC CGG ATT CCG GCA GAG TTC CTC TAT CTC
GTC TTG CTG ATT AAA GGT GCC CCT GTC TCC AGT GTC TCC TCT CCA TTT TCT CCT GGG ACG TAG

CAG GAA ATC AGC ATC ATG GTT GGG TTC AAG GCC ACA GAT GTG CCC CCT ACT GCC ACT GTG
                    met val gly phe lys ala thr asp val pro pro thr ala thr val AAG TTT CTT GGG GCT GGC ACA GCT GCC TGC ATC GCA GAT CTC ATC ACC TTT CCT CTG GAT
lys phe leu gly ala gly thr ala ala cys ile ala asp leu ile thr phe pro leu asp ACT GCT AAA GTC CGG TTA CAG ATC CAA GGA GAA AGT CAG GGG CCA GTG CGC GCT ACA GTC
thr ala lys val arg leu gln ile gln gly glu ser gln gly pro val arg ala thr val AGC GCC CAG TAC CGC GGT GTG ATG GGC ACC ATT CTG ACC ATG GTG CGT ACT GAG GGC CCC
ser ala gln tyr arg gly val met gly thr ile leu thr met val arg thr glu gly pro CGA AGC CTC TAC AAT GGG CTG GTT GCC GGC CTG CAG CGC CAA ATG AGC TTT GCC TCT GTC
arg ser leu tyr asn gly leu val ala gly leu gln arg gln met ser phe ala ser val CGC ATC GGC CTG TAT GAT TCT GTC AAA CAG TTC TAC ACC AAG GGC TCT GAG CAT GCC AGC
arg ile gly leu tyr asp ser val lys gln phe tyr thr lys gly ser glu his ala ser ATT GGG AGC CGC CTC CTA GCA GGC AGC ACC ACA GGT GCC CTG GCT GTG GCC CAG
ile gly ser arg leu leu ala gly ser thr thr gly ala leu ala val ala gln
```

FIG.18A

```
CCC ACG GAT GTG GTA AAG GTC CGA TTC CAA GCT CAG GCC CGG GCT GGA GGT GGT CGG AGA
pro thr asp val val lys val arg phe gln ala gln ala arg ala gly gly gly arg arg TAC CAA AGC ACC GTC AAT GCC TAC AAG ACC ATT GCC CGA GAG GAA GGG TTC CGG GGC CTC
tyr gln ser thr val asn ala tyr lys thr ile ala arg glu glu gly phe arg gly leu TGG AAA GGG ACC TCT CCC AAT GTT GCT CGT AAT GCC ATT GTC AAC TGT GCT GAG CTG GTG
trp lys gly thr ser pro asn val ala arg asn ala ile val asn cys ala glu leu val ACC TAT GAC CTC ATC AAG GAT GCC CTC CTG AAA GCC AAC CTC ATG ACA GAT GAC CTC CCT
thr tyr asp leu ile lys asp ala leu leu lys ala asn leu met thr asp asp leu pro TGC CAC TTC ACT TCT GCC TTT GGG GCA GGC TTC TGC CTG GGC TTC ACT GTC ATC GCC TCC CCT GTA
cys his phe thr ser ala phe gly ala gly phe cys thr thr val ile ala ser pro val GAC GTG GTC AAG ACG AGA ACA TAC AAC ATG TCT GCC CTG GGC CAG TAC AGT GCT AGC GCT GGC CAC
asp val val lys thr arg tyr met asn ser ala leu gly gln tyr ser ser ala gly his TGT GCC CTT ACC ATG CTC CAG AAG GAG GGG CCC CGA GCC TTC TAC AAA GGG TTC ATG CCC
cys ala leu thr met leu gln lys glu gly pro arg ala phe tyr lys gly phe met pro TCC TTT CTC CGC TTG GGT TCC AAC GTG GTG ATG TTC GTC ACC TAT GAG CAG CTG AAA
ser phe leu arg leu gly ser asn val val met phe val thr tyr glu gln leu lys CGA GCC CTC ATG GCT GCC TGC ACT TCC CGA GAG GCT CCC TTC TGA GCC TCT CCT GCT GCT
arg ala leu met ala ala cys thr ser arg glu ala pro phe GAC CTG ATC ACC TCT GGC TTT GTC TCT AGC CGG GCC ATG CTT TCC TCT TCC TTC TTT
CTC TTC CCT CCT CTT CTT TCC CTT CTC TCA TTC CCT TCC CCT GCT CCT TTA
CCT ACC ACC TTC CCT GGG AGG CCT ACA TTC TCT ACT TGT CAT CCC AGT GCT GGA GTT
GAC ATT TGA CAG TGT CAG GAA TCT TCG ACC AGC GAT CAG CCC AAG GCT CCC GTC CCT TGG
AAA GTT CAG CCA CAA CCT CGA CGT TGC CCC CGA CAG AGC CTA GCC CAC TTG TCA TCC
ATA AAG CAA GCT CAA CCT TGA AAA AAA AAA AAA AAA AAA
```

FIG.18B

```
108  GATCCCTGGCCAGAAGTACAAAGACACTAACCTGCTAATACTCTTTAAGGAAGATTACTT  167
     ||||||||||||||||||||||||||||||||||||||||||||||||||||||||||||
647  GATCCCTGGCCAGAAGTACAAAGACACTAACCTGCTAATACTCTTTAAGGAAGATTACTT  706

168  TGCAAAAAAAAATGAAGAAAGAAAGCAGAGCAAAGTGGAAGCTAAATTAAAAGCTAAACA  227
     ||||||||||||||||||||||||||||||||||||||||||||||||||||||||||||
707  TGCAAAAAAAAATGAAGAAAGAAAGCAGAGCAAAGTGGAAGCTAAATTAAAAGCTAAACA  766

228  AGAGCATGAAGGAAGACACAAGCCAGGAAGTACTGAAACC  267
     ||||||||||||||||||||||||||||||||||||||||
767  AGAGCATGAAGGAAGACACAAGCCAGGAAGTACTGAAACC  806
```

FIG.20

```
189  AGGGTCAGTGGTCTCCAGTCTTCTCCCAGTTTGGGCTTATTGATGTCCAATAAACAAGTT  130
     |||| ||| ||   |      ||| |||||| || |||||||||||||||||||||| ||
4485 AGGGGCAGGGGCTCCATTCTTCTCCCCGGTTTGGTCTGATTGATGTCCAATAAACAACTT  4544

129  CTGTGTCTGCAAA  117
     |||| ||| ||||
4545 CTGTATCTTCAAA  4557

219  CCCTACCAACTCTGTGCAGTGGTTCGCTAAAGGGTCAGTGGTCTCCAGTCTTCTCCCAGT  160
     || |||||||||||||||||||| |||||| ||    || |||||  |||||||||||| |
4454 CCTTACCAACTCTGTGCAGTGGCTCGCTAGCAGGGGCAGGGGCTCCATTCTTCTCCCCGG  4513

159  TTGGG  155
     || ||
4514 TTTGG  4518
```

FIG. 21

```
  1    GGAATTCGGC ACGAGGAACT AGTCTCGAGT AGCTCTGTGT
 41    GTGTAGACAC TCCCTAAGCC ACCCGAGGGC TGCCTCTGTG
 81    TGGTGGGGAG GTAGGAGAGG GGAAGAGGGT TGCTATTCTC
121    ATTTTATACT TTTCCCACGG CTTCCAACTT TATGCCAATA
161    ACTCACAATT AAACAGGTCT CAGAACTAAG GGAGCTTTCA
201    ACACTTGGGC TAACTCAAGT GCAGTGAGCG AACGGGTTCT
241    CCAAACCTGC TGGGTCCTGG CTACCTATGT CACACAGATG
281    AGTGAGTCCA CCTGCCTTCC ATTCTCTGAG CTTGTGGTCA
321    CAGCAGGAGT CTTCCAGGGC ACTGCCTTGG STTGGAAATG
361    TAAGTCCGTC CGGAAATAGT ATCCCCATCA GCTCTCTGGT
401    GTTTGTGAGC TCTAGCATGC CATCCAGGTT CCAAGGAGGA
441    GAGTCACGAA GGTCCCAGAG CCGCAAGGTG CACAGAGCAC
481    CCTATAAACC CTGCAGTCCT CTTTGAGTCA TGGGGAGGAC
521    TGTGGATCCC CTTCTTTGAG TCTAAAGAGG CTCAGGAATC
561    CATATTCTCC ACAAGGTCCA GGTGGGAAGT GCATGCATGA
601    AATCAGACTC CAAAAAATGA ACCACAAGTC ACAGGAGAGA
641    GAGAGAACTA GTCTCGAGCT CGTGCCGAAT TCGGCACGAG
681    GTGTAGCTCA GGTAGCCCAG GGAGCAATCA AGCTCTGCTT
721    CCTGCTGCGC AGCTGTGGCT CGCTCCTGCC CGAACTGAGT
761    CTCGCCGAGA GGACAGAGTT TGCTCACAAG ATCTGGGACA
801    AACTTCAGCA GTTAGGTGTC GTATATGATG TCAGTCATTA
841    CAATGCTTTA CTTAAAGTAT ATCTTCAAAA TGAATACAAA
881    TTTTCACCTA CTGACTTCCT GGCAAAGATG GAGGGAGCAA
921    ACATCCAACC AAATCGAGTA ACATACCAGA GGCTGATAGC
961    TGCCTACTGT AATGTTGGGG ACATTGAAGG TGCCAGCAAG
1001   ATCCTTGGAT TTATGAAAAC GAAAGACCTT CCGATCACAG
1041   AGGGCGTGTT CAGTGCTCTC GTCACAGGGC ATGCCAGAGC
1081   TGGGGATATG GAAAATGCAG AAAATATTCT CACAGTGATG
1121   AAACAGGCCG GCATTGAGCC TGGCCCAGAC ACGTATCTGG
1161   CCTTGTTGAA TGCACATGCT GAGAGGGGTG ACATTGGCCA
1201   GGTTAGGCAG ATTCTGGAGA AAGTGGAGAA GTCAGACCAT
1241   TACTTCATGG ACCGCGACTT CTTGCAGGTT ATTTTTAGCT
1281   TCAGTAAGGC TGGCTACCCT CACTCGAG
```

FIG.22

COMPOSITIONS FOR THE TREATMENT OF BODY WEIGHT DISORDERS INCLUDING OBESITY

This is a division of application Ser. No. 08/946,719, filed Oct. 8, 1997, which is a division of application Ser. No. 08/807,861, filed Feb. 26, 1997, now U.S. Pat. No. 5,853,975, which is a continuation-in-part of application Ser. No. 08/518,878, filed Aug. 23, 1995, now U.S. Pat. No. 5,702,902, which is a continuation-in-part of application Ser. No. 08/470,868, filed Jun. 6, 1995, now U.S. Pat. No. 5,861,485, which is a continuation-in-part of application Ser. No. 08/294,522, filed Aug. 23, 1994 now U.S. Pat. No. 5,741,666, each of which is incorporated herein by reference in its entirety.

This is a continuation-in-part of Ser. No. 08/518,878, filed Aug. 23, 1995, which is a continuation-in-part of Ser. No. 08/470,868, filed Jun. 6, 1995, which is a continuation-in-part of Ser. No. 08/294,522, filed Aug. 23, 1994, each application of which is incorporated herein by reference in its entirety.

1. INTRODUCTION

The present invention relates to methods and compositions for the modulation of processes related to mammalian body weight regulation, including treatment of body weight disorders such as obesity and cachexia, and modulation of thermogenesis. Specifically, the present invention identifies and describes genes which are differentially expressed in body weight disorder states, relative to their expression in normal, or non-body weight disorder states, and also identifies genes which are differentially expressed in response to manipulations relevant to appetite and/or weight regulation. Further, the present invention identifies and describes genes via the ability of their gene products to interact with gene products involved in body weight disorders and/or to interact with gene products which are relevant to appetite and/or body weight regulation. Still further, the present invention provides methods for the identification and therapeutic use of compounds as treatments of body weight-related processes, including body weight disorders such as obesity and cachexia. Additionally, the present invention describes methods for the diagnostic evaluation and prognosis of various body weight disorders, and for the identification of subjects exhibiting a predisposition to such conditions.

2. BACKGROUND OF THE INVENTION

The regulation of body fat in mammals is a complex process involving the regulation of not only appetite but also energy expenditure. An important component of energy expenditure is non-shivering thermogenesis (NST). In rodents, the majority of NST appears to occur in brown adipose tissue (BAT) via the uncoupling protein (UCP) (Cannon & Nedergaard, 1985, Essays in Biochem. 20:110–165; Himms-Hagen J., 1989, Prog. Lipid Res. 28:67–115). UCP is a proton channel located exclusively in the inner mitochondrial membrane of adipocytes of the BAT (Nicholls & Locke, 1984, Physiol. Rev. 64:1–64). By allowing protons to equilibrate across the inner mitochondrial membrane, UCP uncouples oxidative phosphorylation from ATP production and thus converts stored energy into heat rather than work (Klingenberg M., 1990, Trends Biochem. Sci. 15:108–112; Klaus S. et al., 1991, Int. J. Biochem. 23:791–801). UCP-mediated uncoupling is not only capable of increasing body temperature in cold-acclimatized rodents and hibernating animals, but can also dissipate surplus caloric energy (Rothwell & Stock, 1986, In *Brown Adipose Tissue.* Trayhurn P., Nicholls D. G., Eds., London, Arnold, p. 269–298; Spiegelman & Flier, 1996, Cell 87:377–389; Hamann & Flier, 1996, Endocrinology 137:2129). A number of studies have now implicated UCP and brown adipose tissue as important regulators of body weight in rodents (Hamann & Flier, 1996, Endocrinology 137:2129; Lowell B. B. et al., 1993, Nature 366:740–742; Kopecky J. et al., 1995, J. Clin. Invest. 96:2914–2923; Cummings D. E. et al., 1996, Nature 382:622–626).

In humans, body weight homeostasis is poorly understood, but is also thought to involve regulated thermogenesis (Rothwell & Stock, 1981, Annu. Rev. Nutr. 1:235–56; Segal K. R. et al., 1992, J. Clin. Invest. 89:824–833; Jensen M. D. et al., 1995, Am. J. Physiol. 268:E433–438). However, the importance of the UCP in adult humans is questionable due to the low levels of BAT and consequently the low levels of UCP expression (Huttunen P. et al., 1981, Eur. J. Appl. Physiol. 46:339–345; Cunningham S. et al., 1985, Clin. Sci. 69:343–348; Schulz L., 1987, J. Am. Diet Assoc. 87:761–764; Santos G. C. et al., 1992, Arch. Pathol. Lab Med. 116:1152–1154).

In adult humans and other animals that do not contain large amounts of BAT, a large portion of NST and regulated thermogenesis is thought to be mediated by muscle and the white adipose tissue (Jensen M. D. et al., 1995, Am. J. Physiol. 268:E433–438; Davis T. R. A., 1963, Am. J. Physiol. 213:1423–1426; Astrup A. et al., 1989, Am. J. Physiol. 257:E340–E345, 1989; Simonsen L. et al., 1992, Am. J. Physiol. 263:E850–E855; Simonsen J. et al., 1993, Int. J. Obes. Relat. Metab. Disord. 17 (Suppl. 3):S47–51; Duchamp C. et al., 1993, Am. J. Physiol. 265:R1076–1083), however, the molecular mediators for regulated thermogenesis are currently unknown (Block B A., 1994, Annu. Rev. Physiol. 56:535–577).

Further, body weight disorders, including eating and other disorders affecting regulation of body fat, represent major health problems in all industrialized countries. Obesity, the most prevalent of eating disorders, for example, is the most important nutritional disorder in the western world, with estimates of its prevalence ranging from 30% to 50% within the middle-aged population. Other body weight disorders, such as anorexia nervosa and bulimia nervosa which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidences of diseases such as coronary artery disease, stroke, and diabetes. Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity. The nature, however, of the genetic factors which control body composition are unknown, and attempts to identify molecules involved in such control have generally been empiric and the parameters of body composition and/or substrate flux are monitored have not yet been identified (Friedman, J. M. et al., 1991, Mammalian Gene 1:130–144).

The epidemiology of obesity strongly shows that the disorder exhibits inherited characteristics, (Stunkard, 1990, N. Eng. J. Med. 322:1483). Moll et al., have reported that, in many populations, obesity seems to be controlled by a few genetic loci, (Moll et al. 1991, Am. J. Hum. Gen. 49:1243). In addition, human twin studies strongly suggest a substantial genetic basis in the control of body weight, with estimates of heritability of 80–90% (Simopoulos, A. P. & Childs B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65:279–287).

Further, studies of non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake.

In addition, it is a commonplace experience in animal husbandry that different strains of swine, cattle, etc., have different predispositions to obesity. Studies of the genetics of human obesity and of models of animal obesity demonstrate that obesity results from complex defective regulation of both food intake, food induced energy expenditure and of the balance between lipid and lean body anabolism.

There are a number of genetic diseases in man and other species which feature obesity among their more prominent symptoms, along with, frequently, dysmorphic features and mental retardation. Although no mammalian gene associated with an obesity syndrome has yet been characterized in molecular terms, a number of such diseases exist in humans. For example, Prader-Willi syndrome (PWS) affects approximately 1 in 20,000 live births, and involves poor neonatal muscle tone, facial and genital deformities, and generally obesity. The genetics of PWS are very complex, involving, for example, genetic imprinting, in which development of the disease seems to depend upon which parent contributes the abnormal PWS allele. In approximately half of all PWS patients, however, a deletion on the long arm of chromosome 11 is visible, making the imprinting aspect of the disease difficult to reconcile. Given the various symptoms generated, it seems likely that the PWS gene product may be required for normal brain function, and may, therefore, not be directly involved in adipose tissue metabolism.

In addition to PWS, many other pleiotropic syndromes which include obesity as a symptom have been characterized. These syndromes are more genetically straightforward, and appear to involve autosomal recessive alleles. The diseases, which include, among others, Ahlstroem, Carpenter, Bardet-Biedl, Cohen, and Morgagni-Stewart-Monel Syndromes.

Animals having mutations which lead to syndromes that include obesity symptoms have also been identified. Attempts have been made to utilize such animals as models for the study of obesity. The best studied animal models for genetic obesity are mice which contain the autosomal recessive mutations ob/ob (obese) and db/db (diabetes). These mutations are on chromosomes 6 and 4, respectively, but lead to clinically similar pictures of obesity, evident starting at about 1 month of age, which include hyperphagia, severe abnormalities in glucose and insulin metabolism, very poor thermo-regulation and non-shivering thermogenesis, and extreme torpor and underdevelopment of the lean body mass. Restriction of the diet of these animals to restore a more normal body fat mass to lean body mass ration is fatal and does not result in a normal habitus.

Although the phenotypes of db/db and ob/ob mice are similar, the lesions are distinguishable by means of parabiosis. The feeding of normal mice and, putatively, all mammals, is regulated by satiety factors. The ob/ob mice are apparently unable to express the satiety factor, while the db/db mouse is unresponsive to it.

In addition to ob and db, several other single gene mutations resulting in obesity in mice have been identified. These include the yellow mutation at the agouti locus, which causes a pleiotropic syndrome which causes moderate adult onset obesity, a yellow coat color, and a high incidence of tumor formation (Herberg, L. and Coleman, D. L., 1977, Metabolism 26:59), and an abnormal anatomic distribution of body fat (Coleman, D. L., 1978, Diabetologia 14:141–148). Additionally, mutations at the fat and tubby loci cause moderately severe, maturity-onset obesity with somewhat milder abnormalities in glucose homeostasis than are observed in ob and db mice (Coleman, D. L., and Eicher, E. M., 1990, J. Heredity 81:424–427). Further, autosomal dominant mutations at the adipose locus of chromosome 7, have been shown to cause obesity.

Other animal models include fa/fa (fatty) rats, which bear many similarities to the ob/ob and db/db mice, discussed above. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have been used as models for obesity have also been developed via physical or pharmacological methods. For example, bilateral lesions in the ventromedial hypothalamus (VMH) and ventrolateral hypothalamus (VLH) in the rat are associated, respectively, with hyperphagia and gross obesity and with aphagia and cachexia. Further, it has been demonstrated that feeding monosodium-glutamate (MSG) to new born mice also results in an obesity syndrome.

Attempts have been made to utilize such animal models in the study molecular causes of obesity. For example, adipsin, a murine serine protease with activity closely similar to human complement factor D, produced by adipocytes, has been found to be suppressed in ob/ob, db/db and MSG-induced obesity (Flier, 1987, Science 237:405). The suppression of adipsin precedes the onset of obesity in each model (Lowell, 1990, Endocrinology 126:1514). Further studies have mapped the locus of the defect in these models to activity of the adipsin promoter (Platt, 1989, Proc. Natl. Acad. Sci. USA 86:7490). Further, alterations have been found in the expression of neuro-transmitter peptides in the hypothalamus of the ob/ob mouse (Wilding, 1993, Endocrinology 132:1939), of glucose transporter proteins in islet β-cells (Ohneda, 1993, Diabetes 42:1065) and of the levels of G-proteins (McFarlane-Anderson, 1992, Biochem. J. 282:15).

To date, no gene, in humans, has been found which is causative in the processes leading to obesity. Likewise, to date, no molecular mediator of regulated thermogenesis in humans has been identified. Given the importance of understanding body weight homeostasis and, further, given the severity and prevalence of disorders, including obesity, which affect body weight and body composition, there exists a great need for the systematic identification of genes involved in these processes and disorders.

3. SUMMARY OF THE INVENTION

The present invention relates to methods and compositions for the treatment of body weight disorders, including, but not limited to, obesity and cachexia. The invention further provides methods for the modulation of processes relevant to appetite and/or body weight regulation, including, but not limited to, thermogenesis in mammals.

Specifically, the present invention identifies and describes genes which are differentially expressed in body weight disorder states, relative to their expression in normal, or non-body weight disorder states, and also identifies genes which are differentially expressed in response to manipulations relevant to appetite and/or body weight regulation. Such differentially expressed genes may represent "target genes" and/or "fingerprint genes". Further, the present invention identifies and describes genes, termed "pathway genes", via the ability of their gene products to interact with gene products involved in body weight disorders and/or to interact with gene products which are relevant to appetite and body weight regulation. Pathway genes may also exhibit target gene and/or fingerprint gene characteristics.

"Differential expression", as used herein, refers to both quantitative as well as qualitative differences in the genes' temporal and/or tissue expression patterns. "Fingerprint gene," as used herein, refers to a differentially expressed gene whose expression pattern may be utilized as part of a prognostic or diagnostic body weight disorder evaluation, or which, alternatively, may be used in methods for identifying compounds useful for the treatment of body weight disorders. "Target gene", as used herein, refers to a differentially expressed gene involved in body weight disorders and/or appetite or body regulation such that modulation of the level of target gene expression or of target gene product activity may act to ameliorate symptoms of body weight disorders including, but are not limited to, obesity.

This invention is based, in part on systematic, search strategies involving body weight disorder experimental paradigms coupled with sensitive gene expression assays.

The present invention also describes the products of such fingerprint, target, and pathway genes, describes antibodies to such gene products, and still further describes cell- and animal-based models of body weight disorders to which such gene products may contribute.

Among the target genes and gene products of the present invention are the C5 genes and gene products, including, but not limited to, the murine and human C5 genes and gene products, as depicted in FIGS. 16A–16B (murine) and 18A–18B (human). As demonstrated in the Examples presented in Sections 10 and 11, C5 gene products are expressed in tissues (e.g., muscle and adipose tissue) involved in thermogenesis.

Further, the Example presented in Section 12, below, proves that C5 gene products are involved in thermogenesis in that such products exhibit uncoupling activities or properties. An uncoupling property or activity refers to an ability of the gene product to transport protons across the mitochondrial inner membrane, thereby reducing proton motive force and allowing caloric energy to be dissipated in the form of heat. Thus the C5 gene products are demonstrated herein to exhibit the ability to uncouple oxidative phosphorylation, thereby dissipating caloric energy in the form of heat. Such C5 genes and gene products regulate thermogenesis and can be involved in body weight regulation via uncoupling activities.

The invention further provides methods for the identification of compounds which modulate the expression of genes or the activity of gene products involved in body weight disorders and processes relevant to appetite and/or body weight regulation.

With respect to the C5 genes and gene products, such compounds can, for example, modulate C5 uncoupling activity, either by affecting the level of C5 gene expression or by modulating (increasing, stimulating, decreasing or inhibiting) the level of C5 gene product activity.

Still further, the present invention describes methods for the treatment of body weight disorders and the modulation of thermogenesis in mammals which may involve the administration of such compounds to individuals exhibiting body weight disorder symptoms or tendencies or in need of regulation of thermogenesis.

With respect to the C5 genes and gene products, such treatment methods can, for example, modulate C5 uncoupling activity, either by modulating the level of C5 gene expression or by modulating the level of C5 gene product activity. Such methods can be utilized for the modulation of thermogenesis and body weight regulation. Increasing the level of C5 gene expression and/or gene product activity can increase the rate of thermogenesis and can cause a reduction in body weight, including a reduction in body weight associated with obesity. Decreasing the level of C5 gene expression and/or C5 gene product activity can decrease the rate of thermogenesis and can cause an increase in body weight, including an increase in body weight associated with cachexia.

Additionally, the present invention describes methods for prognostic and diagnostic evaluation of various body weight disorders, and for the identification of subjects exhibiting a predisposition to such disorders.

The Examples presented in Sections 6–9, below, demonstrate the successful use of the body weight disorder paradigms of the invention to identify body weight disorder target genes. The Examples presented in Sections 10–12 describe the identification, cloning and characterization of the novel C5 genes.

4. DESCRIPTION OF THE FIGURES

FIG. 1. Differential display comparing RNAs from liver tissue of lean and obese mice. Each group (1–11) of four lanes shows the pattern obtained with one primer pair combination, for a total of eleven different primer pair combinations. All lanes are products of a polymerase chain reaction (PCR) in which $T_{11}GG$ was used as the 3' oligonucleotide and one of eleven different arbitrary 10mer oligonucleotides was used as the 5' oligonucleotide. Within each group of four lanes, the loading is as follows, from left to right: C57B1/6J lean control (marked "C"); C57B1/6J ob/ob (marked "ob"); C57B1/Ks lean control (marked "C"); and C57B1/Ks db/db (marked "db"). An arrow indicates a band (designated L36) that is differential between obese and lean samples amplified by the same primer pair, specifically, primer pair 6.

Figure 2:
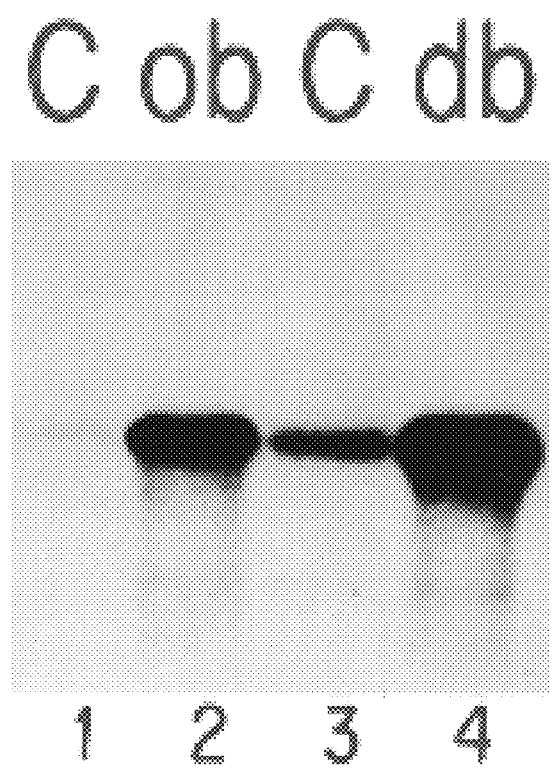

FIG. 2. Northern blot analysis confirming differential regulation of a gene corresponding to band L36. Poly A⁺ RNA (1 μg/lane) obtained from the original liver total RNA preparations was hybridized with a cDNA probe prepared by random priming of reamplified lane L36 (see materials and methods, below, in Section 6.1). Lane 1, C57B1/6J lean control ("C"); lane 2, C57B1/6J ob/ob ("ob"); lane 3 C57B1/Ks lean control ("C") ; and lane 4, C57B1/Ks db/db ("db").

Figures 1, 23A:
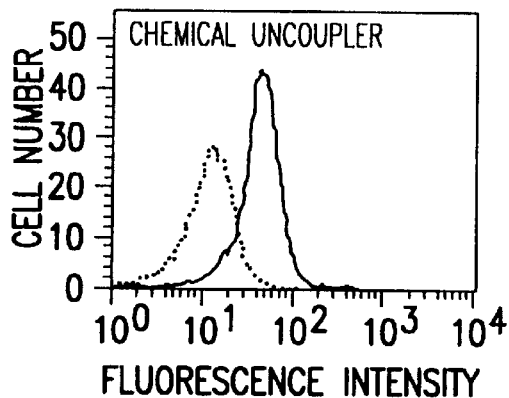
Figures 2, 23A:
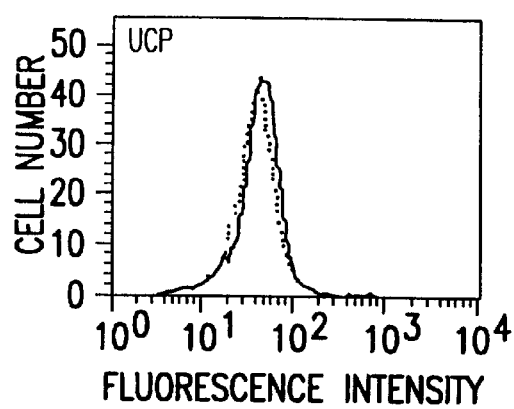
Figures 3, 23A:
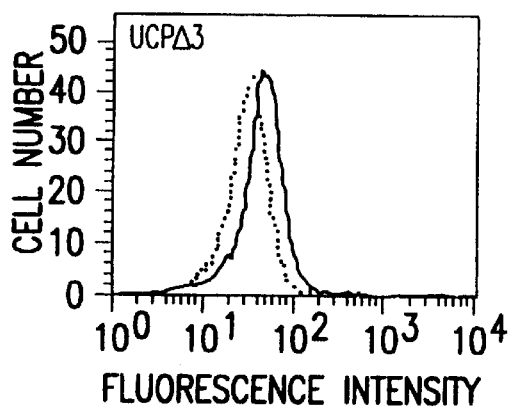

FIG. 3A. Consensus nucleotide sequence of L36 amplified band (SEQ. ID NO: 1). The IUPAC-IUB Standard Code is used (with the addition of the "X" designation, as shown below) in this nucleotide sequence and those nucleotide sequences listed in the figures which follow. Upper case letters refer to perfect consensus matches at a particular base pair position. Lower case letters refer to base pair positions at which there was a less than perfect consensus match. Specifically, the code used was as follows:

| Code | Base | Meaning |
|------|------|---------|
| A | A | Adenine |
| C | C | Cytosine |
| G | G | Guanine |
| T | T | Thymine |
| U | U | Uracil (RNA) |
| R | A or G | Purine |
| Y | C or T (or U) | Pyrimidine |
| K | G or T (or U) | Keto |
| M | A or C | Amino |
| S | G or C | Strong |
| W | A or T (or U) | Weak |
| B | C, G, T (or U) | not A |
| D | G, A, T (or U) | not C |
| H | A, C, T (or U) | not G |
| V | A, C, or G | not T |
| N | A, C, G, T (or U) | Any |
| X | A, C, G, T (or U), or none | Any or none |

FIG. 3B. Alignment of L36 consensus nucleotide sequence with a mouse stearoyl-CoA desaturase nucleotide sequence (top sequence: SEQ. ID NO:2; bottom sequence: SEQ ID NO:3). It will be noted that there are two alignments listed for this L36/mouse stearoyl-CoA desaturase match. Each represents a highly statistically significant alignment, and together, these alignments represent very highly significant matches. This is the case for each of the matches listed in the figures, below, which have greater than one alignment listed.

Figures 4, 23A:
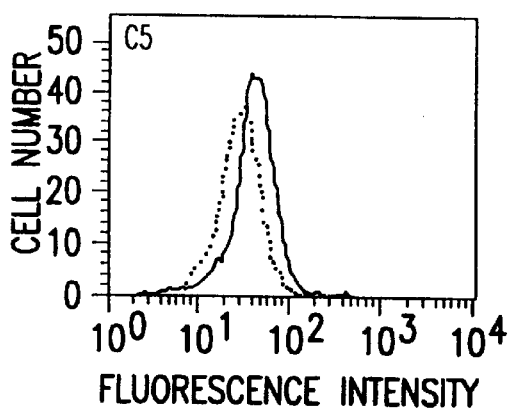

FIG. 4. Alignment of P3 consensus nucleotide sequence (top line of upper sequence pair: SEQ ID NO.:4; top line of lower sequence pair: SEQ ID NO.:39) with a mouse glutamine synthetase nucleotide sequence (bottom line of upper sequence pair: SEQ ID NO.:5; bottom line of lower sequence pair: SEQ ID NO.:6).

Figures 5, 23A:
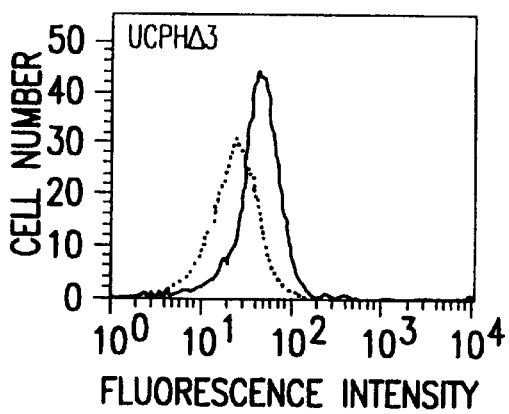

FIG. 5. Alignment of P13 consensus nucleotide sequence (top line of first sequence pair: SEQ ID NO.:7; top line of second sequence pair: SEQ ID NO.:40; top line of third sequence pair: SEQ ID NO.:41; top line of fourth sequence pair: SEQ ID NO.:42) with a mouse islet regenerating protein nucleotide sequence (bottom line of first sequence pair: SEQ NO.:8; bottom line of second sequence pair: SEQ NO.:9; bottom line of third sequence pair: SEQ NO.:10; bottom line of fourth sequence pair: SEQ NO.:11).

FIG. 6. Alignment of F5 consensus nucleotide sequence (top line of sequence pair; SEQ ID NO.:12) with a mouse alpha-amylase nucleotide sequence (bottom line of sequence pair; SEQ ID NO.:13).

FIG. 7. Alignment of murine C5 consensus nucleotide sequence (top line of sequence pair; SEQ ID NO.:14) with a rabbit uncoupling protein nucleotide sequence (bottom line of sequence pair; SEQ ID NO.:15).

FIGS. 8A, 8B. Alignment of L31/F74 consensus nucleotide sequence (top line of sequence pair; SEQ ID NO.:16) with a mouse major urinary protein II nucleotide sequence (bottom line of sequence pair; SEQ ID NO.:17).

FIG. 9. Alignment of L7/L21 consensus nucleotide sequence (top line of sequence pair; SEQ ID NO.:18) with a mouse cytochrome oxidase c subunit I nucleotide sequence (bottom line of sequence pair; SEQ ID NO.:19).

FIG. 10. Alignment of L29 consensus nucleotide sequence (top line of sequence pair; SEQ ID NO.:20) with a mouse testosterone 15-alpha hydroxylase nucleotide sequence (bottom line of sequence pair; SEQ ID NO.:21).

FIG. 11. Alignment of L38 consensus nucleotide sequence (top line of upper sequence pair: SEQ ID NO.:22; top line of lower sequence pair: SEQ ID NO.:43) with a mouse 24p3 (a lipocalin family member of unknown function) nucleotide sequence (bottom line of top sequence pair: SEQ ID NO.:23; bottom line of lower sequence pair: SEQ ID NO.:24).

FIG. 12. Alignment of L37 consensus nucleotide sequence (top line of first sequence pair: SEQ ID NO.:25; top line of second sequence pair: SEQ ID NO.:44; top line of third sequence pair: SEQ ID NO.:45) with a mouse p6-5 (a mouse sequence 86% homologous to rat preproelastase I) nucleotide sequence (bottom line of first sequence pair: SEQ ID NO.:26; bottom line of second sequence pair: SEQ ID NO.:27; bottom line of third sequence pair: SEQ ID NO.:28).

FIG. 13. Alignment of L57 consensus nucleotide sequence (top line of first sequence pair: SEQ ID NO.:29; top line of second sequence pair: SEQ ID NO.:46; top line of third sequence pair: SEQ ID NO.:47; top line of fourth sequence pair: SEQ ID NO.:48) with a mouse orphan hormone receptor nucleotide sequence (bottom line of first sequence pair: SEQ ID NO.:30; bottom line of second sequence pair: SEQ ID NO.:31; bottom line of third sequence pair: SEQ ID NO.:32; bottom line of fourth sequence pair: SEQ ID NO.:33).

FIG. 14. Full length F49 cDNA clone. A cDNA putatively encoding the full length coding sequence of the F49 gene was isolated and its nucleotide sequence is listed herein (SEQ ID NO.:34). The F49 coding sequence encodes a 96 amino acid protein whose sequence is also listed herein (SEQ ID NO.:35). The initiating methionine codon and the termination codon are boxed.

Figure 15:
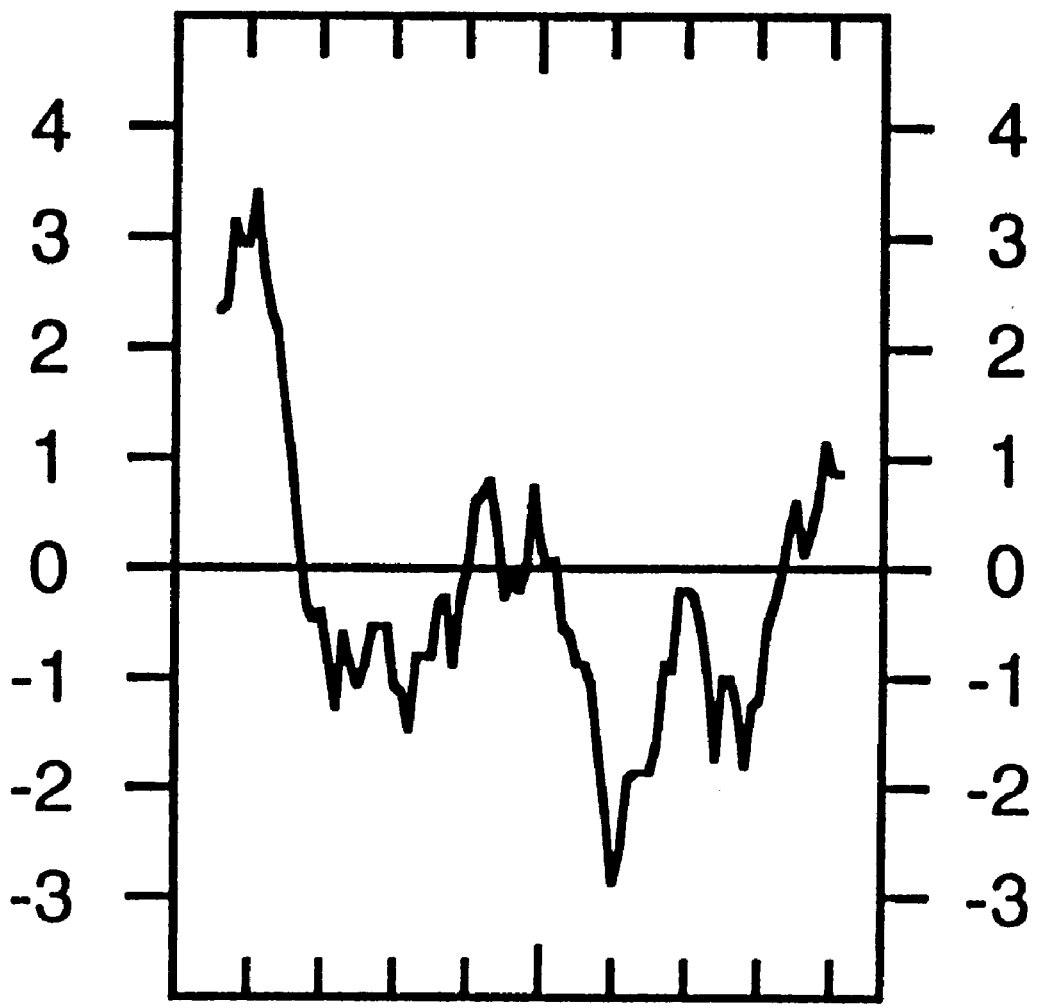

FIG. 15. Hydropathy plot of the F49 gene product.

FIGS. 16A–16B. Depicted herein are, first, the full length mouse C5 nucleotide sequence (SEQ ID NO.:36), and second, the amino acid sequence (SEQ ID NO.:37) encoded by the mouse C5 gene. The initiating methionine and the termination codon are boxed.

FIG. 17A. Comparison of the amino acid sequences of murine brown fat uncoupling protein (mUCP; SEQ ID NO.:56; Kozak C P. et al., 1988, J. Biol. Chem. 262:1274–1277) and murine C5 (referred to in the figure as mC5). Amino acid identities are indicated by lines, conservative substitutions are indicated by dots. The putative nucleotide binding sites are underlined. Alignments were performed using the ALIGN program (Myers & Miller, 1988, CABIOS 4:11–17).

FIG. 17B. Comparison of the amino acid sequences of murine C5 (referred to in the figure as mC5; SEQ ID NO.:36) and human C5 (referred to in the figure as hC5; SEQ ID NO.:51) amino acid sequences. Amino acid identities are indicated by lines, conservative substitutions are indicated by dots. The putative nucleotide binding sites are underlined. Alignments were performed using the ALIGN program (Myers & Miller, 1988, CABIOS 4:11–17).

FIGS. 18A–18B. Depicted herein are, first, the full length human C5 nucleotide sequence (SEQ ID NO.:38), and second, the human C5 gene product amino acid sequence (SEQ ID NO: 51).

Figure 19A:
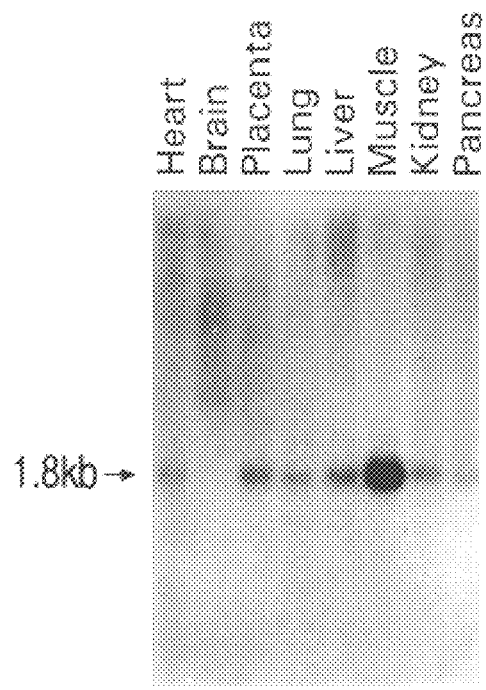

FIG. 19A. Northern analysis of tissue distribution of human C5 RNA. 2 μg poly-A+ mRNA loaded per lane 15 μg total RNA.

Figure 19B:
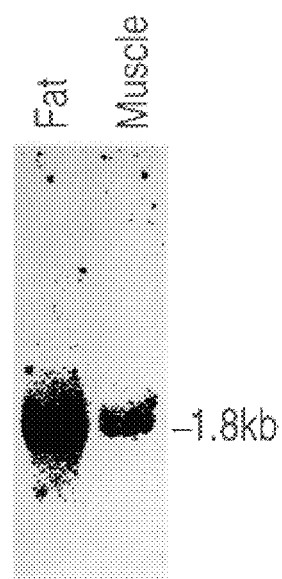

FIG. 19B. Northern analysis of tissue distribution of human C5 RNA. 15 μg total RNA loaded per lane.

FIG. 20. Alignment of H27 consensus nucleotide sequence (top line of sequence pair: SEQ ID NO: 49) with a mouse autoantigen La nucleotide sequence (bottom line of sequence pair: SEQ ID NO: 50).

FIG. 21. Alignment of F84 consensus nucleotide sequence (top line of upper sequence pair: SEQ ID NO: 52; top line of lower sequence pair: SEQ ID NO.:54) with a mouse cytochrome p450 IID nucleotide sequence (bottom line of upper sequence pair: SEQ ID NO: 53; bottom line of lower sequence pair: SEQ ID NO:55).

FIG. 22. Mouse L34 cDNA nucleotide sequence (SEQ ID NO: 57).

FIG. 23A. C5 expression in S. cerevisiae decreases the mitochondrial membrane potential. Yeast strain CKY8 containing the indicated expression constructs or vector only were stained with the potential-sensitive dye $DiOC_6$ and analyzed by FACS as described in Section 12.1. Solid lines indicate strains containing vector only, dotted lines indicate strains containing the indicated expression plasmids or a vector only strain treated with 200 μM of the chemical uncoupler CCCP.

Figures 1, 23B:
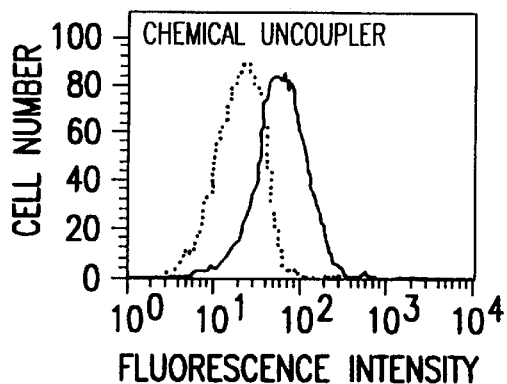
Figures 2, 23B:
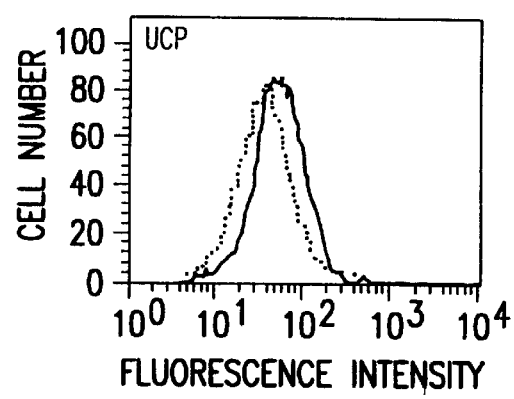
Figures 3, 23B:
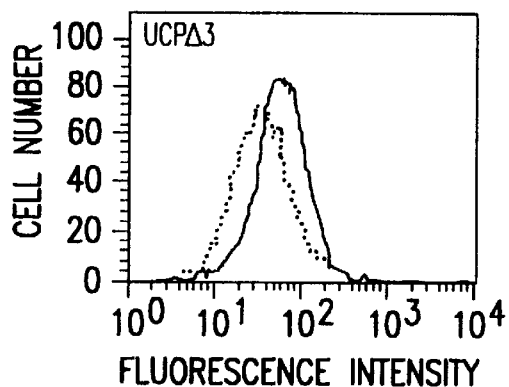
Figures 4, 23B:
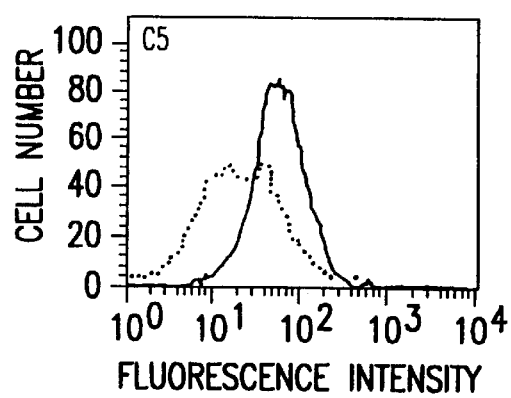
Figures 5, 23B:
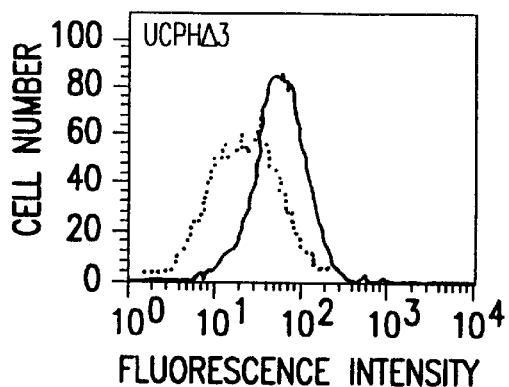

FIG. 23B. C5 expression in S. cerevisiae decreases the mitochondrial membrane potential. Yeast strain RGY12 containing the indicated expression constructs or vector only were stained with the potential-sensitive dye $DiOC_6$ and analyzed by FACS as described in Section 12.1. Solid lines indicate strains containing vector only, dotted lines indicate strains containing the indicated expression plasmids or a vector only strain treated with 200 μM of the chemical uncoupler CCCP.

5. DETAILED DESCRIPTION OF THE INVENTION

Methods and compositions are described herein for the modulation of body weight-related processes, including, for example, treatment of body weight disorders such as obesity and cachexia, and modlation of body weight and thermogenesis. Genes, termed "target genes" and/or "fingerprint genes", are described which are differentially expressed in body weight disorder states, relative to their expression in normal, or non-body weight disorder states, and/or which are differentially expressed in response to manipulations relevant to appetite and/or body weight regulation. Additionally, genes, termed "pathway genes", are described whose gene products exhibit an ability to interact with gene products involved in body weight disorders and/or with gene products which are relevant to appetite and/or body weight regulation. Methods for the identification of such fingerprint, target, and pathway genes are also described.

Further, the gene products of such fingerprint, target, and pathway genes are described, antibodies to such gene products are described, as are cell- and animal-based models of body weight disorders to which such gene products may contribute.

Described, below, are methods for the identification of compounds which modulate the expression of genes or the activity of gene products involved in body weight disorders and processes relevant to appetite and/or body weight regulation. Additionally described, below, are methods for the treatment of body weight disorders.

Also discussed, below, are methods for prognostic and diagnostic evaluation of various body weight disorders, and for the identification of subjects exhibiting a predisposition to such disorders.

5.1. IDENTIFICATION OF DIFFERENTIALLY EXPRESSED AND PATHWAY GENES

Described herein are methods for the identification of genes which are involved in body weight disorder states, and/or which are involved in appetite and body weight regulation. Such genes may represent genes which are differentially expressed in body weight disorder states relative to their expression in normal, or non-body weight disorder states. Further, such genes may represent genes which are differentially regulated in response to manipulations relevant to appetite and body weight regulation. Such differentially expressed genes may represent "target" and/or "fingerprint" genes. Methods for the identification of such differentially expressed genes are described, below, in Section 5.1.1. Methods for the further characterization of such differentially expressed genes, and for their identification as target and/or fingerprint genes, are presented, below, in Section 5.1.3.

In addition, methods are described herein, in Section 5.1.2, for the identification of genes, termed "pathway genes", involved in body weight disorder states, and/or in appetite or body weight regulation. "Pathway gene", as used herein, refers to a gene whose gene product exhibits the ability to interact with gene products involved in body weight disorders and/or to interact with gene products which are relevant to appetite or body weight regulation. A pathway gene may be differentially expressed and, therefore, may have the characteristics of a target and/or fingerprint gene.

"Differential expression" as used herein refers to both quantitative as well as qualitative differences in the genes' temporal and/or tissue expression patterns. Thus, a differentially expressed gene may qualitatively have its expression activated or completely inactivated in normal versus body weight disorder states, or under control versus experimental conditions. Such a qualitatively regulated gene will exhibit an expression pattern within a given tissue or cell type which is detectable in either control or body weight disorder subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, RT-PCR and/or Northern analyses, which are well known to those of skill in the art.

Alternatively, a differentially expressed gene may have its expression modulated, i.e., quantitatively increased or decreased, in normal versus body weight disorder states, or under control versus experimental conditions. The degree to which expression differs in normal versus body weight disorder or control versus experimental states need only be large enough to be visualized via standard characterization techniques, such as, for example, the differential display technique described below. Other such standard characterization techniques by which expression differences may be visualized include but are not limited to, quantitative RT (reverse transcriptase) PCR and Northern analyses.

Differentially expressed genes may be further described as target genes and/or fingerprint genes. "Fingerprint gene," as used herein, refers to a differentially expressed gene whose expression pattern may be utilized as part of a prognostic or diagnostic body weight disorder evaluation, or which, alternatively, may be used in methods for identifying compounds useful for the treatment of body weight disorders. A fingerprint gene may also have the characteristics of a target gene or a pathway gene.

"Target gene", as used herein, refers to a differentially expressed gene involved in body weight disorders and/or appetite or body regulation in a manner by which modulation of the level of target gene expression or of target gene product activity may act to ameliorate symptoms of body weight disorders including, but are not limited to, obesity. A target gene may also have the characteristics of a fingerprint gene and/or a pathway gene.

5.1.1. METHODS FOR THE IDENTIFICATION OF DIFFERENTIALLY EXPRESSED GENES

A variety of methods may be utilized for the identification of genes which are involved in body weight disorder states, and/or which are involved in appetite and body weight regulation. Described in Section 5.1.1.1 are several experimental paradigms which may be utilized for the generation of subjects and samples which may be used for the identification of such genes. Material from the paradigm control and experimental subjects may be characterized for the presence of differentially expressed gene sequences as discussed, below, in Section 5.1.1.2.

5.1.1.1. PARADIGMS FOR THE IDENTIFICATION OF DIFFERENTIALLY EXPRESSED GENES

Among the paradigms which may be utilized for the identification of differentially expressed genes involved in, for example, body weight disorders, are paradigms designed to analyze those genes which may be involved in short term appetite control. Accordingly, such paradigms are referred to as "short term appetite control paradigms." These paradigms may serve to identify genes involved in signalling hunger and satiety.

In one embodiment of such a paradigm, test subjects, preferably mice, may be fed normally prior to the initiation of the paradigm study, then divided into one control and two experimental groups. The control group would then be maintained on ad lib nourishment, while the first experimental group ("fasted group") would be fasted, and the second experimental group ("fasted-refed group") would initially be fasted, and would then be offered a highly palatable meal shortly before the collection of tissue samples. Each test animal should be weighted immediately prior to and immediately after the experiment. The Example presented in Section 7, below, demonstrates the use of such short term appetite paradigms to identify gene sequences which are differentially expressed in control versus fasting and versus refed animals.

Among additional paradigms which may be utilized for the identification of differentially expressed genes involved in, for example, body weight disorders, are paradigms designed to analyze those genes which may be involved genetic obesity. Accordingly, such paradigms are referred to as "genetic obesity paradigms". In the case of mice, for example, such paradigms may identify genes regulated by the ob, db, and/or tub gene products. In the case of rats, for example, such paradigms may identify genes regulated by the fatty (fa) gene product.

In one embodiment of such a paradigm, test subjects may include ob/ob, db/db, and/or tub/tub experimental mice and lean littermate control animals. Such animals would be offered normal nourishment for a given period, after which tissue samples would be collected for analysis. The Examples presented in Sections 6 and 8, below, demonstrate the use of such genetic obesity paradigms in identifying gene sequences which are differentially expressed in obese versus lean animals.

In additional embodiments, ob/ob, db/db, and/or tub/tub experimental mice and lean control animals may be utilized as part of the short term appetite control paradigms discussed above, or as part of the set point and/or drug study paradigms discussed below.

Paradigms which may be utilized for the identification of differentially expressed genes involved in body weight disorders may include paradigms designed to identify those genes which may be regulated in response to changes in body weight. Such paradigms may be referred to as "set point paradigms".

In one embodiment of such a paradigm, test subjects, preferably mice, may be fed normally prior to the initiation of the paradigm study, then divided into one control and two experimental groups. The control group would then be maintained on an ad lib diet of normal nourishment in order to calculate daily food intake. The first experimental group ("underweight group") would then be underfed by receiving some fraction of normal food intake, 60–90% of normal, for example, so as to reduce and maintain the group's body weight to some percentage, for example 80%, of the control group. The second experimental group ("overweight group") would be overfed by receiving a diet which would bring the group to some level above that of the control, for example 125% of the control group. Tissue samples would then be obtained for analysis. The Example presented in Section 9, below, demonstrates the use of such set point paradigms to identify gene sequences which are differentially expressed in control versus overweight and/or underweight conditions.

Additionally, human subjects may be utilized for the identification of obesity-associated genes. In one embodiment of such a paradigm, tissue samples may be obtained from obese and lean human subjects and analyzed for the presence of genes which are differentially expressed in the tissue of one group as opposed to another (e.g. differentially expressed in lean versus obese subjects). In another embodiment, obese human subjects may be studied over the course of a period of weight loss, achieved through food restriction. Tissue from these previously obese subjects may be analyzed for differential expression of gene products relative to tissue obtained from control (lean, non-previously obese) and obese subjects.

Paradigms may be utilized for the identification of differentially expressed genes involved in body weight disorders may additionally include paradigms designed to identify genes associated with body weight disorders induced by some physical manipulation to the test subject, such as, for example, hypothalamic lesion-induced body weight disorders. For example, bilateral lesions in the ventromedial hypothalamus (VMH) of rodents may be utilized to induce hyperphagia and gross obesity in test subjects, while bilateral lesions in the ventrolateral hypothalamus (VLH) of rodents may be utilized to induce aphagia in test subjects. In such paradigms, tissue from hypothalamic-lesioned test subjects and from control subjects would be analyzed for the identification of genes which are differentially expressed in control versus lesioned animals.

Drugs known to affect (e.g., ameliorate) human or animal body weight and/or appetite (such as short term appetite) may be incorporated into paradigms designed to identify genes which are involved in body weight disorders and/or body weight or appetite regulation. Accordingly, such paradigms are referred to as "drug study paradigms". Such compounds may include known therapeutics, as well as compounds that are not useful as therapeutics due to, for example, their harmful side effects. Among the categories of control and test subjects which may be utilized in such paradigms are, for example, lean subjects, obese subjects, and obese subjects which have received the drug of interest. In various embodiments of the paradigms, subjects such as these may be fed a normal ad lib diet, a caloric restriction maintained diet, or a caloric restriction ad lib diet. Control and test subjects may additionally be pairfed i.e., the control and test subjects may be fed via a coupled feeding device such that both control and test subjects receive identical amounts and types of food).

5.1.1.2. ANALYSIS OF PARADIGM MATERIAL

In order to identify differentially expressed genes, RNA, either total or mRNA, may be isolated from one or more tissues of the subjects utilized in paradigms such as those described, above, in Section 5.1.1. RNA samples are obtained from tissues of experimental subjects and from corresponding tissues of control subjects. Any RNA isolation technique which does not select against the isolation of mRNA may be utilized for the purification of such RNA samples. See, for example, Ausubel, F. M. et al., eds., 1987–1993, *Current Protocols in Molecular Biology,* John Wiley & Sons, Inc. New York, which is incorporated herein by reference in its entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P. and Pardee, A. B., 1992, Science 257:967–971; U.S. Pat. No. 5,262,311, which is incorporated herein by reference in its entirety), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type or tissue derived from a control subject, while the second cDNA probe may correspond to a total cell cDNA probe of the same cell type or tissue derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue or cell type, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987., U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the 3' primer type of oligonucleotide described below.

Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The 3' oligonucleotide primer of the primer pairs may contain an oligo dT stretch of 10–13, preferably 11, dT nucleotides at its 5' end, which hybridizes to the poly(A) tail of mRNA or to the complement of a cDNA reverse transcribed from an mRNA poly(A) tail. Second, in order to increase the specificity of the 3' primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer may contain a nucleotide sequence expected, statistically, to have the ability to hybridize to cDNA sequences derived from the tissues of interest. The nucleotide sequence may be an arbitrary one, and the length of the 5' oligonucleotide primer may range from about 9 to about 15 nucleotides, with about 13 nucleotides being preferred.

Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differentially expressed genes are indicated by differences in the two banding patterns.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis, quantitative RT PCR or RNase protection.

Upon corroboration, the differentially expressed genes may be further characterized, and may be identified as target and/or fingerprint genes, as discussed, below, in Section 5.1.3.

Also, amplified sequences of differentially expressed genes obtained through, for example, differential display may be used to isolate full length clones of the corresponding gene. The full length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate full length cDNA sequences. As described, above, in this Section, the isolated, amplified gene fragments obtained through differential display have 5' terminal ends at some random point within the gene and usually have 3' terminal ends at a position corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of full length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.

5.1.2. METHODS FOR THE IDENTIFICATION OF PATHWAY GENES

Methods are described herein for the identification of pathway genes. "Pathway gene", as used herein, refers to a gene whose gene product exhibits the ability to interact with gene products involved in body weight disorders and/or to interact with gene products which are relevant to appetite or body weight regulation. A pathway gene may be differentially expressed and, therefore, may have the characteristics of a target and/or fingerprint gene.

Any method suitable for detecting protein-protein interactions may be employed for identifying pathway gene products by identifying interactions between gene products and gene products known to be involved in body weight disorders and/or involved in appetite or body regulation. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for pathway gene sequences. Screening made be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of pathway genes which encode the protein interacting with a protein involved in body weight disorder states and/or appetite and body weight regulation. These methods include, for example, probing expression libraries with labeled protein known or suggested to be involved in body weight disorders and/or appetite or body weight regulation, using this protein in a manner similar to the well known technique of antibody probing of λgt11 libraries.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, in this case, a protein known to be involved in body weight disorders and or processes relevant to appetite and/or weight regulation, and the other consists of the transcription activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with a known "bait" gene product. By way of example, and not by way of limitation, gene products known to be involved in body weight disorders and/or appetite or body weight regulation may be used as the bait gene products. These include but are not limited to the intracellular domain of receptors for such hormones as neuropeptide Y, galanin, interostatin, insulin, and CCK. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait gene product are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait gene product will reconstitute an active GAL4 protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art.

Once a pathway gene has been identified and isolated, it may be further characterized as, for example, discussed below, in Section 5.1.3.

5.1.3. CHARACTERIZATION OF DIFFERENTIALLY EXPRESSED AND PATHWAY GENES

Differentially expressed genes, such as those identified via the methods discussed, above, in Section 5.1.1, and pathway genes, such as those identified via the methods discussed, above, in Section 5.1.2, above, as well as genes identified by alternative means, may be further characterized by utilizing, for example, methods such as those discussed herein. Such genes will be referred to herein as "identified genes".

Analyses such as those described herein, yield information regarding the biological function of the identified genes. An assessment of the biological function of the differentially expressed genes, in addition, will allow for their designation as target and/or fingerprint genes.

Specifically, any of the differentially expressed genes whose further characterization indicates that a modulation of the gene's expression or a modulation of the gene product's activity may ameliorate any of the body weight disorders of interest will be designated "target genes", as defined, above, in Section 5.1. Such target genes and target gene products, along with those discussed below, will constitute the focus of the compound discovery strategies discussed, below, in Section 5.3. Further, such target genes, target gene products and/or modulating compounds can be used as part of the body weight disorder treatment methods described, below, in Section 5.4.

Any of the differentially expressed genes whose further characterization indicates that such modulations may not positively affect body weight disorders of interest, but whose expression pattern contributes to a gene expression "fingerprint" pattern correlative of, for example, a body weight disorder state will be designated a "fingerprint gene". "Fingerprint patterns" will be more fully discussed, below, in Section 5.7.1. It should be noted that each of the target genes may also function as fingerprint genes, as well as may all or a portion of the pathway genes.

It should further be noted that the pathway genes may also be characterized according to techniques such as those described herein. Those pathway genes which yield information indicating that they are differentially expressed and that modulation of the gene's expression or a modulation of the gene product's activity may ameliorate any of the body weight disorders of interest will be also be designated "target genes". Such target genes and target gene products, along with those discussed above, will constitute the focus of the compound discovery strategies discussed, below, in Section 5.3 and can be used as part of the treatment methods described in Section 5.4, below.

It should be additionally noted that the characterization of one or more of the pathway genes may reveal a lack of differential expression, but evidence that modulation of the gene's activity or expression may, nonetheless, ameliorate body weight disorder symptoms. In such cases, these genes and gene products would also be considered a focus of the compound discovery strategies of Section 5.3, below.

In instances wherein a pathway gene's characterization indicates that modulation of gene expression or gene product activity may not positively affect body weight disorders of interest, but whose expression is differentially expressed and contributes to a gene expression fingerprint pattern correlative of, for example, a body weight disorder state, such pathway genes may additionally be designated as fingerprint genes.

A variety of techniques can be utilized to further characterize the identified genes. First, the nucleotide sequence of the identified genes, which may be obtained by utilizing standard techniques well known to those of skill in the art, may, for example, be used to reveal homologies to one or more known sequence motifs which may yield information regarding the biological function of the identified gene product.

Second, an analysis of the tissue and/or cell type distribution of the mRNA produced by the identified genes may be conducted, utilizing standard techniques well known to those of skill in the art. Such techniques may include, for example, Northern, RNase protection and RT-PCR analyses. Such analyses provide information as to, for example, whether the identified genes are expressed in tissues or cell types expected to contribute to the body weight disorders of interest. Such analyses may also provide quantitative information regarding steady state mRNA regulation, yielding data concerning which of the identified genes exhibits a high level of regulation in, preferably, tissues which may be expected to contribute to the body weight disorders of interest. Additionally, standard in situ hybridization techniques may be utilized to provide information regarding which cells within a given tissue express the identified gene. Such an analysis may provide information regarding the biological function of an identified gene relative to a given body weight disorder in instances wherein only a subset of the cells within the tissue is thought to be relevant to the body weight disorder.

Third, the sequences of the identified genes may be used, utilizing standard techniques, to place the genes onto genetic maps, e.g., mouse (Copeland, N. G. and Jenkins, N. A., 1991, Trends in Genetics 7:113–118) and human genetic maps (Cohen, D., et al., 1993, Nature 366:698–701). Such mapping information may yield information regarding the genes' importance to human disease by, for example, identifying genes which map within genetic regions to which known genetic body weight disorders map.

Fourth, the biological function of the identified genes may be more directly assessed by utilizing relevant in vivo and in vitro systems. In vivo systems may include, but are not limited to, animal systems which naturally exhibit body weight disorder-like symptoms, or ones which have been engineered to exhibit such symptoms. Further, such systems may include systems for the further characterization of body weight disorders, and/or appetite or body weight regulation, and may include, but are not limited to, naturally occurring and transgenic animal systems such as those described, above, in Section 5.1.1.1, and Section 5.2.4.1, below. In vitro systems may include, but are not limited to, cell-based systems comprising cell types known or suspected of contributing to the body weight disorder of interest. Such cells may be wild type cells, or may be non-wild type cells containing modifications known to, or suspected of, contributing to the body weight disorder of interest. Such systems are discussed in detail, below, in Section 5.2.4.2.

In further characterizing the biological function of the identified genes, the expression of these genes may be modulated within the in vivo and/or in vitro systems, i.e., either overexpressed or underexpressed in, for example, transgenic animals and/or cell lines, and its subsequent effect on the system then assayed. Alternatively, the activity of the product of the identified gene may be modulated by either increasing or decreasing the level of activity in the in vivo and/or in vitro system of interest, and its subsequent effect then assayed.

The information obtained through such characterizations may suggest relevant methods for the treatment of body weight disorders involving the gene of interest. Further, relevant methods for the control of appetite and body weight regulation involving the gene of interest may be suggested by information obtained from such characterizations. For example, treatment may include a modulation of gene expression and/or gene product activity. Characterization procedures such as those described herein may indicate where such modulation should involve an increase or a decrease in the expression or activity of the gene or gene product of interest. Such methods of treatment are discussed, below, in Section 5.4.

5.2. DIFFERENTIALLY EXPRESSED AND PATHWAY GENES

Identified genes, which include, but are not limited to, differentially expressed genes such as those identified in Section 5.1.1, above, and pathway genes, such as those identified in Section 5.1.2, above, are described herein. Specifically, the nucleic acid sequences and gene products of such identified genes are described. Further, antibodies directed against the identified genes' products, and cell- and animal-based models by which the identified genes may be further characterized and utilized are also discussed in this Section.

5.2.1. DIFFERENTIALLY EXPRESSED GENE SEQUENCES

Differentially expressed nucleotide sequences are shown in FIGS. 3A, 4–14, 16A–16B, 18A–18B and 20–22. Table 1 lists differentially expressed genes (P3, P13, F5, F49, murine C5, human C5, L31/F74, L7/L21, L29, L38, L37, L57, H27, F84 and L34) identified and characterized through, for example, the paradigms discussed, above, in Section 5.1.1.1, and, below, in the examples presented in Sections 6–12. Table 1 also summarizes information regarding the further characterization of such genes. Table 2 lists *E. coli* clones, deposited with the Agricultural Research Service Culture Collection (NRRL) or American Type Culture Collection (ATCC), which contain sequences found within the F49 and human C5 genes listed in Table 1.

In Table 1, the differential expression patterns revealed via, for example, one or more of the paradigm conditions described in Section 5.1.1.1, above, are summarized under the column headed "Paradigm Expression Pattern". For each of the tested genes, the paradigm which was used and the difference in the expression of the gene in experimental versus control tissues is shown. "o" indicates that gene expression is increased (i.e., there is an increase in the amount of detectable mRNA produced by a given gene) in experimental versus control tissue or cell type, while "l" indicates that gene expression is decreased (i.e., there is an decrease in the amount of detectable mRNA produced by a given gene) in experimental versus control tissue or cell type. Further, "+" indicates that gene expression is activated in experimental versus control tissue or cell type, i.e., mRNA is detectable in experimental tissue or cell type whereas none is detectable in control tissue or cell type, while "−" would indicate that gene expression is inactivated in experimental versus control tissue or cell type, i.e., while mRNA is detectable in control tissue or cell type, it is no longer detectable in experimental tissue or cell type. "Detectable" as used herein, refers to levels of mRNA which are detectable via standard differential display, Northern and/or RT-PCR techniques which are well known to those of skill in the art. "Increased" and "decreased", as used herein, refer to an increase or decrease, respectively in level of mRNA present in experimental versus control tissue or cell type which is detectable via standard differential display, Northern, and/or RT-PCR techniques which are well known to those of skill in the art.

Tissue expression patterns are also summarized in Table 1. The column headed "First Detection" indicates the first tissue or cell type in which differential expression of the gene was detected. The column headed "Tissue/Cell Dist." lists tissues and/or cell types in which expression of the gene has been tested and whether expression of the gene within a given tissue or cell type has been observed. Specifically, "+" indicates detectable mRNA from the gene of interest, while "−" refers to no detectable mRNA from the gene of interest. Unless otherwise noted, "+" and "−" refer to both control and experimental samples. "Detectable", as used herein, is as defined earlier in this Section. The expression patterns of the murine and human C5 genes are described in the Examples presented, below, in Sections 10 and 11, respectively.

Additionally, the physical locus to which the gene maps on the human and/or mouse chromosome map is indicated in the column headed "Locus". Further, in instances wherein the genes correspond to genes known to be found in nucleic acid databases, references (i.e., citations and/or gene names) to such known genes are listed in the column headed "Ref".

The genes listed in Table 1 can be obtained using cloning methods well known to those of skill in the art, and which include, but are not limited to, the use of appropriate probes to detect the genes within an appropriate cDNA or gDNA (genomic DNA) library. (See, for example, Sambrook et al., 1989, Molecular Cloning: A Laboratory Manual, Cold Spring Hanson Laboratories, which is incorporated herein by reference in its entirety.) Probes for the sequences reported herein can be obtained directly from the isolated clones deposited with the NRRL, as indicated in Table 2, below. Alternatively, oligonucleotide probes for the genes can be synthesized based on the DNA sequences disclosed herein in FIGS. 3A, 4–14, 16A–16B, 18A–18B and 20–22. With respect to the previously reported genes, oligonucleotides can be synthesized or produced based on the sequences provided for the previously known genes described in the following references: glutamine synthetase (P3): Bhandari et al., 1991, J. Biol. Chem. 266:7784–7792; islet regenerating protein (P13): Unno, M. et al., 1987, J. Biol. Chem. 268:15974–15982; Terazono, K. et al., 1988, J. Biol. Chem. 263:2111–2114; Watanabe, T., 1990, J. Biol. Chem. 265:7432–7439; alpha amylase (F5): Schibler, U. et al., 1986, in "Oxford Surveys on Eukaryotic Genes", Maclean, N., ed. 3:210, Oxford Univ. Press, New York; Schibler et al., 1982, J. Mol. Biol. 155:247–266; mouse major urinary protein II (L31/F74): Shahan, K. et al., 1987, Mol. Cell. Biol. 1:1938–1946; mouse cytochrome C oxidase Subunit I (L7/L21): Bibb et al., 1981, Cell 26:167–180; mouse testosterone 15-alpha hydroxylase (L15): Squires, E. J. and Negism:, M., 1988, J. Biol. Chem. 263:4166–4171; mouse 24p3 (L38): Flower, D. R. et al., 1991, Biochem. Biophys. Res. Comm. 180:69–74; Hraba-Renevey, S. et al., 1989, Oncogene 4:601–608; mouse p6-5 (L37): Yamasaki, N. et al., 1987, Eur. J. Immunol. 17:247–253; mouse orphan nuclear hormone receptor (L57) Forman et al., 1994, Mol. Endocrinol. 81253–1261; autoantigen La (H27): Genbank Accession No. L00993; and mouse cytochrome p450 IID (F84): Matsunaga, E. et al., 1990, J. Mol. Evol. 30:155–169; mouse L34 (homolog of the human lrp 130 gene): Hou, J. et al., 1994, In Vitro Cell. Dev. Biol. Anim. 30A:111–114.

The probes can be used to screen cDNA libraries prepared from an appropriate cell, cell line or tissue in which the gene is transcribed. Appropriate cell lines can include, for example, preadipocyte cell lines such as 3T3-A1 and TA1 mouse preadipocyte cell lines, liver cell lines, such as the Hepa1-6 mouse liver cell line and the HepG2 human liver cell line.

TABLE 1

Differentially Expressed Genes

| Gene | Paradigm Expression Pattern | First Detection | Tissue/Cell Dist. | Locus | Ref |
|---|---|---|---|---|---|
| P3 (SEQ. ID NO:4, 39) | ⇑Pancreas (fasted) | Pancreas | | | 1 |
| P13 (SEQ. ID NO:7, 40–42) | ⇑Pancreas (fasted) | Pancreas | | | 2 |
| F5 (SEQ. ID NO:12) | ⇑Adipose (fasted) | Adipose | | | 3 |
| F49 (SEQ. ID NO:34) | +Adipose (db/db) | Adipose | Adipose [(+) db/db; (–) lean control] Muscle (–) Small Intestine (–) Hypothalamus (–) Liver (–) Pancreas (–) | Chrom 2 | |
| murine C5[10] (SEQ. ID NO: 36) | ⇑Adipose (ob/ob and db/db) | Adipose | See Section 10 | | |
| L31/F74 (SEQ. ID NO:16) | ↓Liver and Adipose (ob/ob and db/db) ↓Liver (underweight) | Adipose; Liver | Liver (+) Adipose (+) Muscle (–) | | 4 |
| L7/L21 (SEQ. ID NO:18) | ⇑Liver (fasted, ob/ob, and db/db) | Liver | | | 5 |
| L29 (SEQ. ID NO:20) | ↓Liver (ob/ob) | Liver | | | 6 |
| L38 (SEQ. ID NO:22, 43) | ⇑Liver (ob/ob and db/db) | Liver | | | 7 |
| L37 (SEQ. NO:25, 44–45) | ⇑Liver (ob/ob) | Liver | | | 8 |
| L57 (SEQ. ID NO:29, 46–48) | ⇑Liver (underweight) | Liver | | | 9 |

TABLE 1-continued

Differentially Expressed Genes

| Gene | Paradigm Expression Pattern | First Detection | Tissue/ Cell Dist. | Locus | Ref |
|---|---|---|---|---|---|
| Human C5 (SEQ ID NO.:38) | | | See Section 11 | | |
| H27 (SEQ ID NO: 49) | ↓Hypothalamus (fasted) | Hypothalamus | | | 11 |
| F84 (SEQ ID NO: 52, 54) | ↓Adipose (underweight) | Adipose | | | 12 |
| L34 (SEQ ID NO:57) | ↑Liver (ob/ob) | Liver | | | 13 |

[1] Mouse glutamine synthetase: Bhandari et al., 1991, J. Biol. Chem. 266:7784–7792.
[2] Mouse islet regenerating protein: Unno, M. et al., 1993, J. Biol. Chem. 268:15974–15982.
[3] Mouse α-amylase: Schibler, U. et al., 1986, in "Oxford Surveys on Eukaryotic Genes", Maclean, N., ed., 3:210, Oxford Univ. Press, New York; Schibler et al., 1982, J. Mol. Biol. 155:247–266.
[4] Mouse major urinary protein II: Shahan, K. et al., 1987, Mol. Cell. Biol. 7:1938–1946.
[5] Mouse cytochrome C oxidase Subunit I: Raikhinstein, M. and Hankoglu, I., 1993, Proc. Natl. Acad. Sci. USA 90:10509–10513; Bibb et al., 1981, Cell 26:167–180.
[6] Mouse testosterone 15-α hydroxylase: Squires, E. J. and Negishi, M., 1988, J. Biol. Chem. 263:4166–4171.
[7] Mouse 24p3: Flower, D. R. et al., 1991, Biochem. Biophys. Res. Comm. 180:69–74; Hraba-Renevey, S. et al., 1989, Oncogene 4:601–608.
[8] Mouse p6-5: Yamasaki, N. et al., 1987, Eur. J. Immunol. 17:247–253.
[9] Mouse orphan nuclear hormone receptor: Forman et al., 1994, Mol. Endocrinol. 8:1253–1261.
[10] The mouse C5 sequence was first identified via sequence homology, as described in the Example presented, below, in Section 10. C5 was then subsequently tested in ob and db mice, at which time it was identified to represent a differentially expressed gene sequence.
[11] Mouse autoantigen La: Genbank Accession No. L00993.
[12] Mouse cytochrome p450 IID: Matsunaga, E. et al., 1990, J. Mol. Evol. 30:155–169.
[13] The mouse L34 gene represents the mouse homolog of the human lrp 130 gene: Hou, J. et al., 1994, In Vitro Cell. Dev. Biol. Anim. 30A:111–114.

TABLE 2

| GENE | cDNA CLONE |
|---|---|
| F49 | famf049a |
| human C5 | fahs005a |
| human C5 | fahs005a2 |

As used herein, "differentially expressed gene" (i.e. target and fingerprint gene) or "pathway gene" refers to (a) a gene containing: at least one of the DNA sequences disclosed herein (as shown in FIGS. 3A, 4–14, 16A–16B, 18A–18B and 20–22), or contained in the clones listed in Table 2, as deposited with the NRRL or ATCC; (b) any DNA sequence that encodes the amino acid sequence encoded by: the DNA sequences disclosed herein (as shown in FIGS. 3A, 4–14, 16A–16B, 18A–18B and 20–22), contained in the clones listed in Table 2, as deposited with the NRRL or ATCC, or contained within the coding region of the gene to which the DNA sequences disclosed herein (as shown in FIGS. 3A, 4–14, 16A–16B, 18A–18B and 20–22) or contained in the clones listed in Table 2, as deposited with the NRRL or ATCC, belong; (c) any DNA sequence that hybridizes to the complement of: the coding sequences disclosed herein (as shown in FIGS. 3A, 4–14, 16A–16B, 18A–18B and 20–22), contained in clones listed in Table 2, as deposited with the NRRL or ATCC, or contained within the coding region of the gene to which the DNA sequences disclosed herein (as shown in FIGS. 3A, 4–14, 16A–16B, 18A–18B and 20–22) or contained in the clones listed in Table 2, as deposited with the NRRL or ATCC, belong, under highly stringent conditions, e.g., hybridization to filter-bound DNA in 0.5 M $NaHPO_4$, 7% sodium dodecyl sulfate (SDS), 1 mM EDTA at 65°, and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3); and/or (d) any DNA sequence that hybridizes to the complement of: the coding sequences disclosed herein, (as shown in FIGS. 3A, 4–14, 16A–16B, 18A–18B and 20–22) contained in the clones listed in Table 2, as deposited with the NRRL or ATCC, or contained within the coding region of the gene to which DNA sequences disclosed herein (as shown in FIGS. 3A, 4–14, 16A–16B, 18A–18B and 20–22) or contained in the clones, listed in Table 2, as deposited with the NRRL or ATCC, belong, under less stringent conditions, such as moderately stringent conditions, e.g., washing in 0.2×SSC/0.1% SDS at 42° C. (Ausubel et al., 1989, supra), and encodes a gene product, functionally equivalent to a gene product encoded by a gene of (a), above.

"Functionally equivalent", as utilized herein, refers to a gene product which retains at least one of the biological functions or activities of the native gene product, such as, for example, a gene product capable of exhibiting a substantially similar in vivo activity as the endogenous differentially expressed or pathway gene products encoded by the differentially expressed or pathway gene sequences described in Section 5.2.1, above. Taking the C5 gene product as an example, a functionally equivalent C5 gene product is one which retains an uncoupling activity or property.

As used herein, a differentially expressed or pathway gene may also refer to fragments and/or degenerate variants of DNA sequences (a) through (d), especially naturally occurring variants thereof.

With respect to C5 genes, preferred embodiments of such genes encode C5 gene products which exhibit greater than 17–31% amino acid identity, averaged throughout the gene product's entire length, with the human or murine C5 amino acid sequences depicted in FIGS. 16A–16B and 18A–18B, respectively. In most preferred embodiments, C5 genes encode C5 gene products which exhibit a greater than 56–60% amino acid identity, averaged throughout the gene product's entire length, with the human or murine C5 amino acid sequences depicted in FIGS. 16A–16B and 18A–18B, respectively.

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as target gene antisense molecules, useful, for example, in target gene regulation and/or as antisense primers in amplification reactions of target, fingerprint, and/or pathway gene nucleic acid sequences.

Further, such sequences may be used as part of ribozyme and/or triple helix sequences, also useful for target gene regulation. Still further, such molecules may be used as components of diagnostic methods whereby the presence of, or predisposition to, a body weight disorder, may be detected.

The invention also encompasses (a) DNA vectors that contain any of the foregoing coding sequences and/or their complements (e.g., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include, but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, the promoters of yeast α-mating factors, and mammalian tissue and/or cell type specific promoters such as, e.g., the AP2 promoter.

The invention includes fragments of any of the DNA sequences disclosed and described herein. Among such fragments are C5 gene fragments, wherein such fragments encode C5 gene products lacking between one and nine of amino acid residues 267–272 depicted in FIGS. 16A–16B and 18A–18B.

In addition to the gene sequences described above, homologues of these gene sequences as may, for example, be present in other species, preferably human in instances wherein the above-described gene sequences are not human gene sequences, may be identified and isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, an isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

Further, a previously unknown differentially expressed or pathway gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed or pathway gene allele. The PCR product may be subcloned and sequenced to insure that the amplified sequences represent the sequences of a differentially expressed or pathway gene-like nucleic acid sequence.

The PCR fragment may then be used to isolate a full length cDNA clone by a variety of methods. For example, the amplified fragment may be used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

In cases where the differentially expressed or pathway gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to body weight disorder symptoms. Mutant alleles and mutant allele products may then be utilized in the therapeutic and diagnostic assay systems described below.

A cDNA of the mutant gene may be isolated, for example, by using PCR, a technique which is well known to those of skill in the art. In this case, the first cDNA strand may be synthesized by hybridizing a oligo-dT oligonucleotide to mRNA isolated from tissue known to, or suspected of, being expressed in an individual putatively carrying the mutant allele, and by extending the new strand with reverse transcriptase. The second strand of the cDNA is then synthesized using an oligonucleotide that hybridizes specifically to the 5'-end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probe to identify the corresponding mutant allele in the library. The clone containing this gene may then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.2.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

5.2.2. DIFFERENTIALLY EXPRESSED AND PATHWAY GENE PRODUCTS

Differentially expressed and pathway gene products include those proteins encoded by the differentially expressed and pathway gene sequences described in Section 5.2.1, above, as for example, the peptides listed in FIGS. 14 (SEQ ID NO: 34), 16A–16B (SEQ ID NO: 36) and 18A–18B (SEQ ID NO: 51).

In addition, differentially expressed and pathway gene products may include proteins that represent functionally equivalent gene products.

A functionally equivalent differentially expressed or pathway gene product may contain deletions, additions or substitutions of amino acid residues within the amino acid sequence encoded by the differentially expressed or pathway gene sequences described, above, in Section 5.2.1, but which result in a silent change, thus producing a functionally equivalent differentially expressed or pathway gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a gene product which retains at least one of the biological functions or activities of the native gene product, such as, for example, a gene product capable of exhibiting a substantially similar in vivo activity as the endogenous differentially expressed or pathway gene products encoded by the differentially expressed or pathway gene sequences described in Section 5.2.1, above. Taking the C5 gene product as an example, a functionally equivalent C5 gene product is one which retains an uncoupling activity or property.

Alternatively, when utilized as part of assays such as those described, below, in Section 5.3, "functionally equivalent" may refer to peptides capable of interacting with other cellular or extracellular molecules in a manner substantially similar to the way in which the corresponding portion of the endogenous differentially expressed or pathway gene product would.

The differentially expressed or pathway gene products may be produced by recombinant DNA technology using techniques well known in the art. Thus, methods for preparing the differentially expressed or pathway gene polypeptides and peptides of the invention by expressing nucleic acid encoding differentially expressed or pathway gene sequences are described herein. Methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. which is incorporated by reference herein in their entirety, and Ausubel, 1989, supra. Alternatively, RNA capable of encoding differentially expressed or pathway gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed or pathway gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g. Saccharomyces, Pichia) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the E. coli expression vector pUR278 (Ruther et al., 1983, EMBO J. 2:1791), in which the differentially expressed or pathway gene protein coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned Target gene protein can be released from the GST moiety.

In an insect system, Autographa californica nuclear polyhedrosis virus (AcNPV) is used as a vector to express foreign genes. The virus grows in Spodoptera frugiperda cells. The differentially expressed or pathway gene coding sequence may be cloned individually into non-essential regions (for example the polyhedrin gene) of the virus and placed under control of an AcNPV promoter (for example the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al.; 1983, J. Viol. 46:584; Smith, U.S. Pat. No. 4,215,051).

In mammalian host cells, a number of viral-based expression systems may be utilized. In cases where an adenovirus is used as an expression vector, the differentially expressed or pathway gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts. (e.g., See Logan & Shenk, 1984, Proc. Natl. Acad. Sci. USA 81:3655–3659). Specific initiation signals may also be required for efficient translation of inserted differentially expressed or pathway gene coding sequences. These signals include the ATG initiation codon and adjacent sequences. In cases where an entire differentially expressed or pathway gene, including its own initiation codon and adjacent sequences, is inserted into the appropriate expression vector, no additional translational control signals may be needed. However, in cases where only a portion of the differentially expressed or pathway gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively.

Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

When used as a component in assay systems such as those described herein, the differentially expressed or pathway gene protein may be labeled, either directly or indirectly, to facilitate detection of a complex formed between the differentially expressed or pathway gene protein and a test substance. Any of a variety of suitable labeling systems may be used including but not limited to radioisotopes such as $^{125}$I; enzyme labelling systems that generate a detectable colorimetric signal or light when exposed to substrate; and fluorescent labels.

Where recombinant DNA technology is used to produce the differentially expressed or pathway gene protein for such assay systems, it may be advantageous to engineer fusion proteins that can facilitate labeling, immobilization and/or detection.

Fusion proteins which facilitate solubility can include, but are not limited to soluble Ig-tailed fusion proteins. Methods for engineering such soluble Ig-tailed fusion proteins are well known to those of skill in the art. See, for example, U.S. Pat. No. 5,116,964, which is incorporated herein by reference in its entirety.

Indirect labeling involves the use of a protein, such as a labeled antibody, which specifically binds to a differentially expressed or pathway gene product. Such antibodies include but are not limited to polyclonal, monoclonal, chimeric, single chain, Fab fragments and fragments produced by an Fab expression library.

5.2.3. ANTIBODIES SPECIFIC FOR DIFFERENTIALLY EXPRESSED OR PATHWAY GENE PRODUCTS

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity. Thus, such antibodies may be utilized as part of body weight disorder treatment methods, and/or may be used as part of diagnostic techniques whereby patients may be tested for abnormal levels of fingerprint, target, or pathway gene proteins, or for the presence of abnormal forms of the such proteins.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.2.4. CELL-, IN VITRO AND ANIMAL-BASED MODEL SYSTEMS

Described herein are cell-, in vitro and animal-based systems which act as models for body weight disorders and thermogenesis. These systems may be used in a variety of applications. For example, the animal-based model systems can be utilized to identify differentially expressed genes via one of the paradigms described, above, in Section 5.1.1.1. The model systems may be used to further characterize differentially expressed and pathway genes, as described, above, in Section 5.1.3. Such further characterization may, for example, indicate that a differentially expressed gene is a target gene.

Second, such assays may be utilized as part of screening strategies designed to identify compounds which are capable of ameliorating body weight disorder symptoms, and/or modulating thermogenesis in mammals, as described, below. Amelioration of body weight disorder symptoms can itself be brought about via regulation of thermogenesis by, for example, an increase in the expression and/or activity of the C5 gene or gene product.

The model systems, therefore, can be used to identify drugs, pharmaceuticals, therapies and interventions which may be effective in modulating thermogenesis, and/or in treating body weight disorders including but not limited to obesity and cachexia, via, for example, a regulation of thermogenesis. In addition, as described in detail, below, in Section 5.5, such animal models may be used to determine the $LD_{50}$ and the $ED_{50}$ in animal subjects, and such data can be used to determine the in vivo efficacy of potential body weight disorder treatments.

5.2.4.1. ANIMAL-BASED SYSTEMS

Animal-based model systems for the study of body weight disorders may include, but are not limited to, non-recombinant and engineered transgenic animals.

Non-recombinant animal models for the study of body weight disorders may include, for example, genetic models. Such genetic body disorder models may include, for example, mouse models of obesity such as mice homozygous for the autosomal recessive ob, db, or tub alleles.

Non-recombinant, non-genetic animal models of body weight disorders may include, for example, rat models in which bilateral lesions exist in the ventromedial hypothalamus, leading to hyperphagia and gross obesity, or in which ventrolateral hypothalamus lesions exist, which lead to aphagia. Further, mice which, as newborns, are fed mono-sodium-glutamate (MSG) develop obesity, and may, therefore, also be utilized as animal models for body weight disorders.

Additionally, animal models for studying body weight disorders, such as, for example, animal models exhibiting body weight disorder-like symptoms, may be engineered by utilizing, for example, target gene sequences such as those described, above, in Section 5.2, in conjunction with techniques for producing transgenic animals that are well known to those of skill in the art. For example, target gene sequences may be introduced into, and overexpressed in, the genome of the animal of interest, or, if endogenous target gene sequences are present, they may, either be overexpressed or, alternatively, may be disrupted in order to underexpress or inactivate target gene expression.

In order to overexpress a target gene sequence, the coding portion of the target gene sequence may be ligated to a regulatory sequence which is capable of driving gene expression in the animal and cell type of interest. Such regulatory regions will be well known to those of skill in the art, and may be utilized in the absence of undue experimentation.

Taking the C5 gene as an example, a C5 gene sequence can be overexpressed in animals within cell types of interest without resorting to undue experimentation. For example, muscle and adipose tissue are among the tissues which express the C5 gene, as demonstrated in the Examples presented in Section 10 and 11, below. Regulatory sequences (e.g., promoter/enhancer sequences) capable of selectively driving expression in muscle and adipose tissue are well known to those of ordinary skill in the art. Such sequences include, but are not limited to, aP2 promoter sequences, which drive adipose tissue-specific expression (see, e.g., Kopecky, J. et al., 1995, J. Clin. Invest. 96:2914–2923). Recombinant C5 gene sequences, therefore, can be overexpressed in adipose tissue, for example, via aP2 promoter sequences to which they have been ligated in a manner that drives C5 expression.

For underexpression of an endogenous target gene sequence, such a sequence may be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, squirrels, monkeys, and chimpanzees may be used to generate body weight disorder animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. (See, for example, techniques described by Jakobovits, 1994, Curr. Biol. 4: 761–763). The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89:6232– 6236). The regulatory sequences required for such a cell-type specific activation will depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene may also be selectively introduced into a particular cell type, thus inactivating the endogenous gene of interest in only that cell type, by following, for example, the teaching of Gu et al.

(Gu, H. et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant target gene and protein may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene gene product of interest.

The target gene transgenic animals that express target gene mRNA or target gene transgene peptide (detected immunocytochemically, using antibodies directed against target gene product epitopes) at easily detectable levels should then be further evaluated to identify those animals which display characteristic body weight disorder-like symptoms. Such symptoms may include, for example, obesity, anorexia, and an abnormal food intake. Additionally, specific cell types within the transgenic animals may be analyzed and assayed for cellular phenotypes characteristic of body weight disorders. Such cellular phenotypes may include, for example, abnormal adipocyte differentiation (e.g., abnormal preadipocyte/adipocyte differentiation) and metabolism and/or abnormal uncoupling of oxidative phosphorylation. Further, such cellular phenotypes may include as assessment of a particular cell type's fingerprint pattern of expression and its comparison to known fingerprint expression profiles of the particular cell type in animals exhibiting body weight disorders. Such transgenic animals serve as suitable model systems for body weight disorders.

Once target gene transgenic founder animals are produced (i.e., those animals which express target gene proteins in cells or tissues of interest, and which, preferably, exhibit symptoms of body weight disorders), they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of body weight disorder-like symptoms. One such approach is to cross the target gene transgenic founder animals with a wild type strain to produce an F1 generation that exhibits body weight disorder-like symptoms, such as obesity, anorexia, abnormal food intake and/or abnormal uncoupling of oxidative phosphorylation. The F1 generation may then be inbred in order to develop a homozygous line, if it is found that homozygous target gene transgenic animals are viable.

5.2.4.2. CELL-BASED ASSAYS

Cells that contain and express target gene sequences which encode target gene protein, and, further, exhibit cellular phenotypes associated with a body weight disorder of interest, may be utilized to identify compounds that exhibit an ability to ameliorate body weight disorder symptoms. Cellular phenotypes which may indicate an ability to ameliorate body weight disorders may include, for example, inhibition of adipose cell differentiation (e.g., an inhibition of differentiation of preadipocytes into adipocytes), an inhibition of the ability of adipocytes to synthesize fat and/or abnormal uncoupling of oxidative phosphorylation.

Further, the fingerprint pattern of gene expression of cells of interest may be analyzed and compared to the normal, non-body weight disorder fingerprint pattern. Those compounds which cause cells exhibiting body weight disorder-like cellular phenotypes to produce a fingerprint pattern more closely resembling a normal fingerprint pattern for the cell of interest may be considered candidates for further testing regarding an ability to ameliorate body weight disorder symptoms.

Cells which can be utilized for such assays may, for example, include non-recombinant cell lines, such as preadipocyte cell lines such as 3T3-L1 and TA1 mouse preadipocyte cell lines, liver cell lines, such as the Hepa1-6 mouse liver cell line, and the HepG2 human liver cell line.

Further, cells which may be used for such assays may also include recombinant, transgenic cell lines. For example, the body weight disorder animal models of the invention, discussed, above, in Section 5.2.4.1, may be used to generate cell lines, containing one or more cell types involved in body weight disorders, that can be used as cell culture models for this disorder. While primary cultures derived from the body weight disorder transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Alternatively, cells of a cell type known to be involved in body weight disorders may be transfected with sequences capable of increasing or decreasing the amount of target gene expression within the cell. For example, target gene sequences may be introduced into, and overexpressed in, the genome of the cell of interest, or, if endogenous target gene sequences are present, they may either be overexpressed or, alternatively, be disrupted in order to underexpress or inactivate target gene expression.

In order to overexpress a target gene sequence, the coding portion of the target gene sequence may be ligated to a regulatory sequence which is capable of driving gene expression in the cell type of interest. Such regulatory regions will be well known to those of skill in the art, and may be utilized in the absence of undue experimentation.

Taking the C5 gene as an example, a C5 gene sequence can be overexpressed in cell types of interest without resorting to undue experimentation. For example, muscle and adipose cells are among the cells which express the C5 gene, as demonstrated in the Examples presented in Section 10 and 11, below. Regulatory sequences (e.g., promoter/enhancer sequences) capable of selectively driving expression in muscle and adipose cells are well known to those of ordinary skill in the art. Such sequences include, but are not limited to, aP2 promoter sequences, which drive adipose tissue-specific expression (see, e.g., Kopecky, J. et al., 1995, J. Clin. Invest. 96:2914–2923). Recombinant C5 gene sequences, therefore, can be overexpressed in adipose cells, for example, via aP2 promoter sequences to which they have been ligated in a manner that drives C5 expression.

For underexpression of an endogenous target gene sequence, such a sequence may be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Gene targeting is discussed, above, in Section 5.4.2.1.

Transfection of target gene sequence nucleic acid may be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques may be used to demonstrate whether a decrease in endogenous target gene expression and/or in target gene product production is achieved.

Cell-based systems can be utilized to study biochemical processes which affect body weight regulation and body weight disorders. For example, cell-based assays can be utilized to study, e.g., identify compounds which modulate, uncoupling of oxidative phosphorylation as is, for example, associated with thermogenesis.

For example, yeast systems and assays can be utilized as models for uncoupling of oxidative phosphorylation. Such yeast systems express C5 gene sequences as, for example, described in the Example presented in Section 12, below. Uncoupling assays can be, for example, such as those described in Section 12 and in Murdza-Inglis, D. L. et al., 1994, J. Biol. Chem. 260:7435–7438; and Murdza-Inglis, D. L. et al., 1991, J. Biol. Chem. 260:11871–11875, both of which are incorporated herein by reference in their entirety.

In addition, mammalian cells expressing C5 gene sequences, including but not limited to recombinant C5 gene sequences, can also be utilized as models for uncoupling of oxidative phosphorylation. Assays for oxidative phosphorylation can, for example, include dye-based assays such as those discussed above.

In vitro systems can include, for example, ones which utilize purified or partially purified target gene product in a manner whereby the target gene product exhibits at least one of its biological properties. Taking the C5 gene product as an example, natural or recombinant gene product can be purified or partially purified using standard polypeptide expression and/or purification procedures well known to those of skill in the art. Uncoupling activity biological properties of the C5 gene product can be assayed using, for example, dye-based assays such as those discussed above.

The C5 in vitro system can be utilized, for example, in high throughput procedures for the identification of compounds which modulate (e.g., stimulate or inhibit) C5 uncoupling activity. Among the assays which can be utilized for compound identification in conjunction with such an in vitro system are, for example, ones such as those described in Murdza-Inglis, D. L. et al., 1994, J. Biol. Chem. 260:7435–7438 and Murdza-Inglis, D. L. et al., 1991, J. Biol. Chem. 260:11871–11875.

5.3. SCREENING ASSAYS FOR COMPOUNDS THAT INTERACT WITH THE TARGET GENE PRODUCT

The following assays are designed to identify compounds that bind to target gene products, bind to other cellular proteins that interact with a target gene product, and to compounds that interfere with the interaction of the target gene product with other cellular proteins. Such compounds may include, but are not limited to, other cellular proteins. Methods for the identification of such cellular proteins are described, below, in Section 5.3.2.

Compounds may include, but are not limited to, peptides such as, for example, soluble peptides, including but not limited to, Ig-tailed fusion peptides, comprising extracellular portions of target gene product transmembrane receptors, and members of random peptide libraries; (see, e.g., Lam, K. S. et al., 1991, Nature 354:82–84; Houghten, R. et al., 1991, Nature 354:84–86), made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

In instances whereby a body weight disorder situation results from a lower overall level of target gene expression, target gene product, and/or target gene product activity in a cell or tissue involved in such a body weight disorder, compounds that interact with the target gene product may include ones which accentuate or amplify the activity of the bound target gene protein.

Such compounds would bring about an effective increase in the level of target gene activity, thus ameliorating symptoms. In instances whereby mutations within the target gene cause aberrant target gene proteins to be made which have a deleterious effect that leads to a body weight disorder, compounds that bind target gene protein may be identified that inhibit the activity of the bound target gene protein. Assays for testing the effectiveness of compounds, identified by, for example, techniques such as those described in Section 5.3.1–5.3.3, are discussed, below, in Section 5.3.4.

In the case of C5 gene products, such compounds can, for example, represent compounds which stimulate C5 gene product activity. For example, such compounds can stimulate C5 uncoupling activity by binding to the C5 gene product in a manner which mimics the stimulatory effect of fatty acid molecules on C5 uncoupling activity. Alternatively, such stimulatory compounds can, for example, interfere with nucleotide (e.g., GDP) binding to the C5 gene product nucleotide binding site, thereby interfering with the inhibitory effect of C5 nucleotide binding.

The compounds identified can also represent compounds which inhibit C5 gene product activity. For example, such compounds can inhibit C5 uncoupling activity by interfering with the binding of fatty acid molecules to the C5 gene product in a manner which blocks the stimulatory effect of fatty acid molecules on C5 uncoupling activity. Alternatively, such inhibitory compounds can, for example, bind to the C5 gene product in a manner with mimics nucleotide (e.g., GDP) binding to the C5 gene product nucleotide binding site such that C5 gene product activity is inhibited.

Compounds identified via assays such as those described herein may be useful, for example, in elaborating the biological function of the target gene product, for modulating thermogenesis, modulating body weight and ameliorating body weight disorders.

5.3.1. IN VITRO SCREENING ASSAYS FOR COMPOUNDS THAT BIND TO THE TARGET GENE PRODUCT

In vitro systems may be designed to identify compounds capable of binding the target gene products of the invention. Compounds identified may be useful, for example, in modulating the activity of wild type and/or mutant target gene products, may be useful in elaborating the biological function of the target gene product, may be utilized in screens for identifying compounds that disrupt normal target gene product interactions, or may in themselves disrupt such interactions.

The principle of the assays used to identify compounds that bind to the target gene product involves preparing a reaction mixture of the target gene product and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring target gene product or the test substance onto a solid phase and detecting target gene product/test compound complexes anchored on the solid phase at the end of the reaction. In one embodiment of such a method, the target gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

5.3.2. ASSAYS FOR CELLULAR PROTEINS THAT INTERACT WITH THE TARGET GENE PROTEIN

Any method suitable for detecting protein-protein interactions may be employed for identifying novel target protein-cellular or extracellular protein interactions. These methods are outlined in section 5.1.2., above, for the identification of pathway genes, and may be utilized herein with respect to the identification of proteins which interact with identified target proteins.

5.3.3. ASSAYS FOR COMPOUNDS THAT INTERFERE WITH TARGET GENE PRODUCT/CELLULAR MACROMOLECULE INTERACTION

The target gene products of the invention may, in vivo, interact with one or more cellular or extracellular macromolecules, such as proteins. Such macromolecules may include, but are not limited to, nucleic acid molecules and those proteins identified via methods such as those described, above, in Section 5.3.2. For purposes of this discussion, such cellular and extracellular macromolecules are referred to herein as "binding partners". Compounds that disrupt such interactions may be useful in regulating the activity of the target gene product, especially mutant target gene products. Such compounds may include, but are not limited to molecules such as antibodies, peptides, and the like, as described, for example, in Section 5.3.1. above.

The basic principle of the assay systems used to identify compounds that interfere with the interaction between the target gene product and its cellular or extracellular binding partner or partners involves preparing a reaction mixture containing the target gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of target gene product and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner. Additionally, complex formation within reaction mixtures containing the test compound and normal target gene protein may also be compared to complex formation within reaction mixtures containing the test compound and a mutant target gene protein. This comparison may be important in those cases wherein it is desirable to identify compounds that disrupt interactions of mutant but not normal target gene proteins.

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene protein and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the target gene protein or the interactive cellular or extracellular binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the target gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular binding partner is prepared in which either the target gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt target gene protein/cellular or extracellular binding partner interaction can be identified.

In a particular embodiment, the target gene product can be prepared for immobilization using recombinant DNA techniques described in Section 5.2.1, above. For example, the target gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practiced in the art and described above, in Section 5.2.3. This antibody can be labeled with the radioactive isotope $^{125}$I, for example, by methods routinely practiced in the art. In a heterogeneous assay, e.g., the GST-target gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the target gene product/binding partner interaction can be detected by adding the labeled antibody and measuring the radioactivity associated with the beads.

In another embodiment of the invention, these same techniques can be employed using peptide fragments that correspond to the binding domains of the target gene protein and/or the interactive cellular or extracellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular binding partner is obtained, short gene segments can be engineered to express peptide fragments of the protein, which can then be tested for binding activity and purified or synthesized.

For example, and not by way of limitation, a target gene product can be anchored to a solid material as described, above, in this Section by making a GST-target gene fusion protein and allowing it to bind to glutathione agarose beads. The interactive cellular or extracellular binding partner can be labeled with a radioactive isotope, such as $^{35}$S, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner binding domain, can be eluted, purified, and analyzed for amino acid sequence by well-known methods. Peptides so identified can be produced synthetically or fused to appropriate facilitative proteins using recombinant DNA technology.

5.3.4. ASSAYS FOR MODULATION OF BODY WEIGHT RELATED PROCESSES

Compounds, including but not limited to, compounds such as those identified in the foregoing assay systems, may be tested for the ability to modulate body weight related processes, including, for example, thermogenesis, body weight regulation and body weight disorder symptoms, which may include, for example, obesity, anorexia, and/or an abnormal level of food intake. Gene product-based, cell-based and animal model-based assays for the identification of compounds exhibiting such an ability to modulate and/or ameliorate such processes are described below.

First, cell-based systems such as those described, above, in Section 5.2.4.2, may be used to identify compounds which may act to modulate and/or ameliorate such processes, including body weight disorder symptoms.

For example, such cell systems may be exposed to a compound suspected of exhibiting an ability to modulate body weight-related processes such as an ability to ameliorate body weight disorder symptoms, at a sufficient concentration and for a time sufficient to elicit such an affect on body weight-related processes the exposed cells. After exposure, the cells are examined to determine whether one or more of the body weight-related processes has been altered.

For example, in the case of body weight disorder-like cellular phenotypes, the cells can be examined to determine whether they have been altered to resemble a more normal or more wild type, non-body weight disorder phenotype, or a phenotype more likely to produce a lower incidence or severity of disorder symptoms.

In addition, the expression and/or activity levels of exposed cells can be assayed. Taking the case of the C5 gene, cells, preferably mammalian cells, that express or are capable of expressing the C5 gene can be exposed to a test compound for a time sufficient to elicit an effect on body weight-related processed within the exposed cells. The level of C5 gene expression (via, e.g., detecting mRNA transcript or C5 gene products) and/or the level of C5 gene product activity (that is, uncoupling activity) can then be determined and compared to levels obtained in such cells in the absence of test compound. A difference in levels in exposed versus unexposed cells identifies a compound capable of modulating body weight-related processes, including, for example, thermogenesis and/or body weight disorders such as obesity and cachexia.

As discussed above, cell-based assays can, for example, be utilized to identify compounds which act to modulate body weight related processes, including thermogenesis, body weight regulation and an ability to ameliorate body weight disorders, by modulating C5 gene product uncoupling activity. Detecting an increase in the level of C5 gene expression and/or gene product activity identifies a compound which can increase the rate of thermogenesis and can cause a reduction in body weight, including a reduction in body weight associated with obesity. Detecting a compound which causes a decrease in the level of C5 gene expression and/or C5 gene product activity identifies a compound which can decrease the rate of thermogenesis and can cause an increase in body weight, including an increase in body weight associated with cachexia.

Yeast systems and assays, for example, can be utilized as models for uncoupling of oxidative phosphorylation. Such yeast systems express C5 gene sequences as, for example, described in the Example presented in Section 12, below. Uncoupling assays can be, for example, such as those described in Section 12 and in Murdza-Inglis, D. L. et al., 1994, J. Biol. Chem. 260:7435–7438; and Murdza-Inglis, D. L. et al., 1991, J. Biol. Chem. 260:11871–11875, both of which are incorporated herein by reference in their entirety. Such assays utilize potential-sensitive dyes which include, but are not limited to 3,3'-dihexylocarbocyanine ($DiOC_6$; Bouillaud, F. et al., 1994, EMBO J. 13:1990–1997; Pon, L et al., 1991, in The Molecular and Cellular Biology of the Yeast Saccharomyces (Vol. 1), Broach, J. R. et al., eds., Cold Spring Harbor Laboratory Press, Cold Spring Harbor, N.Y.; Pringle, J. R. et al., 1989, Methods Cell Biol. 31:357–435). The dyes are sensitive to the electrochemical gradient across the mitochondrial membrane and can, therefore, be utilized to detect decreases in mitochondrial potential indicative of uncoupling activity.

Purified target gene products can also be utilized in screening assays. For example, a test compound can be exposed to a target gene product at a sufficient concentration and for a time sufficient to elicit an affect on target gene product activity. The level of exposed target gene activity is then measured and compared to the level of target gene product activity obtained in the absence of test compound, such that, if the two levels differ, a compound is identified which modulates the level of target gene product activity.

Taking the case of the C5 gene, purified or partially purified natural or recombinant C5 gene product can be exposed to test compound for a time sufficient to elicit an effect on the C5 gene product. The level of C5 gene product activity (that is, uncoupling activity) can then be determined and compared to levels obtained with C5 gene product in the absence of test compound. A difference in levels in exposed versus unexposed C5 gene product identifies a compound capable of modulating C5 gene activity and, as such, identifies a compound capable of modulating thermogenesis. Such identified compounds can, further, modulate mammalian body weight-related processes, including, for example, thermogenesis and/or body weight disorders such as obesity and cachexia.

In addition, animal-based body weight process-related systems, such as those described, above, in Section 5.2.4.1, may be used to identify compounds capable of modulating body weight-related processes, including, for example, modulating body weight, modulating thermogenesis and ameliorating body weight disorder-like symptoms, such as obesity or cachexia symptoms.

Such animal models may be used as test substrates for the identification of drugs, pharmaceuticals, therapies and interventions which may be effective in treating such processes and disorders. For example, animal models may be exposed to a test compound suspected of exhibiting an ability to modulate thermogenesis, modulate body weight or ameliorate body weight disorder symptoms, at a sufficient concentration and for a time sufficient to elicit such a body weight related effect in the exposed animals. The response of the animals to the exposure may be monitored by, for example, assessing the reversal of disorders associated with body weight disorders such as obesity or cachexia, by assaying uncoupling activities via, for example, procedures such as those described above, or by measuring the level or activity of the target gene or gene product of interest.

With regard to intervention, any treatments which reverse any aspect of body weight disorder-like symptoms should be considered as candidates for human body weight disorder therapeutic intervention. Dosages of test agents may be determined by deriving dose-response curves, as discussed in Section 5.5.1, below.

Gene expression patterns may be utilized in conjunction with either cell-based or animal-based systems to assess the ability of a compound to modulate body weight-related processes such as, for example, an ability to ameliorate body weight disorder-like symptoms. For example, the expression pattern of one or more fingerprint genes may form part of a fingerprint profile which may be then be used in such an assessment. Fingerprint profiles are described, below, in Section 5.7.1. Fingerprint profiles may be characterized for known states, either body weight disorder or normal states, within the cell- and/or animal-based model systems. Subsequently, these known fingerprint profiles may be compared to ascertain the effect a test compound has to modify such fingerprint profiles, and to cause the profile to more closely resemble that of a more desirable fingerprint. For example, administration of a compound may cause the fingerprint profile of a body weight disorder model system to more closely resemble the control system. Administration of a compound may, alternatively, cause the fingerprint profile of a control system to begin to mimic a body weight disorder state, which may, for example, be used in further characterizing the compound of interest, or may be used in the generation of additional animal models.

5.4. COMPOUNDS AND METHODS FOR MODULATION OF BODY WEIGHT-RELATED PROCESSES

Described below are methods and compositions whereby body weight-related processes, including, but not limited to, modulation of body weight, modulation of thermogenesis and/or modulation, amelioration and treatment of body weight disorder symptoms, such as, for example, obesity and cachexia.

It is possible that body weight disorders may be brought about, at least in part, by an abnormal level of target gene product, or by the presence of a target gene product exhibiting an abnormal activity. As such, the reduction in the level and/or activity of such target gene products would bring about the amelioration of body weight disorder-like symptoms. Techniques for the reduction of target gene expression levels or target gene product activity levels are discussed in Section 5.4.1, below.

Alternatively, it is possible that body weight disorders may be brought about, at least in part, by the absence or reduction of the level of target gene expression, or a reduction in the level of a target gene product's activity. As such, an increase in the level of target gene expression and/or the activity of such gene products would bring about the amelioration of body weight disorder-like symptoms. Techniques for increasing target gene expression levels or target gene product activity levels are discussed in Section 5.4.2, below.

It is possible that body weight related processes may be brought about, at least in part, by the presence of a certain level of target gene product or target gene product activity. As such, the modulation in the level and/or activity of such target gene products would bring about a modulation of one or more body weight-related processes. Techniques for the reduction of target gene expression levels or target gene product activity levels are discussed in Section 5.4.1, below. Techniques for increasing target gene expression levels or target gene product activity levels are discussed in Section 5.4.2, below.

5.4.1. COMPOUNDS THAT INHIBIT EXPRESSION, ACTIVITY OF

As discussed above, target genes involved in body weight disorders may cause such disorders via an increased level of target gene activity. A variety of techniques may be utilized to inhibit the expression, synthesis, or activity of such target genes and/or gene products, thereby modulating the body weight-related process or ameliorating symptoms of the body weight disorder.

For example, compounds such as those identified through assays described, above, in Section 5.3, which exhibit inhibitory activity, may be used in accordance with the invention to modulate body weight-related processes, including ameliorating body weight disorder symptoms. As discussed in Section 5.3, above, such molecules may include, but are not limited to, peptides, (such as, for example, peptides representing soluble extracellular portions of target gene product transmembrane receptors), phosphopeptides, small organic or inorganic molecules, or antibodies (including, for example, polyclonal, monoclonal, humanized, anti-idiotypic, chimeric or single chain antibodies, and FAb, $F(ab')_2$ and FAb expression library fragments, and epitope-binding fragments thereof). Techniques for determination of effective doses and administration of such compounds are described below, in Section 5.5.1. Inhibitory antibody techniques are further described, below, in Section 5.4.1.2.

In the case of C5 gene products, such can, for example, represent compounds which inhibit C5 gene product expression or activity. For example, such compounds can inhibit C5 uncoupling activity by interfering with the binding of fatty acid molecules to the C5 gene product in a manner which blocks the stimulatory effect of fatty acid molecules on C5 uncoupling activity. Alternatively, such inhibitory compounds can, for example, bind to the C5 gene product in a manner with mimics nucleotide (e.g., GDP) binding to the C5 gene product nucleotide binding site such that C5 gene product activity is inhibited.

Further, antisense and ribozyme molecules which inhibit expression of the target gene may also be used in accordance with the invention to inhibit the aberrant target gene activity. Such techniques are described, below, in Section 5.4.1.1. Still further, as described, below, in Section 5.4.1.1, triple helix molecules may be utilized in inhibiting the aberrant target gene activity.

5.4.1.1. INHIBITORY ANTISENSE, RIBOZYME AND TRIPLE HELIX APPROACHES

Among the compounds which may exhibit the ability to modulate body weight-related processes, including the ability to ameliorate body weight disorder symptoms, are antisense, ribozyme, and triple helix molecules. Such molecules may be designed to reduce or inhibit either wild type, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335.

Taking the C5 gene as an example, oligonucleotides complementary to either the 5'- or 3'- non-translated, non-coding regions of the C5 gene shown in FIGS. 16A–16B (murine; SEQ ID NO.:36) or FIGS. 18A–18B (human; SEQ ID NO.:38)) could be used in an antisense approach to inhibit translation of endogenous C5 mRNA.

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the target gene coding region sequence could be used, those complementary to the transcribed, untranslated region are most preferred. Taking the human C5 gene as an example, antisense oligonucleotides having the following sequences can, for example, be utilized in accordance with the invention:

a) 5'-CATGATGCTGATTTCCTG-3';
b) 5'-CATGATGCTGATTTCCTGCTACGT-3';
c) 5'-CATGATGCTGATTTCCTGCTACGTCCCAGG-AGA-3';
d) 5'-CAACCATGATGCTGATTTCCTGCTACGTCC-CAG-3';
f) 5'-CAACCATGATGCTGATTTCCTGCTACG-3';
g) 5'-CAACCATGATGCTGATTTCCTGCTACG-3'; and
h) 5'-CAACCATGATGCTGATT-3'.

The antisense molecules should be delivered to cells which express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver et al., 1990, Science 247:1222–1225).

Ribozymes are enzymatic RNA molecules capable of catalyzing the specific cleavage of RNA. (For a review, see Rossi, J., 1994, Current Biology 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591, which is incorporated herein by reference in its entirety.

Preferably the ribozyme is engineered so that the cleavage recognition site is located near the 5' end of the target gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g. for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas & Capecchi 1987 and Thompson 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.5. that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.1.2. ANTIBODIES FOR INHIBITION OF TARGET GENE PRODUCTS

Antibodies that are both specific for target gene protein and interfere with its activity may be used to inhibit target gene function. Where desirable, antibodies specific for mutant target protein which interfere with the activity of such mutant target product may also be used to inhibit target gene function. Such antibodies may be generated using standard techniques described in Section 5.2.3., supra, against the proteins themselves or against peptides corresponding to portions of the proteins. The antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin or liposomes may be used to deliver the antibody or a fragment of the Fab region which binds to the target gene product epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Creighton, 1983, supra; and Sambrook et al., 1989, supra).

Alternatively, single chain neutralizing antibodies which bind to intracellular target gene product epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

In instances where the target gene protein is extracellular, or is a transmembrane protein, any of the administration techniques described, below in Section 5.5 which are appropriate for peptide administration may be utilized to effectively administer inhibitory target gene antibodies to their site of action.

5.4.2. COMPOUNDS THAT INCREASE EXPRESSION, SYNTHESIS OR ACTIVITY OF TARGET GENES

Body weight-related processes, including body weight disorders, may be modulated via an increase in the levels and/or activity of target gene products. A variety of techinques may be utilized to increase the expression, synthesis or activity of target genes and/or gene products, thereby modulating body weight-related processes, including ameliorating symptoms of body weight disorders. The level of gene activity may be increased, for example, by either increasing the level of target gene product present or by increasing the level of active target gene product which is present.

For example, a target gene protein, at a level sufficient to modulate a body weight-related process, such as, for example body weight disorder such that symptoms of the body weight disorder are ameliorated, may be administered to a patient. Any of the techniques discussed, below, in Section 5.5, may be utilized for such administration. One of skill in the art will readily know how to determine the concentration of effective, non-toxic doses of the normal target gene protein, utilizing techniques such as those described, below, in Section 5.5.1.

Further, patients may be treated by gene replacement therapy. One or more copies of a normal target gene or a portion of the gene that directs the production of a normal target gene protein with target gene function, may be inserted into cells, using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Taking the C5 gene as an example, such techniques can be utilized to express C5 gene sequences within cell types of interest without resorting to undue experimentation. For example, regulatory sequences (e.g., promoter/enhancer sequences) capable of selectively driving expression in muscle or adipose cells are well known to those of ordinary skill in the art. Such sequences include, but are not limited to, aP2 promoter sequences, which drive adipose tissue-specific expression (see, e.g., Kopecky, J. et al., 1995, J. Clin. Invest. 96:2914–2923). Recombinant C5 gene sequences, therefore, can be overexpressed in adipose cells a cell type of interest, for example, via aP2 promoter sequences to which they have been ligated in a manner that drives C5 expression.

Cells, preferably, autologous cells, containing normal target gene-expressing gene sequences may then be introduced or reintroduced into the patient at positions which allow for the amelioration of body weight disorder symptoms. Such cell replacement techniques may be preferred, for example, when the target gene product is a secreted, extracellular gene product.

Additionally, antibodies may be administered which specifically bind to a target protein and, by binding, serve to, either directly or indirectly, activate the target protein function. Such antibodies can include, but are not limited to polyclonal, monoclonal, FAb fragments, single chain antibodies, chimeric antibodies and the like. The antibodies may be generated using standard techniques such as those described, above, in Section 5.2.3., and may be generated against the protein themselves or against proteins corresponding to portions of the proteins. The antibodies may be administered, for example, according to the techniques described, above, in Section 5.4.1.2.

Additionally, any other compound identified which increases the level of target gene expression or the level of target gene product activity and be administered herein. Administration techniques can be as those described, below, in Section 5.5.

In the case of C5 gene products, such compounds can, for example, represent compounds which stimulate C5 gene product activity. For example, such compounds can stimulate C5 uncoupling activity by binding to the C5 gene product in a manner which mimics the stimulatory effect of fatty acid molecules on C5 uncoupling activity. Alternatively, such stimulatory compounds can, for example, interfere with nucleotide (e.g., GDP) binding to the C5 gene product nucleotide binding site, thereby interfering with the inhibitory effect of C5 nucleotide binding.

5.5. PHARMACEUTICAL PREPARATIONS AND METHODS OF ADMINISTRATION

The identified compounds, nucleic acid molecules and cells that affect target gene expression, synthesis and/or activity can be administered to a patient at therapeutically effective doses to treat or ameliorate body weight disorders. A therapeutically effective dose refers to that amount of the compound sufficient to result in amelioration of symptoms of body weight disorder, or alternatively, to that amount of a nucleic acid molecule sufficient to express a concentration of gene product which results in the amelioration of such symptoms.

5.5.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.5.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.6. DIAGNOSIS OF BODY WEIGHT DISORDER ABNORMALITIES

A variety of methods may be employed for the diagnosis of body weight disorders, predisposition to body weight disorders, for monitoring the efficacy of antibody weight disorder compounds during, for example, clinical trials and for monitoring patients undergoing clinical evaluation for the treatment of such body weight disorders.

Such methods may, for example, utilize reagents such as the fingerprint gene nucleotide sequences described in Sections 5.1, and antibodies directed against differentially expressed and pathway gene peptides, as described, above, in Sections 5.1.3 (peptides) and 5.2.3 (antibodies). Specifically, such reagents may be used, for example, for: (1) the detection of the presence of target gene mutations, or the detection of either over- or under-expression of target gene mRNA relative to the non-body weight disorder state; and (2) the detection of either an over- or an under-abundance of target gene product relative to the non-body weight disorder state.

The methods described herein may be performed, for example, by utilizing pre-packaged diagnostic kits comprising at least one specific fingerprint gene nucleic acid or anti-fingerprint gene antibody reagent described herein, which may be conveniently used, e.g., in clinical settings, to diagnose patients exhibiting body weight disorder abnormalities.

Any cell type or tissue in which the fingerprint gene is expressed may be utilized in the diagnostics described below.

Among the methods which can be utilized herein are methods for monitoring the efficacy of compounds in clinical trails for the treatment of body weight disorders. Such compounds can, for example, be compounds such as those described, above, in Section 5.4. Such a method comprises detecting, in a patient sample, a gene transcript or gene product which is differentially expressed in a body weight disorder state relative to its expression in a normal, or non-body weight disorder, state.

Any of the nucleic acid detection techniques described, below, in Section 5.7.1 or any of the peptide detection described, below, in Section 5.7.2 can be used to detect the gene transcript or gene product which is differentially expressed in a body weight disorder relative to its expression in the normal, or non-immune disorder, state.

During clinical trials, for example, the expression of a single fingerprint gene, or alternatively, a fingerprint pattern of a cell involved in a body weight disorder can be determined in the presence or absence of the compound being tested. The efficacy of the compound can be followed by comparing the expression data obtained to the corresponding known expression patterns in a normal, non-body weight disorder state. Compounds exhibiting efficacy are those which alter the single fingerprint gene expression and/or the fingerprint pattern to more closely resemble that of the normal, non-body weight disorder state.

The detection of the product or products of genes differentially expressed in a body weight disorder state relative to their expression in a normal, or non-body weight disorder, state can also be used for monitoring the efficacy of potential anti-body weight disorder compounds during clinical trials. During clinical trials, for example, the level and/or activity of the products of one or more such differentially expressed genes can be determined in relevant cells and/or tissues in the presence or absence of the compound being tested. The efficacy of the compound can be followed by comparing the protein level and/or activity data obtained to the corresponding known levels/activities for the cells and/or tissues in a normal, non-body weight disorder state. Compounds exhibiting efficacy are those which alter the pattern of the cell and/or tissue involved in the body weight disorder to more closely resemble that of the normal, non-body weight disorder state.

5.6.1. DETECTION OF FINGERPRINT GENE NUCLEIC ACIDS

DNA or RNA from the cell type or tissue to be analyzed may easily be isolated using procedures which are well known to those in the art. Diagnostic procedures may also be performed "in situ" directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Fingerprint gene nucleotide sequences, either RNA or DNA, may, for example, be used in hybridization or amplification assays of biological samples to detect body weight disorder-related gene structures and expression. Such assays may include, but are not limited to, Southern or Northern analyses, single stranded conformational polymorphism analyses, in situ hybridization assays, and polymerase chain reaction analyses. Such analyses may reveal both quantitative aspects of the expression pattern of the fingerprint gene, and qualitative aspects of the fingerprint gene expression and/or gene composition. That is, such techniques may include, for example, point mutations, insertions, deletions, chromosomal rearrangements, and/or activation or inactivation of gene expression.

Diagnostic methods for the detection of fingerprint gene-specific nucleic acid molecules may involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule of interest. Preferably, the lengths of these nucleic acid reagents are at least 15 to 30 nucleotides. After incubation, all non-annealed nucleic acids are removed from the nucleic acid:fingerprint molecule hybrid. The presence of nucleic acids from the cell type or tissue which have hybridized, if any such molecules exist, is then detected. Using such a detection scheme, the nucleic acid from the cell type or tissue of interest may be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled fingerprint nucleic acid reagents is accomplished using standard techniques well-known to those in the art.

Alternative diagnostic methods for the detection of fingerprint gene specific nucleic acid molecules may involve their amplification, e.g., by PCR (the experimental embodiment set forth in Mullis, K. B., 1987, U.S. Pat. No. 4,683, 202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D. Y et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

In addition to methods which focus primarily on the detection of one fingerprint nucleic acid sequence, fingerprint patterns or profiles may also be assessed in such detection schemes. "Fingerprint pattern" or "fingerprint profile", as used herein, refers to the pattern of mRNA expression obtained for a given tissue or cell type under a given set of conditions, and includes the mRNA expression of at least two of the genes within the tissue or cell type. Such conditions may include, but are not limited to body weight disorders, including obesity, and conditions relevant to processes involved in body weight or appetite regulation, including any of the control or experimental conditions described in the paradigms of Section 5.1.1.1, above. Fingerprint profiles may be generated, for example, by utilizing a differential display procedure, as discussed, above, in Section 5.1.1.2, Northern analysis and/or RT-PCR. Any of the gene sequences described, above, in Section 5.2.1 may be used as probes and/or PCR primers for the generation and corroboration of such fingerprint profiles.

5.6.2. DETECTION OF TARGET GENE PEPTIDES

Antibodies directed against wild type or mutant fingerprint gene peptides, which are discussed, above, in Section 5.2.3, may also be used as body weight disorder diagnostics and prognostics, as described, for example, herein. Such diagnostic methods, may be used to detect abnormalities in the level of fingerprint gene protein expression, or abnormalities in the structure and/or temporal, tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be isolated using techniques which are well known to those of skill in the art. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of wild type or mutant fingerprint gene peptide molecules may involve, for example, immunoassays wherein fingerprint gene peptides are detected by their interaction with an anti-fingerprint gene product-specific antibody.

For example, antibodies, or fragments of antibodies, such as those described, above, in Section 5.2.3, useful in the present invention may be used to quantitatively or qualitatively detect the presence of wild type or mutant fingerprint gene peptides. This can be accomplished, for example, by immunofluorescence techniques employing a fluorescently labeled antibody (see below, this Section) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled fingerprint gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or anti-mutant fingerprint gene product antibody may be determined according to well known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, ENZYME IMMUNOASSAY, CRC Press, Boca Raton, Fla.; Ishikawa, E. et al., (eds.), 1981, ENZYME IMMUNOASSAY, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE: IDENTIFICATION AND CHARACTERIZATION OF AN OBESITY-RELATED GENE

In the Example presented in this Section, one of the paradigms described, above, in Section 5.1.1.1, the genetic obesity paradigm, is utilized to identify a gene which is not only differentially expressed in genetically obese test animals, but is identical to a gene which has previously been implicated in processes involved in body weight regulation. Thus, the successful identification, here, of this gene corroborates the usefulness of the paradigm approach of the invention for the identification of genes involved in body weight disorders and/or in body weight or appetite regulation.

6.1. MATERIALS AND METHODS

Genetic obesity paradigms: 15 female C57B1/6J ob/ob mice and lean littermate controls (15 female C57B1/6J ?/+) and 15 male C57B1/Ks db/db mice and lean littermate controls (15 male C57B1/ks +/+) were received from Jackson labs at 4.5 weeks of age, and housed individually on normal mouse chow (West, D. B., 1992, Am. J. Physiol. 262:R1025–R1032) for 1 week prior to the initiation of the study. The four groups of 15 mice each were then sacrificed by $CO_2$ euthanasia and tissues were collected. Body weight (grams) of the four groups of mice at the time of sacrifice was measured.

Tissue collection and RNA isolation: Following $CO_2$ asphyxiation, tissues were removed and quick frozen on dry ice. Samples within an experimental or control group (15 animals per group) were then homogenized together with a mortar and pestle under liquid nitrogen.

Total cellular RNA was extracted from tissue with either RNAzol™ or RNAzolB™ (Tel-Test, Friendswood, Tex.), according to the manufacturer's instructions. Briefly, the tissue was solubilized in an appropriate amount of RNAzol™ or RNAzolB™, and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically ($A_{260}$).

Differential display: Total cellular RNA (10–50 μg) was treated with 20 Units DNase I (Boehringer Mannheim, Germany) in the presence of 40 Units ribonuclease inhibitor (Boehringer Mannheim, Germany). After extraction with phenol/chloroform and ethanol precipitation, the RNA was dissolved in DEPC (diethyl pyrocarbonate)-treated water.

Differential mRNA display was carried out as described, above, in Section 5.1.1.2. RNA (0.4–2 μg) was reverse-transcribed using Superscript reverse transcriptase (GIBCO/BRL). The cDNAs were then amplified by PCR on a Perkin-Elmer 9600 thermal cycler. The reaction mixtures (20 μl) included arbitrary decanucleotides and one of twelve possible $T_{11}VN$ sequences, wherein V represents either dG, dC, or dA, and N represents either dG, dT, dA, or dC. Parameters for the 40 cycle PCR were as follows: Hold 94° C. 2 minutes; Cycle (40 rounds) 94° C. 15 seconds, 40° C. 2 minutes; Ramp to 72° 30 seconds; Hold 72° C. 5 minutes; Hold 4° C.

Radiolabelled PCR amplification products were analyzed by electrophoresis on 6% denaturing polyacrylamide gels.

Reamplification and subcloning: PCR bands of interest were recovered from sequencing gels and reamplified.

Briefly, autoradiograms were aligned with the dried gel, and the region containing the bands of interest was excised with a scalpel. The excised gel fragment was eluted by soaking in 100 μl TE (Tris-EDTA) buffer at approximately 100° C. for 15 minutes. The gel slice was then pelleted by brief centrifugation and the supernatant was transferred to a new microcentrifuge tube. DNA was combined with ethanol in the presence of 100 mM Sodium acetate and 30 μg glycogen (Boerhinger Mannhein, Germany) and precipitated on dry ice for approximately 10 minutes. Samples were centrifuged for 10 minutes and pellets were washed with 80% ethanol. Pellets were resuspended in 10 μl distilled water.

5 μl of the eluted DNA were reamplified in a 100 μl reaction containing: standard Cetus Taq polymerase buffer, 20 μM dNTPs, 1 μM of each of the oligonucleotide primers used in the initial generation of the amplified DNA. Cycling conditions used were the same as the initial conditions used to generate the amplified band, as described above. One-half of the amplification reaction was run on a 2% agarose gel and eluted using DE-81 paper (Whatman Paper, Ltd., England) as described in Sambrook et al., supra. Recovered fragments were ligated into the cloning vector pCR™II (Invitrogen, Inc., San Diego Calif.) and transformed into competent *E. coli* strain DH5α (Gibco/BRL, Gaithersburg, Md.). Colonies were grown on LB-agar plates containing ampicillin (100 μg/ml) and X-gal (40 μg/ml) to permit blue/white selection.

Sequence analysis: After subcloning, reamplified cDNA fragments were sequenced on an Applied Biosystems Automated Sequencer (Applied Biosystems, Inc. Seattle, Wash.). Sequence was obtained from four independent transformants containing the same insert. The nucleotide sequence shown herein represents the consensus of the information obtained from the four sequences. Such primary sequence data was edited and trimmed of vector sequences and highly repetitive sequences and used to search Genbank databases using the BLAST (Altschul, S. F. et al., 1990, J. Mol. Biol. 215:403–410) program.

Northern analysis: RNA samples were electrophoresed in a denaturing agarose gel containing 1–1.5% agarose (SeaKem™ LE, FMC BioProducts, Rockland, Me.) containing 6.3% formaldehyde. Samples containing 5–20 μg of total RNA were mixed with denaturing loading solution (72% deionized formamide and bromophenol blue) and heated to 70° C. for 5 minutes. Samples were placed on ice and immediately loaded onto gels. Gels were run in 1× MOPS buffer (100 mM MOPS, 25 mM sodium acetate, 5 mM EDTA). After electrophoresis, the gels were stained with ethidium bromide and visualized with ultraviolet light.

After completion of electrophoresis, gels were soaked in 50 mM sodium hydroxide with gentle agitation for approximately 30 minutes to lightly cleave RNA. Gels were rinsed twice in water and then neutralized by soaking in 0.1M Tris-HCl (pH 7.5) for approximately 30 minutes. Gels were briefly equilibrated with 20× SSC (3M sodium chloride, 0.3M sodium citrate) and then transferred to nylon membranes such as Hybond™, -N, (Amersham, Inc., Arlington Heights, Ill.) or Zeta-Probe (Bio-Rad, Inc., Hercules, Calif.) overnight in 20× SSC. Membranes containing transferred RNA were baked at 80° C. for 2 hours to immobilize the RNA.

DNA fragments to be used as probes were of various sizes and were labeled using a random hexamer labeling technique. Briefly, 25 ng of a purified DNA fragment was used to generate each probe. Fragments were added to a 20 μl random hexanucleotide labeling reaction (Boehringer Mannhein, Inc., Indianapolis, Ind.) containing random hexamers and a mix of the nucleotides dCTP, dGTP, and dTTP (at a final concentration of 25 μM each). The reaction mix was heat-denatured at 100° C. for 10 minutes and then chilled on ice. 5 μl of α-$^{32}$P-dATP (50 μCi; Amersham, Inc., Arlington Heights, Ill.) and Klenow DNA polymerase (2 units; Boehringer Mannheim, Inc., Indianapolis, Ind.) were added. Reactions were incubated at 37° for 30 minutes. Following incubation, 30 μl water was added to the labeling reaction and unincorporated nucleotides were removed by passing the reactions through a BioSpin-6™ chromatography column (Bio-Rad, Inc., Hercules, Calif.). Specific incorporation was determined using a scintillation counter. 1–5× $10^6$ cpm were used per ml hybridization mixture.

Nylon membranes containing immobilized RNA were prehybridized according to manufacturer's instructions. Radiolabelled probes were heat denatured at 70° C. in 50% deionized formamide for 10 minutes and ten added to the hybridization mixture (containing 50% formamide, 10% dextran sulfate, 0.1% SDS, 100 µg/ml sheared salmon sperm DNA, 5× SSC, 5× Denhardt's solution, 30 mM Tris-HCl (pH 8.5), 50 mM NaPO$_4$ (pH 6.5). Hybridizations were carried out at 42° C. overnight. Nylon membranes were then bathed for 2 minutes in a wash solution of 0.2× SSC and 0.1% SDS at room temperature to remove most of the remaining hybridization solution. The membranes were then bathed twice in fresh 42° C. preheated wash solution for 20 minutes. Filters were covered in plastic wrap and exposed to autoradiographic film to visualize results.

6.2. RESULTS

Genetic obesity paradigms were utilized to identify genes which are differentially expressed in obese versus lean mice. Specifically, ob/ob and db/db obese mice were utilized in conjunction with lean littermate control mice, as described, above, in Section 6.1.

RNA samples isolated from liver tissue of the ob/ob, db/db, and littermate control mice were analyzed via differential display techniques. FIG. 1 shows amplified fragments obtained from these tissues when subjected to PCR with 11 separate primer pair combinations. The arrow in FIG. 1, indicates a PCR product, designated band L36, which was judged to be differentially expressed among the lean and obese (ob and db) samples, with a larger amount of expression in the obese relative to the lean control samples.

To confirm the putative differential gene regulation, the amplified L36 band was recovered, reamplified, and used to probe Northern RNA blots which were prepared with the original liver RNA samples. FIG. 2 shows the results of one such Northern blot analysis, in which the steady messages corresponding to cDNA band L36 are shown to be significantly increased in RNA samples derived from both ob/ob and db/db mice compared to lean littermate controls. Thus, this study confirmed the putative differential regulation which had been suggested by the differential display result.

The reamplified fragment corresponding to band L36 was subcloned into a cloning vector and sequenced, as described, above, in Section 6.1. Plasmid DNA from four independent transformants was sequenced. All four plasmids were shown to contain the same insert and a consensus sequence of the four sequences was compiled and is shown in FIG. 3A.

A database search with this consensus sequence resulted in an alignment with greater than 99% identity to a mouse stearoyl-Co-A desaturase gene, SCD1 (Ntambi, J. M. et al., 1988, J. Biol. Chem. 263:17291–17300; Kaestner, K. H. et al., 1989, J. Biol. Chem. 264:14755–14761), which encodes an enzyme that converts saturated fats to mono-unsaturated fats in the liver (FIG. 3B).

Mouse stearoyl-Co-A-desaturase mRNA is induced in liver upon feeding of fasted animals (Ntambi, J. M. et al., supra; Ntambi, J. M., 1992, J. Biol. Chem. 267:10925–10930). Further, in studies of lean versus obese mice, rats and chickens, stearoyl-Co-A enzymatic activity has consistently been reported to be higher in fat than lean animals (Esner, M., 1979, Biochem. J. 180:551–558; Wahle, K. W. J. and Radcliffe, J. D., 1977, Lipids 12:135–139; Legrand, P. et al., 1987, Comp. Biochem. Physiol. 87B:789–792). Additionally, it has been shown that stearoyl-Co-A activity is higher in chickens than turkeys (Kouba, M. et al., 1993, Comp. Biochem. Physiol. 105A:359–362). It is considered that turkeys are a low fat animal as compared to chickens. Thus, it is likely that the stearoyl-Co-A enzyme is involved in such body weight regulating processes as control, metabolism and storage of dietary components.

Therefore, by utilizing the genetic obesity paradigms described in this Section and in Section 5.1.1.1, above, a differentially regulated gene, the mouse stearoyl-Co-A gene, involved in body weight regulation has been identified, thereby corroborating the usefulness of such paradigms in identifying genes important to body weight disorders, and/or body weight or appetite regulation.

7. EXAMPLE: IDENTIFICATION OF GENES DIFFERENTIALLY EXPRESSED IN RESPONSE TO SHORT TERM APPETITE CONTROL PARADIGMS

In the Example presented in this Section, the short term appetite control paradigm, as described, above, in Section 5.1.1.1, is utilized to identify gene sequences which are differentially expressed and which may contribute to body weight disorders and/or may be involved in such processes as body weight regulation or appetite modulation.

7.1. MATERIALS AND METHODS

Short term appetite control paradigm: 45 male C57B1/6J mice 8 weeks of age were received from Jackson labs. The animals were randomized into three groups of 15 mice each, and housed individually on normal mouse chow (West, D. B. et al., 1992, Am. J. Physiol. 262:R1025–R1032)) for 1 week prior to the initiation of the study. Group 1 mice (Control) were maintained on ad lib mouse chow up until the time of sacrifice. Group 2 mice (Fasted) were fasted for 24 hours prior to sacrifice (water continuously available). Group 3 mice (Fasted-Refed) were fasted for 24 hours and then offered a highly palatable meal (mouse chow mixed with peanut butter) for 1 hour prior to sacrifice. All mice were weighed immediately before the initiation of the experiment and immediately afterward. All mice were sacrificed by $CO_2$ asphyxiation.

RT-PCR analysis: Quantitative RT-PCR was performed as follows. 1–2 µg of total RNA, prepared as described, above, in Section 6.1, was reverse transcribed with oligo $dT_{(12-18)}$ primers and Superscript™ RNAase H-reverse transcriptase (Gibco-BRL, Gaithersburg, Md.). Briefly, RNA was combined with 1 µl oligo dT (500 µg/ml) in a total volume of 11 µl. The mixture was heated to 70° C. for 10 minutes and chilled on ice. After a brief centrifugation RNA was reverse transcribed for 1 hour. Aliquots of the first strand cDNA were stored at −20° C. until just prior to use.

Expression levels were determined by PCR amplification of serial dilutions of first strand cDNA. In this procedure, cDNA is serially diluted in water. The dilutions are then batch amplified by PCR using sequence-specific primers. All PCR reactions are amplified under identical conditions. Therefore, the amount of product generated should reflect the amount of sequence template which was initially present. 5–10 fold dilutions of cDNA were used and enough dilutions were used such that the amount of product subsequently produced ranged from clearly visible, by UV illumination of ethidium bromide-stained gels, to below detection levels. The method described herein can distinguish 10-fold differences in expression levels.

Primers were designed for the amplification of the sequenced amplified bands, which were chosen using the program OLIGO (National Biosciences, Plymouth, Minn.). All quantitative PCR reactions were carried out in a 9600 Perkin-Elmer PCR machine (Perkin-Elmer). Generally, amplification conditions were as follows: 30–40 cycles consisting of a 95° C. denaturation for 30 seconds, 72° C. extension for 1 minute, 50–60° C. annealing for 30 seconds. Following cycling, reactions were extended for 10 minutes at 72° C.

Other procedures: All other tissue collection, RNA isolation, differential display, sequence analysis, and Northern procedures performed in the experiments described in this Section were as described, above, in Section 6.1.

7.2. RESULTS

Mice, as described, above, in Section 7.1, were utilized as part of short term appetite control paradigms. Briefly, C57B1/6J mice were divided into Control, Fasted, and Fasted-Refed groups, in order to identify genes which are differentially expressed in response to hunger and satiety.

The mice were weighed immediately before the initiation of the study and immediately prior to their sacrifice at the end of the study. Body weights (in grams) were as in Table 3, below:

TABLE 3

|  | Control | Fasted | Fasted-Refed |
|---|---|---|---|
| Before Study | 23.9 +/− 1.3 | 23.3 +/− 1.1 | 23.2 +/− 1.4 |
| After Study | 24.4 +/− 1.4 | 19.3 +/− 1.1 | 21.7 +/− 1.4 |

Upon sacrifice, Control, Fasted, and Fasted-Refed tissues were collected and immediately frozen. The tissues collected were: hypothalamus, liver, small intestine, pancreas, stomach, and omental adipose tissue. RNA was collected from the tissue samples obtained and was subjected to differential display, as described, above, in Section 7.1.

Utilizing such short term appetite control paradigms and differential display techniques, several gene sequences were identified. Data obtained from such sequences is summarized, below, in Table 4. The differential expression data identifying these gene sequences as corresponding to genes which may be involved in body weight disorders and/or body weight or appetite regulation is listed in the columns headed "Fasted" and "Refed", depending on the paradigm in which differential expression of a given gene was analyzed. Further, the tissue in which the differential expression was observed is noted, as is the difference in expression of each gene in the experimental (either fasted or refed animals) versus control tissues. "↑" indicates that gene expression is increased (i.e., there is an increase in the amount of detectable mRNA produced by a given gene) in experimental versus control tissue, while "↓" indicates that gene expression is decreased (i.e., there is an decrease in the amount of detectable mRNA produced by a given gene) in experimental versus control tissue. Table 4 also notes whether the gene sequence corresponds to a gene which had previously been identified, and additionally notes the figure in which the nucleotide sequence of the given sequence is listed.

TABLE 4

| Gene | Fasted | Refed | Previously Known | Sequence |
|---|---|---|---|---|
| P3 (SEQ. ID NO:4, 39) | ⇑Pancreas |  | Yes | FIG. 4 |
| P13 (SEQ. ID NO:7, 40–42) | ⇑Pancreas |  | Yes | FIG. 5 |
| F5 (SEQ. ID NO:12) | ⇑Adipose |  | Yes | FIG. 6 |
| L7/L21 (SEQ. ID NO:18) | ⇑Liver |  | Yes | FIG. 9 |
| H27 (SEQ. ID NO:49) | ⇓Hypothalamus |  | Yes | FIG. 20 |

In addition to the tissues, listed above in Table 4, in which the initial differential expression was observed, further analysis of the tissue distribution of gene expression of the differentially expressed genes has been conducted. Such an analysis consisted of either Northern or RT-PCR studies, or both, as described, above, in Section 7.1. The tissue distribution information obtained for the above-listed genes is reported, above, in Table 1 of Section 5.2.1.

Database searches revealed that the genes listed in Table 4, above, identified via the short term appetite control paradigms described herein have previously been identified. Specifically, P3 (SEQ ID NO.:4) represents the gene encoding mouse glutamine synthetase (FIG. 4); P13 (SEQ ID NO.:7, 40–42) represents the gene encoding mouse islet regenerating protein (FIG. 5); F5 (SEQ ID NO.:12) represents the gene encoding mouse α-amylase (FIG. 6); L7/L21 (SEQ ID NO.:18) represents the gene encoding mouse cytochrome c oxidase subunit I (FIG. 9); and H27 (SEQ ID NO:49) represents the gene encoding mouse autoantigen La (FIG. 20).

8. EXAMPLE: IDENTIFICATION OF GENES DIFFERENTIALLY EXPRESSED IN RESPONSE TO GENETIC OBESITY PARADIGMS

In the Example presented in this Section, genetic obesity paradigms, as described, above, in Section 5.1.1.1, were utilized to identify gene sequences which are differentially expressed and which may contribute to body weight disorders and/or may be involved in such processes as body weight regulation or appetite modulation.

8.1. MATERIALS AND METHODS

Genetic obesity paradigms: Animals and animal treatments were as described above, in Section 6.1.

Other procedures: All other tissue collection, RNA isolation, differential display and sequence analysis procedures performed in the experiments described in this Section were as described, above, in Section 6.1. RT-PCR procedures were as described, above, in Section 7.1.

8.2. RESULTS

Ob/ob, db/db, and lean littermate control mice, as described, above, in Section 8.1, were utilized as part of genetic obesity paradigms. The mice were weighed at the end of the study, immediately prior to sacrifice.

Upon sacrifice, tissues were collected from the four groups (i.e., ob/ob, db/db and lean littermate controls) and immediately frozen. The tissues collected were: hypothalamus, liver, small intestine, pancreas, stomach, epididymal or uterine fat pads, and skeletal muscle. RNA was collected from the tissue samples obtained and was subjected to differential display, as described, above, in Section 8.1.

Utilizing such genetic obesity paradigms and differential display techniques, several gene sequences, corresponding to both unique (i.e., previously unknown) and known genes were identified. Data obtained from such sequences is summarized, below, in Table 5. The differential expression data identifying these gene sequences as corresponding to genes which may be involved in body weight disorders and/or body weight or appetite regulation is listed in the columns headed "Ob/ob and "Db/db", depending on the paradigm in which differential expression of a given gene was analyzed. Further, the tissue in which the differential expression was observed is noted, as is the difference in expression of each gene in the experimental (either ob or db animals) versus control tissues. "↑" indicates that gene expression is increased (i.e., there is an increase in the amount of detectable mRNA produced by a given gene) in experimental versus control tissue, while "↓" indicates that gene expression is decreased (i.e., there is an decrease in the amount of detectable mRNA produced by a given gene) in experimental versus control tissue. Further, "+" indicates that gene expression was activated in experimental versus control tissue, i.e., mRNA was detectable in experimental tissue whereas none was detectable in control tissue.

Table 5 also notes whether the gene sequence corresponds to a gene which had previously been identified, and additionally notes in which figure the nucleotide sequence of the given sequence is listed.

TABLE 5

| Gene | ob/ob | db/db | Prev. known | Seq. |
|---|---|---|---|---|
| F49 (SEQ. ID NO:34) | | +Adipose | No | FIG. 14 |
| murine C5* (SEQ. ID NO:36) | ⇑Adipose | ⇑Adipose | No | FIG. 16A–16B |
| L31/F74 (SEQ. ID NO:16) | ⇓Adipose | ⇓Adipose | Yes | FIG. 8 |
| L7/L21 (SEQ. ID NO:18) | ⇑Liver | ⇑Liver | Yes | FIG. 9 |
| L29 (SEQ. ID NO:20) | ⇓Liver | | Yes | FIG. 10 |
| L38 (SEQ. ID NO:22, 43) | ⇑Liver | ⇑Liver | Yes | FIG. 11 |
| L37 (SEQ. ID NO:25, 44–45) | ⇑Liver | | Yes | FIG. 12 |
| L34 (SEQ ID NO:57) | ⇑Liver | | Yes | FIG. 22 |

*The mouse C5 sequence was first identified via sequence homology, as described in the Example presented in Section 10, below. C5 was then subsequently tested in ob and db mice, at which time it was identified to represent a differentially expressed gene sequence.

In addition to the tissues, listed above in Table 5, in which the initial differential expression was observed, further analysis of the tissue distribution of gene expression of the differentially expressed genes has been conducted. Such an analysis consisted of either Northern or RT-PCR studies, or both, as described, above, in Section 8.1. The tissue distribution information obtained for the above-listed genes is reported, above, in Table 1 of Section 5.2.1.

As described above, several of the gene sequences identified via the genetic obesity paradigms of the invention represent previously unknown genes. These include F49 (SEQ ID NO.:34) and C5 (SEQ ID NO.:36).

A putative full length cDNA clone (FIG. 14; SEQ ID NO.:34) corresponding to the entire coding sequence of the fat-specific F49 gene has been isolated utilizing the techniques described, above, in Section 5.1.1.2. Hybridization of F49 nucleotide sequences to genomic DNA of several divergent organisms reveals that the F49 gene is conserved in most mammals, including monkeys and humans, while the gene appears to be absent from chicken and yeast.

The F49 coding sequence predicts a 96 amino acid protein (SEQ ID NO.:35), shown in FIG. 14. The sequence strongly suggests that the F49 gene product is a secreted protein. Take, for example, the F49 gene product hydropathy plot depicted in FIG. 15. The strongly hydrophobic amino-terminal portion of the amino acid sequence is highly suggestive of a signal sequence characteristic of secreted proteins.

A full-length cDNA clone (FIGS. 16A–16B; SEQ ID NO.:36) corresponding to the entire coding sequence of the murine C5 gene has been isolated utilizing the techniques described, above, in Section 5.1.1.2 and in the Example presented, below, in Section 10. The murine C5 coding sequence predicts the protein whose amino acid sequence is shown in FIGS. 16A–16B (SEQ ID NO.:37) This amino acid sequence bears an approximately 50% identity to the mouse brown fat uncoupling protein.

A more detailed discussion of the murine C5 gene and gene product can be found in the Example presented, below, in Section 10, below. A detailed discussion of the cloning and characterization of the human C5 gene and gene product can be found in the Example presented in Section 11, below. The Example presented in Section 12, below, demonstrates that the C5 gene product exhibits uncoupling activity.

Additionally, database searches have revealed that several of the genes identified via the genetic obesity paradigms described herein have previously been identified (see Table 5). For example, L31/F74 (SEQ ID NO.:16) represents the gene encoding the mouse major urinary protein II (FIGS. 8A, 8B); L7/L21 (SEQ ID NO.:18) represents the gene encoding mouse cytochrome c oxidase subunit I (FIG. 9); L29 (SEQ ID NO.:20) represents the gene encoding mouse testosterone 15-α hydroxylase (FIG. 10); L38 (SEQ ID NO.:22, 43) represents the gene encoding mouse 24p3, a lipocalin family member of unknown function (FIG. 11); L37 (SEQ ID NO.:25, 44–45) represents the gene encoding mouse p6-5, a gene which is 86% homologous to rat preproelastase I (FIG. 12); L34 (SEQ ID NO:57; FIG. 22) represents the mouse homolog of a human gene, which will be referred to herein as the "human L34 gene". The human L34 gene, whose sequence can be found in Hou et al. (Hou et al., 1994, In Vitro Cell Dev. Biol. Anim. 30A:111–114, which is incorporated herein by reference in its entirety) was cloned from a hepatoblastoma cell line and encodes a leucine-rich transmembrane protein. The mouse L34 gene exhibits an 82% identity with the human L34 gene at the nucleotide level, and the derived amino acid sequence of the mouse L34 gene product exhibits an 86% identity with the human L34 gene product.

Several of the previously identified genes which these studies have demonstrated to be differentially expressed in obese versus lean control subjects have never before been associated with processes involved in body weight regulation, appetite regulation, or body weight disorders, such as obesity. Among these genes are the genes encoding the mouse major urinary protein II (L31/F74), mouse testosterone 15-α hydroxylase (L29), mouse 24p3 (L38), mouse p6-5 (L37) and human and mouse L34 proteins.

9. EXAMPLE: IDENTIFICATION OF GENES DIFFERENTIALLY EXPRESSED IN RESPONSE TO SET POINT PARADIGMS

In the Example presented in this Section, set point paradigms, as described, above, in Section 5.1.1.1, were utilized to identify gene sequences which are differentially expressed and which may contribute to body weight disorders and/or may be involved in such processes as body weight regulation or appetite modulation.

9.1. MATERIALS AND METHODS

Set point paradigms: 45 male C57B1/6J mice 8 weeks of age were received from Jackson labs. The animals were randomized into 3 groups of 15 mice each, and housed individually on normal mouse chow for 1 week prior to the initiation of the study. Group 1 mice (Control) were maintained on ad lib mouse chow for an additional five days in order to calculate the daily food intake. Group 2 mice (underweight) then received a fraction of normal food intake (60–90%) so as to reduce and maintain their body weight at approximately 80% of control values. Group 3 mice (overweight) were given a cafeteria diet so as to bring their body weights to 125% of control. The three groups of 15 mice each were then sacrificed by $CO_2$ euthanasia and tissues were immediately collected. Body weights of the three groups of 15 mice were taken at the time of sacrifice.

Other procedures: All other tissue collection, RNA isolation, differential display, sequence analysis, and Northern procedures performed in the experiments described in this Section were as described, above, in Section 6.1. RT-PCR quantitative analysis was performed as described, above, in Section 7.1.

9.2. RESULTS

Mice, as described, above, in Section 9.1, were utilized as part of set point paradigms. The mice were weighed at the end of the study, immediately prior to sacrifice.

Upon sacrifice, tissues were collected from the three groups (i.e., Control, Underweight and Overweight) and immediately frozen. The tissues collected were hypothalamus, liver, small intestine, pancreas, stomach, epididymal fat pads, and skeletal muscle. RNA was collected from the tissue samples obtained and was subjected to differential display, as described, above, in Section 9.1.

Utilizing such set point paradigms and differential display techniques, gene sequences L57, F84 and L31/F74, corresponding to known genes, were identified, as summarized in Table 6, below. In addition to differential expression information, Table 6 also notes in which figure nucleotide sequences of the identified genes are listed.

TABLE 6

| Gene | Overweight | Underweight | Previously known | Seq. |
| --- | --- | --- | --- | --- |
| L57 (SEQ. ID NO:29, 46–48) | | ↑Liver | Yes | FIG. 13 |
| F84 (SEQ. ID NO:52, 54) | | ↓Adipose | Yes | FIG. 21 |
| L31/F74 (SEQ. ID NO:16) | | ↓Liver | Yes | FIG. 8 |

Database searches have revealed that the L57 (SEQ ID NO: 29, 46–48) gene sequence corresponds to a previously known gene, the gene encoding the mouse orphan nuclear hormone receptor (FIG. 13) and the F84 (SEQ ID NO: 53, 55) gene sequence encodes mouse cytochrome p450 IID (FIG. 21). As discussed, above, in Section 8.2, the L31/F74 gene sequence encodes the mouse major urinary protein II. Interestingly, these gene products have never before been associated with processes involving body weight or appetite regulation or body weight disorders.

10. EXAMPLE: ISOLATION AND CHARACTERIZATION OF THE MURINE C5 GENE

Described in the Example presented in this Section is the cloning and characterization of the novel murine gene, designated C5. As discussed below, characterization of the novel C5 gene indicates that it can be involved in body weight regulation.

10.1. MATERIALS AND METHODS

Cloning of murine C5. A mouse spleen cDNA library was constructed in the Uni-ZAP vector (Stratagene, La Jolla, Calif.). Random cDNA clones were isolated from the library and sequenced to generate a database of expressed sequence tags (ESTs) that was compared to the Genbank sequence database using the BLASTX algorithm (Altschul S F. et al., 1990, J. Mol. Biol. 215:403–10). This analysis identified an EST that was predicted to encode a peptide with a high level of similarity to the mouse brown fat uncoupling protein. A 1.6 kb cDNA containing the entire mouse C5 open reading frame was isolated from the same library by screening with a $^{32}p$ labeled DNA probe using standard high stringency conditions.

RNA preparation and Northern blotting. Mouse poly A+ RNA blots were obtained from Clontech.

Total RNA was isolated using guanidinium thiocyanate extraction and cesium chloride centrifugation (Sambrook J. et al., Molecular cloning: A laboratory manual. Cold Spring Harbor Laboratory Press, Cold Spring Harbor, N.Y., 1989). Mouse white adipose tissue was obtained from 3–4 animals each of C57BL/6J ob/ob, C57BL/6J +/?, C57BL/KsJ +db/+db or C57BL/KsJ m+/m+ (Jackson Laboratories, Bar Harbor, Me.).

Fifteen μg of total RNA was electrophoresed on a 1.3% agarose/formaldehyde gel and transferred onto nylon membranes. Blots were probed with $^{32}$P-labeled DNA probes using the Rapid-Hyb buffer (Amersham, Arlington Heights, Ill.) according to the manufacturer's instructions.

The relative amounts of C5 and control actin transcripts were quantitated by densitometry and fold-induction was calculated as:

$$[^{amount}C5(ob,db)/^{amount}C5(wt)]\times[^{amount}actin(Wt)/^{amount}actin(ob,db)].$$

10.2 RESULTS

Sequence databases were produced, as described above, in Section 10.1. A database screen for candidate obesity genes identified a partial cDNA clone that was predicted to encode a protein fragment with sequence similarity to a region of the mammalian brown fat uncoupling protein (UCP). A full-length cDNA was then isolated and sequenced, as depicted in FIGS. 16A–16B. The deduced amino acid sequence of the encoded protein (FIGS. 16A–16B) showed 56% identity to the known mouse UCP throughout its length, as shown in FIG. 17A. The degree of sequence similarity between UCP and C5 ranges from 56–60%, depending on the species. Many of the non-identical amino acids are conservative substitutions and correspond to residues showing variation among the known uncoupling proteins from various mammalian species (Kuan & Saier, 1993, Crit. Rev. Biochem. Mol. Biol. 18:209–233, 1993). Thus, the novel C5 amino acid sequence indicated that the gene product could have uncoupling protein activity. As demonstrated in the Example presented, below, in Section 12, the C5 protein does, indeed, exhibit uncoupling activity.

Several other proteins showing more limited similarity to UCP have been identified previously, all of which are known or suspected to be mitochondrial inner membrane transporters. These proteins include the ATP/ADP transporter, the phosphate transporter, and the oxaloacetate transporter (Kuan & Saier, 1993, Crit. Rev. Biochem. Mol. Biol. 18:209–233, 1993; Walker & Runswick, 1993, J. Bioenergetics Biomembranes 25:435–446). Sequence alignment of these related transporters with UCP shows a much lower degree of homology than observed between UCP and C5 (Table 7, below).

TABLE 7

Amino Acid Identities (%) between
Members of the Mitochondrial Carrier Family

|          | UCP  | C5   | Phosph. | Oxoglut. | ATP/ADP |
|----------|------|------|---------|----------|---------|
| UCP      | —    | 56.3 | 16.8    | 29.7     | 19.2    |
| C5       | 56.3 | —    | 19.4    | 30.6     | 22.5    |
| Phosphate| 16.8 | 19.4 | —       | 22.0     | 18.7    |
| Oxoglut. | 29.7 | 30.6 | 22.0    | —        | 23.5    |
| ATP/ADP  | 19.2 | 22.5 | 18.7    | 23.5     | —       |

Sequence comparisons were done using ALIGN program (Myers & Miller, 1988, CABIOS 4:11–17). Sequences used were murine UCP (Genbank Acc. No. P12242), murine C5 (SEQ ID NO:37), rate phosphate carrier (Genbank Acc. No. P16036), human oxoglutarate/malate carrier (Q02978), and murine ATP/ADP carrier (Genbank Acc. No. 423368).

As shown in Table 7, above, the amino acid identities between UCP or C5 and these transporters ranged from about 17% to 31%, significantly lower than the 56% identity observed between UCP and C5. This further indicated that the C5 protein may not only be a mitochondrial inner membrane transport protein, but may be represent an uncoupling protein with weight regulatory and thermogenic properties.

The tissue distribution of murine C5 was examined by Northern analysis (2 μg poly-A+ mRNA per lane). Unlike UCP, which is expressed specifically in brown adipose tissue, C5 was found to be expressed in a variety of tissues. Specifically, C5 was found to be expressed at low levels in most tissues examined (heart, brain, spleen, lung, liver, muscle, kidney and testis).

To test whether the C5 gene product was regulated by obesity, total RNA was isolated from the white adipose tissue of ob/ob mice, db/db mice and their lean littermate controls. First, C5 mRNA was easily detectable in the white adipose tissue of the ob/ob, db/db as well as the lean littermate controls on total RNA Northern blots, indicating that in the mouse, white adipose tissue is a major source of C5.

Further, there was a clear 4–6 fold increase in steady state C5 transcript levels in ob/ob and db/db mice relative to lean littermate controls. Given the uncoupling activity of C5 (see the Example presented, below, in Section 12), increased C5 expression would be expected to decrease rather than increase body weight. It is proposed, therefore, that the upregulation of C5 expression, observed in ob/ob and db/db mice is a compensatory change in which C5 induction represents an attempt counteract the powerful genetically induced obesity.

As described, above, C5 mRNA levels are upregulated in two genetic models of obesity, indicating a role for C5 in body weight regulation. These differential expression results are summarized in the Example presented in Section 8, above.

11. EXAMPLE: ISOLATION AND CHARACTERIZATION OF THE HUMAN C5 GENE

Described in the Example presented in this Section, is the cloning and characterization of a human homologue of the mouse C5 gene, a gene whose product is involved in body weight disorders, and/or processes involved in body weight or appetite regulation. Likewise, human C5 can also represent a gene whose product is involved in such disorders and/or processes in humans.

11.1. MATERIALS AND METHODS

Cloning of human C5. Truncated human C5 was isolated from a human fetal spleen library (Stratagene). The probe used for the hybridization was a 0.9 kb partial cDNA clone of the mouse C5 gene. Filters used for hybridization were NitroPlus 2000 (Micron Separations, Inc.). Hybridization and washing conditions were as per manufacturer's instructions for low stringency hybridizations, except that the hybridization steps were carried out at 42° C.

The 5'-end of the human C5 cDNA was identified by 5'-RACE using a commercially available RACE kit and human skeletal muscle 5'-RACE-ready cDNA (Clontech Laboratories, Palo Alto, Calif.). The full-length human C5 cDNA was constructed by inserting the 5' RACE product into the original 5'-truncated human C5 clone using standard molecular biology techniques.

RNA preparation and Northern blotting. Human poly A+ RNA blots were obtained from Clontech. Total RNA was isolated using guanidinium thiocyanate extraction and cesium chloride centrifugation (Sambrook J. et al., Molecular cloning: A laboratory manual. Cold Spring Harbor Laboratory Press, Cold Spring Harbor, N.Y., 1989) from the following tissues: human skeletal muscle and white adipose tissue was obtained from a non-diabetic male with normal body weight (body mass index: 22.8) who had undergone surgery for coronary artery disease. Fifteen μg of total RNA was electrophoresed on a 1.3% agarose/formaldehyde gel and transferred onto nylon membranes. Blots were probed with $^{32}$P-labeled DNA probes using the Rapid-Hyb buffer (Amersham, Arlington Heights, Ill.) according to the manufacturer's instructions.

11.2. RESULTS

The mouse C5 gene sequence was used, in conjunction with the methods taught, above, in Sections 5.2.1 and 11.1, to isolate a cDNA clone corresponding to human C5. The nucleotide sequence of the human C5 cDNA clone is shown in FIGS. 18A–18B (SEQ ID NO:38). FIGS. 18A–18B also depicts the human C5 amino acid sequence (SEQ ID NO:51).

The amino acid sequences between mouse and human C5 are 95% identical (FIG. 17B). The degree of amino acid identity between mouse and human C5 is even higher than the one observed between mouse and human UCP (79%; Kozak C P. et al., 1988, J. Biol. Chem. 262:1274–1277; Cassard A M. et al., 1990, J. Cell Biochem. 43:255–64). This high degree of amino acid identity, which was also reflected at the nucleotide level, strongly argued that the isolated cDNA encoded the human C5 protein.

The tissue distribution of human C5 was examined by Northern analysis (as shown in FIG. 19A, with 2 μg poly-A+ mRNA per lane, and in FIG. 19B, with 15 μg total RNA per lane). Low levels of human C5 mRNA were detectable by poly-A+ mRNA Northern blots in most tissues including heart, placenta, lung, liver, kidney, and pancreas.

Interestingly, much higher levels of C5 mRNA were present in skeletal muscle, an important thermogenic organ in humans (see, e.g., Jensen M. D. et al., 1995, Am. J. Physiol. 268:E433–438; Astrup A. et al., 1989, Am. J. Physiol. 257:E340–E345, 1989; Simonsen L. et al., 1992, Am. J. Physiol. 263:E850–E855; Simonsen J. et al., 1993, Int. J. Obes. Relat. Metab. Disord. 17(Suppl. 3):S47–51). Analysis of total RNA Northern blots revealed that the level of C5 transcript in white adipose tissue exceeded even that found in muscle.

The differences in expression observed between mice and humans may be partly due to the relative importance of these tissues to the overall thermogenesis of the organism: in mice, the majority of regulated thermogenesis is thought to be mediated via the brown fat with other tissues playing a more minor role (Cannon and Nedergaard, 1985, Essays in Biochem. 20:110–165; Himms-Hagen J., 1989, Prog. Lipid Res. 28:67–115; Block B A., 1994, Annu. Rev. Physiol. 56:535–577), while in adult humans the majority of regulated thermogenesis is thought to take place in muscle and, to a lesser extent, in white fat (Jensen M D. et al., 1995, Am. J. Physiol. 268:E433–438; Astrup A. et al., 1989, Am. J. Physiol. 257:E340–E345, 1989; Simonsen L. et al., 1992, Am. J. Physiol. 263:E850–E855; Simonsen J. et al., 1993, Int. J. Obes. Relat. Metab. Disord. 17 (Suppl. 3):S47–51). Thus, the presence of high levels of C5 transcript in human muscle and white fat is consistent with a role for C5 in mediating thermogenesis in humans.

12. EXAMPLE: THE C5 GENE PRODUCT UNCOUPLES OXIDATIVE PHOSPHORYLATION

The Example presented herein demonstrates that the C5 gene product exhibits uncoupling activity, i.e., is capable of uncoupling oxidative phosphorylation. An uncoupling activity or property refers to an ability of the gene product to transport protons across the mitochondrial inner membrane, thereby reducing proton motive force and allowing caloric energy to be dissipated in the form of heat. These results, together with the C5 tissue distribution data presented in Sections 10 and 11, above, strongly indicate that C5 acts as a mediator of thermogenesis and a regulator of mammalian body weight.

12.1 MATERIALS AND METHODS

Expression of UCP and C5 in *S. cerevisiae*. Yeast media were prepared and yeast molecular biology techniques were performed as described (Kaiser C. et al., Cold Spring Harbor Laboratory Press, Cold Spring Harbor, N.Y., 1994). Proteins were expressed in either the W303 genetic background (RGY12: MATa/α ura3-1/ura3-1 leu2-3,112/leu2-3,112 his3-11,15/his-11,15 trp1-1/TRP1 ade2-100/ADE2 can1-100/can1-100/can1-100 Gal$^+$; constructed from strains obtained from Whitehead Institute, Boston, Mass.) or the S288C genetic background (CKY8: MATα ura3-52 leu2-3, 112 Gal$^-$). Murine UCP or murine C5 were expressed from the GAL1 promoter in pYES2 (URA3, 2μ; Invitrogen, San Diego, Calif.) using a gap repair strategy (Orr-Weaver T L. et al., 1983, Methods Enzymol. 101:228–245).

PCR primers were designed that amplified the open reading frame of UCP or C5 fused to 30 nucleotides of the GAL1 promoter (nucleotide −35 to −5) at the 5' end and to 30 nucleotides of the CYC1 terminator at the 3' end. PCR products were cotransformed with linearized pYES2 (digested with HindIII and XbaI) into CKY8, plasmids were recovered from several transformants and analyzed by restriction digestion and DNA sequencing. Typically, greater than 80% of transformants contained plasmids with the expected inserts. Strains used for functional assays were generated by retransforming a plasmid whose entire insert sequence had been confirmed by DNA sequencing into CKY8 and RGY12.

Deletion mutants lacking amino acids 268–270 of murine UCP (UCPΔ3) or amino acids 270–272 of murine C5 (UCPHΔ3) were constructed by site-directed mutagenesis (Kunkel T A. et al., 1987, Methods Enzymol. 154:367–382). Mutants were fused to the GAL1 promoter in pYES2 as described above, verified by DNA sequencing and expressed in CKY8 or RGY12.

For growth assays, strains were pregrown overnight on synthetic complete (SC) medium lacking uracil and supplemented with 2% glucose. To induce expression from the GAL1 promoter, strains were plated onto SC medium lacking uracil and supplemented either with 2% raffinose and 2% galactose (anaerobic growth) or with 3% glycerol and 2% galactose (aerobic growth). Growth was assayed at 30° C. either under normal atmospheric conditions or in an anaerobic chamber (BBL Gas Pak Pouch, Becton Dickinson, Cockeysville, Md.).

For measurements of the mitochondrial membrane potential, strains were pregrown in SC medium lacking uracil and supplemented with 2% raffinose. At a density of $4 \times 10^6$ cells/ml, galactose was added to 2% and strains were allowed to grow for an additional 5 hours. The cell concentration was then adjusted to $2 \times 10^6$ cells/ml, 3,3'-dihexyloxacarbocyanine iodide (DiOC$_6$; Sigma, St. Louis, Mo.) was added to a final concentration of 10 ng/ml, and fluorescence was measured 10–30 min later in a fluorescence activated cell sorter (FACSCalibur; Becton Dickinson). Where indicated, 200 μM of the chemical uncoupler carbonyl cyanide m-chlorophenylhydrazone (CCCP; Sigma) was added 5 min before addition of DiOC$_6$.

A total of 10,000 objects were counted for each analysis. Dead cells were identified by staining with propidium iodide (2 μg/ml final concentration; Molecular Probes, Eugene, Oreg.), and represented less than 2% of cells in all samples assayed. Debris and clumped cells were identified by forward and side scatter, and were excluded from the analysis. Analysis was performed using the CellQuest software (Becton Dickinson).

12.2. RESULTS

To test whether the C5 gene product exhibits uncoupling properties, the mouse UCP and C5 proteins were expressed in yeast and their ability to inhibit aerobic growth was compared. An uncoupling property refers to an ability of the gene product to transport protons across the mitochondrial inner membrane, thereby reducing proton motive force and allowing caloric energy to be dissipated in the form of heat (Klingenberg M., 1990, Trends Biochem. Sci. 15:108–11; Klaus S. et al., 1991, Int. J. Biochem. 23:791–801).

The uncoupling properties of UCP had previously been studied in yeast expressing mammalian UCP by measuring defects in aerobic growth (Bathgate B. et al., 1992, Mol. Microbiol. 6:363–370) and by detecting decreases in the mitochondrial membrane potential using potential-sensitive dyes such as DiOC$_6$ (Bouillaud F. et al., 1994, EMBO J. 13:1990–1997). Techniques such as these were used in the present study, as described, above, in Section 12.1.

Proteins were expressed from the strong, inducible GAL1 promoter in two different yeast genetic backgrounds (W303 and S288C). C5 was expressed at levels similar to UCP in both strain backgrounds, as judged by Western blotting of C-terminally myc-tagged variants of UCP and C5.

When grown on media where ATP is derived primarily by aerobic respiration (3% glycerol/2% galactose, under normal atmospheric conditions; Pon & Schatz, in, The Molecular and Cellular Biology of the Yeast Saccharomyces, vol. 1, Broach J. R. et al., eds., Cold Spring Harbor Laboratory Press, Cold Spring Harbor, N.Y., 1991; Johnston & Carlson, in, The Molecular and Cellular Biology of the Yeast Saccharomyces, vol. 2, Jones E. W. et al., eds., Cold Spring Harbor Laboratory Press, Cold Spring Harbor, N.Y., 1992), RGY12 and CKY8 strains expressing C5 had a dramatically reduced growth rate relative to strains containing expression vector only. The extent of growth inhibition by C5 was similar to that observed with the known UCP.

To control for the possibility that the growth inhibition was due to non-specific toxicity, as opposed to a disruption of aerobic respiration, the same yeast strains were examined under conditions of anaerobic growth (2% raffinose/2% galactose, in an anaerobic chamber). Under these conditions, strains containing vector only and strains expressing C5 or UCP grew equally well. Because growth inhibition was not observed in yeast cells grown anaerobically, the growth inhibition was, therefore, due to a specific disruption of respiration, rather than generalized toxicity. Thus, C5, like UCP, specifically affects growth under aerobic conditions, consistent with a dissipation of the proton motive force by C5.

To demonstrate more directly that the C5 protein can dissipate the proton motive force, tests were conducted regarding the comparative ability of yeast strains expressing C5, UCP, or vector alone, to be stained by a florescent dye ($DiOC_6$). $DiOC_6$ is sensitive to the electrochemical gradient across the mitochondrial inner membrane (Pon & Schatz, in The Molecular and Cellular Biology of the Yeast Saccharomyces, vol. 1, Broach J. R. et al., eds., Cold Spring Harbor Laboratory Press, Cold Spring Harbor, N.Y., 1991; Pringle J. R. et al., 1989, Methods Cell Biol. 31:357–435). As discussed below and depicted in FIGS. 23A and 23B, C5 expression disrupts the proton gradient across the mitochondrial membrane to a similar or an even larger extent than UCP expression. Such a decrease in mitochondrial membrane potential, together with the growth phenotypes, demonstrates that C5 has uncoupling activity.

A previous study showed that while wild-type UCP expressed in yeast does not affect $DiOC_6$ staining, a three amino acid deletion in the putative nucleotide binding site of UCP (UCPΔ3, lacking amino acids 268–270) leads to activation of UCP and a significant decrease in the mitochondrial membrane potential of the host strain (Bouillaud F. et al., 1994, EMBO J. 13:1990–1997).

The equivalent deletion in C5 (UCPHΔ3, lacking amino acids 270–272) was compared. UCPΔ3, and to a lesser extent UCP, decreased $DiOC_6$ staining (FIGS. 23A, 23B). The difference between UCP and UCPΔ3 was more pronounced in the S288C background (FIG. 23A), but was also detectable in the W303 background (FIG. 23B).

Expression of both wild-type C5 and the UCPHΔ3 mutant decreased the mitochondrial membrane potential to a similar or even larger extent compared to UCPΔ3 in both backgrounds examined (FIGS. 23A, 23B). The effects of C5 or UCPHΔ3 expression were most obvious in the W303 genetic background; in this background, a portion of the cells showed a complete dissipation of the mitochondrial membrane potential (FIG. 23B).

As discussed above, C5 was found to have more pronounced effects in the dye staining assay than UCP. This difference could reflect a higher specific activity of C5 compared to UCP, or it could indicate that the activity of the two proteins is regulated differently. A single amino acid mutation in the inhibitory nucleotide binding site of UCP ($Phe_{268}$ to Tyr) creates a UCP molecule that has higher uncoupling activity in the dye-staining assay (Bouillaud F. et al., 1994, EMBO J. 13:1990–1997); both mouse and human C5 naturally contain a tyrosine at the equivalent position ($Tyr_{270}$), and may thus be less susceptible to the inhibitory effects of nucleotides. Furthermore, the extreme C-terminus of UCP, a region that has been implicated in regulation of UCP activity by fatty acids (Gonzalez-Barioso M M. et al., 1996, Eur. J. Biochem. 239:445–450), is less well conserved between C5 and UCP, possibly resulting in differences in regulation.

In summary, these data demonstrate that the C5 gene product exhibits substantial uncoupling activity, indicating that C5 is involved in the thermogenesis process, a process known to be important in the regulation of mammalian body weight. Thus, these data indicate that the C5 gene product can be involved in the regulation of mammalian body weight.

13. DEPOSIT OF MICROORGANISMS

The following microorganisms were deposited with the Agricultural Research Service Culture Collection (NRRL), Peoria, Ill., on Aug. 23, 1994 and assigned the indicated accession numbers:

| Microorganism | NRRL Accession No. |
| --- | --- |
| famf049a | B-21318 |
| fahs005a | B-21320 |

The following microorganism was deposited with the American Type Culture Collection (ATCC), Rockville, Md., on Feb. 7, 1997 and assigned the indicated accession number:

| Microorganism | ATTC Accession No. |
| --- | --- |
| fahs005a2 | 98319 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for identifying a compound that modulates C5 gene expression, comprising:
   (a) contacting a test compound to a cell that expresses a C5 gene;
   (b) measuring the level of C5 gene expression in the cell; and
   (c) comparing the level obtained in (b) to C5 gene expression level obtained in the absence of test compound;
   such that if the level obtained in (b) differs from that obtained in the absence of test compound, a compound that modulates C5 gene expression has been identified.

2. The method of claim 1 wherein the test compound increases the level of C5 gene expression.

3. The method of claim 1 wherein the test compound decreases the level of C5 gene expression.

4. The method of claim 1 wherein the test compound comprises a small organic molecule.

* * * * *

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
            (A) LENGTH: 253 base pairs
            (B) TYPE: nucleic acid
            (C) STRANDEDNESS: single
            (D) TOPOLOGY: linear (xi) SEQUENCE DESCRIPTION: SEQ ID NO:1:

GGGCAGTACA ACCAGATCCA CTTTTATTAG GAACAAATAC AATCTCAATC AGTACAAGTA      60

GGCTTCAAGA GTTGATATTA ATGGAAATCA TCCAAATTAC ACTTGGGTCA CAAATAATTA     120

CCCCACATAA AAAGGGAAAA AAAAAATCTC ATTCAGGGGA AGGGAAAGGT TTCCTGCAAT     180

GGTTTTCATG GCAGTGGGTA GGTAGTCTTG CACTTTGGAC TGGTCATATC TGTCAGTCTC     240

TGGGCAGAGC AAA                                                       253

(2) INFORMATION FOR SEQ ID NO:2:

(i) SEQUENCE CHARACTERISTICS:
            (A) LENGTH: 156 base pairs
            (B) TYPE: nucleic acid
            (C) STRANDEDNESS: single
            (D) TOPOLOGY: linear (xi) SEQUENCE DESCRIPTION: SEQ ID NO:2:

CCTGAATGAG ATTTTTTTTT TCCCTTTTTA TGTGGGGTAA TTATTTGTGA CCCAAGTGTA      60

ATTTGGATGA TTTCCATTAA TATCAACTCT TGAAGCCTAC TTGTACTGAT TGAGATTGTA     120

TTTGTTCCTA ATAAAAGTGG ATCTGGTTGT ACTGTC                              156

(2) INFORMATION FOR SEQ ID NO:3:

(i) SEQUENCE CHARACTERISTICS:
            (A) LENGTH: 95 base pairs
            (B) TYPE: nucleic acid
            (C) STRANDEDNESS: single
            (D) TOPOLOGY: linear (xi) SEQUENCE DESCRIPTION: SEQ ID NO:3:

CAAAGTGCAA GACTACCTAC CCACTGCCAT GAAAACCATT GCAGGAAACC TTTCCCTTCC      60

TGAATGAGAT TTTTTTTTTC CCTTTTTATG TGGGG                                95

(2) INFORMATION FOR SEQ ID NO:4:

(i) SEQUENCE CHARACTERISTICS:
            (A) LENGTH: 92 base pairs
            (B) TYPE: nucleic acid
            (C) STRANDEDNESS: single
            (D) TOPOLOGY: linear (xi) SEQUENCE DESCRIPTION: SEQ ID NO:4:

CCCTTCCAAT ACAAGAACTA AGTGGACTAG ACTTCCAGTG ATCCCTCTCC CAGCTCTTCC      60

CTTTCCCAGT TGTCCCCACT GTAACTCAAA AG                                   92

(2) INFORMATION FOR SEQ ID NO:5:

(i) SEQUENCE CHARACTERISTICS:
            (A) LENGTH: 92 base pairs
            (B) TYPE: nucleic acid
            (C) STRANDEDNESS: single
            (D) TOPOLOGY: linear (xi) SEQUENCE DESCRIPTION: SEQ ID NO:5:

CCCTTCCAAT ACAAGAACTA AGCAGACTAG ACTTCCAGTG ATCCCTCTCC CAGCTCTTCC      60

CTCTCCCAGT TGTCCCCACT GTAACTCAAA GG                                   92

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:6:

```
AAAGGATGGA ATACCAAGGT CTTTTTATTC TTCGTGCCAA AAAAAAGA            48
```

(2) INFORMATION FOR SEQ ID NO:7:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO:7:

```
ATCTCTTTTG GCAGAACATG AATGCAGGTC ACCTGGTGTC AATACTCAGC CAGGCTGAGA    60

GCAACTTGGT GGCCTCGCTG GTTAAGGAGA GTGGTACTAC AGCTTCCAAT GTCTGGACTG   120

GACTTCATGA CCCTAAAAGT                                               140
```

(2) INFORMATION FOR SEQ ID NO:8:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO:8:

```
AGCTCTTTTG CCAGAACATG AATGCAGGTC ACCTGGTGTC AATACTCAGC CAGGCTGAGA    60

GCAACTTTGT GGCCTCGCTG GTTAAGGAGA GTGGTACTAC AGCTTCCAAT GTCTGGACTG   120

GACTTCATGA CCCTAAAAGT                                               140
```

(2) INFORMATION FOR SEQ ID NO:9:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:9:

```
AACCGTCGTT GGCACTGGAG CAGTGGCTCC CTATTTCTCT TCAAGTCATG GGCCACTGGA    60

GCTCCAAGCA CTGCCAACCG TGGT                                           84
```

(2) INFORMATION FOR SEQ ID NO:10:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:10:

```
AACGCCTATG GTTCCTACTG TTATTATCTA ATTGAAGACC GTTTGACCTG GGGGGAGGCT    60

GATGT                                                                65
```

(2) INFORMATION FOR SEQ ID NO:11:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:11:

```
AGCATACAAA AAATGGAAGG ACGAAAACTG TGAGGCACAG TACTCCTTTG TCTGCAAGTT      60

CAGAGCCTAA                                                            70
```

(2) INFORMATION FOR SEQ ID NO:12:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (xi) SEQUENCE DESCRIPTION: SEQ ID NO:12:

```
GGCTTAGTCA GCCACTTTAC AGACTGGTCT TCCTGCTGGC ACATACTGTG ATGTCATCTC      60

TGGAGATAAG GTCGATGGCA ATTGCACTGG ACTTAGAGTG AATGTTGGCA GTGATGGCAA     120

AGCTCACTTT TCCATTAGTA ACTCTGCTGA GGACCCATTT ATTGCAATCC ATGCTGACTC     180

AAAATTGTAA GAATCTATAT TAAAGAGATT TGGATTAGGA A                        221
```

(2) INFORMATION FOR SEQ ID NO:13:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (xi) SEQUENCE DESCRIPTION: SEQ ID NO:13:

```
GGCTTTGTCA GCCACTTTAC AGACTGGTCT TCCTGCTGGC ACATACTGTG ATGTCATCTC      60

TGGAGATAAG GTCGATGGCA ATTGCACTGG ACTTAGAGTG AATGTTGGCA GTGATGGCAA     120

AGCTCACTTT TCCATTAGTA ACTCTGCTGA GGACCCATTT ATTGCAATCC ATGCTGACTC     180

AAAATTGTAA GAATCTATAT TAAAGAGATT TGGATTAAGC A                        221
```

(2) INFORMATION FOR SEQ ID NO:14:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO:14:

```
AGAGTCAAGG GCTAGTGCGC ACCGCAGCCA GCGCCCAGTA CCGTGGCGTT CTGGGTACCA      60

TCCTAACCAT GGTGCGCACT GAGGGTCCAC GCAGCCTCTA CAATGGGCTG GTCGCCGGCC     120

TGCAGCGCCA GATGAGCCTT GCCTCCGTCC GCATTGGCCT CTACGACTCT GTCAAACAGT     180

TCTACACCAA GGGCTCAGAG CATGGAGGCA TCGGGAGCCG CCTCCTGGCA GGTAGCACCA     240

CAGGTGCCCT GGCCGTGGTT GTAGCCCAGC CTACAGATGT GGTAAAGGTC CGCTTCCAGG     300

CTCCAGGCC                                                            309
```

(2) INFORMATION FOR SEQ ID NO:15:

(i) SEQUENCE CHARACTERISTICS:

(A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO:15:

AGATCCAAGG CGAGTTCCCG ATCACCAGCG GCATCAGGTA CAAAGGTGTC CTGGGGACAA      60

TCACCACCCT GGCAAAAACG GAAGGGCCCC TGAAACTCTA CAGCGGGTTG CCCGCCGGCC     120

TCCAGAGACA AATCAGCTTC GCCTCGCTCA GGATCGGCCT CTACGACACG GTGCAGGAGT     180

TCTTCACCTC GGGGGAAGAA ACACCGAGTT TAGGAAGCAA GATCTCGGCC GGCCTAACAA     240

CTGGAGGCGT GGCGGTGTTC ATCGGGCAGC CCACAGAGGT CGTGAAAGTC AGGCTGCAAG     300

CGCAGAGCC                                                             309

(2) INFORMATION FOR SEQ ID NO:16:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (xi) SEQUENCE DESCRIPTION: SEQ ID NO:16:

AAGATGCTGC TGCTGCTGCT GTGTTTGGGA CTGACCCTAG TCTGTGTCCA TGCAGAAGAA      60

GCTAGTTCTA CGGGAAGGAA CTTTAATGTA GAAAAGATTA ATGGGAATG GCATACTATT     120

ATCCTGGCCT CTGACAAAAG AGAAAAGATA GAAGATAATG GCAACTTTAG ACTTTTTCTG     180

GAGCAAATCC ATGTCTTGGA GAAATCCTTA GTTCTTAAAA TCCATCCTGT AAGAGATGAA     240

GAGTGCTCCG AATTATCTAT GGTTGCTGAC AAAACAGAAA AGGCTGGTGA ATATTCTGTG     300

ACGTATGATG GATTCAATAC ATTTACTATA CCTAAGACAG ACTATGATAA CTTTCTTATG     360

GCTCATCTCA TTAACGAAAA GGATGGGGAA ACCTTCCAGC TGATGGGGCT CTATGGCCGA     420

GAACCAGATT TGAGTTCAGA CATCAAGGAA AGGTTTGCAC AACTATGTGA GGAGCATGGA     480

ATCCTTAGAG AAAATATCAT TGACCTATCC AATGCCAATC GCTGCCTCCA GGCCCGAGAA     540

TGAAGATTGG CCTGAGCCTC CAGTGTTGAG TGGAGACTTC TCACCAGGAC TCCACCATCA     600

TCCCTTCCTA TCCATACAGC ATCCCCAGTA TAAATTCTGT GATCTGCATT CCATCCTGTC     660

TCACTGAGAA GTCCAATTCC AGTCTATCCA CATGTTACCT AGGATACCTC ATCAAGAATC     720

AAAGACTTCT TTAAATTTCT CTTTGATATA CCCATGACAA TTTTTCATGA ATTTCTTCCT     780

CTTCCTGTTC AATAAATGAT TACCCTTGCA CTTA                                  814

(2) INFORMATION FOR SEQ ID NO:17:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (xi) SEQUENCE DESCRIPTION: SEQ ID NO:17:

ATGAAGATGC TGCTGCTGCT GTGTTTGGGA CTGACCCTAG TCTGTGTCCA TGCAGAAGAA      60

GCTAGTTCTA CGGGAAGGAA CTTTAATGTA GAAAAGATTA ATGGGAATG GCATACTATT     120

ATCCTGGCCT CTGACAAAAG AGAAAAGATA GAAGATAATG GCAACTTTAG ACTTTTTCTG     180

GAGCAAATCC ATGTCTTGGA GAAATCCTTA GTTCTTAAAT TCCATACTGT AAGAGATGAA     240

GAGTGCTCCG AATTATCTAT GGTTGCTGAC AAAACAGAAA AGGCTGGTGA ATATTCTGTG     300

```
ACGTATGATG GATTCAATAC ATTTACTATA CCTAAGACAG ACTATGATAA CTTTCTTATG     360

GCTCATCTCA TTAACGAAAA GGATGGGGAA ACCTTCCAGC TGATGGGGCT CTATGGCCGA     420

GAACCAGATT TGAGTTCAGA CATCAAGGAA AGGTTTGCAA AACTATGTGA GGAGCATGGA     480

ATCCTTAGAG AAAATATCAT TGACCTATCC AATGCCAATC GCTGCCTCCA GGCCCGAGAA     540

TGAAGAATGG CCTGAGCCTC CAGTGTTGAG TGGAGACTTC TCACCAGGAC TCCACCATCA     600

TCCCTTCCTA TCCATACAGC ATCCCAGTA TAAATTCTGT GATCTGCATT CCATCCTGTC      660

TCACTGAGAA GTCCAATTCC AGTCTATCCA CATGTTACCT AGGATACCTC ATCAAGAATC     720

AAAGACTTCT TTAAATTTCT CTTTGATATA CCCATGACAA TTTTTCATGA ATTTCTTCCT     780

CTTCCTGTTC AATAAATGAT TACCCTTGCA CTTA                                 814

(2) INFORMATION FOR SEQ ID NO:18:

(i) SEQUENCE CHARACTERISTICS:
         (A) LENGTH: 277 base pairs
         (B) TYPE: nucleic acid
         (C) STRANDEDNESS: single
         (D) TOPOLOGY: linear (xi) SEQUENCE DESCRIPTION: SEQ ID NO:18:

TGACCCGTAC TTATTACAGC CGTACTGCTC CTATTATCAC TACCAGTGCT AGCCGCAGGC      60

ATTACTATAC TACTAACAGA CCGCAACCTA AACACAACTT TCTTTGATCC CGCTGGAGGA     120

GGGGACCCAA TTCTCTACCA GCATCTGTTC TGATTCTTTG GGCACCCAGA AGTTTATATT     180

CTTATCCTCC CAGGATTTGG AATTATTTCA CATGTAGTTA CTTACTACTC CGGAAAAAAA     240

GAACCTTTCG GCTATATAGG AATAGTATGA AAAAAA                               277

(2) INFORMATION FOR SEQ ID NO:19:

(i) SEQUENCE CHARACTERISTICS:
         (A) LENGTH: 277 base pairs
         (B) TYPE: nucleic acid
         (C) STRANDEDNESS: single
         (D) TOPOLOGY: linear (xi) SEQUENCE DESCRIPTION: SEQ ID NO:19:

TGATCCGTAC TTATTACAGC CGTACTGCTC CTATTATCAC TACCAGTGCT AGCCGCAGGC      60

ATTACTATAC TACTAACAGA CCGCAACCTA AACACAACTT TCTTTGATCC CGCTGGAGGA     120

GGGGACCCAA TTCTCTACCA GCATCTGTTC TGATTCTTTG GGCACCCAGA AGTTTATATT     180

CTTATCCTCC CAGGATTTGG AATTATTTCA CATGTAGTTA CTTACTACTC CGGAAAAAAA     240

GAACCTTTCG GCTATATAGG AATAGTATGA GCAATAA                              277

(2) INFORMATION FOR SEQ ID NO:20:

(i) SEQUENCE CHARACTERISTICS:
         (A) LENGTH: 251 base pairs
         (B) TYPE: nucleic acid
         (C) STRANDEDNESS: single
         (D) TOPOLOGY: linear (xi) SEQUENCE DESCRIPTION: SEQ ID NO:20:

TTGTTGCGAT CCCACCAACC TACACTATGA GTTTCTTGTC CCGTTGATCC TGGGCTGCAT      60

GAGGTTAAAG GGAATGATTG AGACCAGACA AGTCAGGGGT TGAAACTTAG AAAAGGTCAA     120

AGGTACAGAA GAAACAGAGG ACACTTCGTA GACTTGCAGA GGATATTTCA AAGGTAGCCA     180

GAGAAGGGGG AAATTATACT ATGTTGTCAA TAGGAATAAT AAAATAATAA AAGTAGATAT     240
```

-continued

TATTTATGGA A                                                                251

(2) INFORMATION FOR SEQ ID NO:21:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (xi) SEQUENCE DESCRIPTION: SEQ ID NO:21:

TTGTCACGAT CCCACCAACC TACACTATGA GTTTCTTGTC CCGTTGATCC TGGGCTGCAT         60

GAGGTTAAAG GGAATGATTG AGACCAGACA AGTCAGGGGT TGAAACTTAG AAAAGGTCAA        120

AGGTACAGAA GAAACAGAGG ACACTTCGTA GACTTGCAGA GGATATTTCA AAGGTAGCCA        180

GAGAAGGGGG AAATTATACT ATGTTGTCAA TAGGAATAAT AAAATAATAA AAGTAGATAT        240

TATTTATGGC A                                                             251

(2) INFORMATION FOR SEQ ID NO:22:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (xi) SEQUENCE DESCRIPTION: SEQ ID NO:22:

GGTKGTTGAG TGTGGCTGAC TGGGATGCGC AGAGACCCAA TGGTTCAGGC GCTGCCTGTC         60

TGTCTGCCAC TCCATCTTTC CTGTTGCCAG AGAGCCACCT GGCTGCCCCA CCAGCCACCA        120

TACCAAGGAG CATCTGGAGC CTCTTCTTAT TTGGCCAGCA CTCCCCATCC ACCTGTCTTA        180

ACACCACCAA TGGCGTCCCC TTTCTGCTGA ATAAATACAT GCCCCC                      226

(2) INFORMATION FOR SEQ ID NO:23:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (xi) SEQUENCE DESCRIPTION: SEQ ID NO:23:

GGGTGGTGAG TGTGGCTGAC TGGGATGCGC AGAGACCCAA TGGTTCAGGC GCTGCCTGTC         60

TGTCTGCCAC TCCATCTTTC CTGTTGCCAG AGAGCCACCT GGCTGCCCCA CCAGCCACCT        120

ACCAAGGAGC ATCTGGAGCC TCTTCTTATT TGGCCAGCAC TCCCCATCCA CCTGTCTTAA        180

CACCACCAAT GGCGTCCCCT TTCTGCTGAA TAAATACATG CCCCC                       225

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:24:

CCGACCAATG CATTGACAAC TGAATGGGTG GT                                      32

(2) INFORMATION FOR SEQ ID NO:25:

(i) SEQUENCE CHARACTERISTICS:
        (A) LENGTH: 155 base pairs (B) TYPE: nucleic acid
            (C) STRANDEDNESS: single
            (D) TOPOLOGY: linear (xi) SEQUENCE DESCRIPTION: SEQ ID NO:25:

TCCGCTCTGG ATGCCAGGGT GATTCTGGGG GACCCCTCCA CTGCATGGTG AACGGTCAGT      60

ATGCTGTCCA CGGAGTGACC AGCTTTGTGT CCAGCATGGG CTGTAATGTC GCCAGGAAGC     120

CCACCGTCTT CACCAGAGTC TCTGCTTACA TTTTC                                155

(2) INFORMATION FOR SEQ ID NO:26:

(i) SEQUENCE CHARACTERISTICS:
            (A) LENGTH: 155 base pairs
            (B) TYPE: nucleic acid
            (C) STRANDEDNESS: single
            (D) TOPOLOGY: linear (xi) SEQUENCE DESCRIPTION: SEQ ID NO:26:

TCCGCTCTGG ATGCCAGGGT GATTCTGGGG GACCCCTCCA CTGCATGGTG AACGGTCAGT      60

ATGCTGTCGA CGGAGTGACC AGCTTTGTGT CCAGCATGGG CTGTAATGTC GCCAGGAAGC     120

CCACCGTCTT CACCAGACTC TCTGCTTACA TTTCC                                155

(2) INFORMATION FOR SEQ ID NO:27:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (xi) SEQUENCE DESCRIPTION: SEQ ID NO:27:

AGCCTTGGGC TCCATCCCTA ATACTGCAAC AGGAGCAGGG GAATGCTGCT GGTGTCTTGG      60

TATCTGGGGC AAAGGTGGGG GG                                              82

(2) INFORMATION FOR SEQ ID NO:28:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:28:

GTGGGGGGTT AATGAAAAGC AACTCAGACT ACTGAATCAG ATACAGAAAG GCAAATAAAA      60

ATCAATGTGT TA                                                         72

(2) INFORMATION FOR SEQ ID NO:29:

(i) SEQUENCE CHARACTERISTICS:
            (A) LENGTH: 112 base pairs
            (B) TYPE: nucleic acid
            (C) STRANDEDNESS: single
            (D) TOPOLOGY: linear (xi) SEQUENCE DESCRIPTION: SEQ ID NO:29:

GGGGCAGGGG ATCTGCTCAG CTCTATGTTT GAGTTCAGTG AGAAGCTGAA TGCCCTCCAG      60

CTCAGTGATG AGGAAATGAG CTTGTTCACA GCAGTTGTTC TGGTATCTGC AG             112

(2) INFORMATION FOR SEQ ID NO:30:

(i) SEQUENCE CHARACTERISTICS:
            (A) LENGTH: 112 base pairs (B) TYPE: nucleic acid
            (C) STRANDEDNESS: single
            (D) TOPOLOGY: linear (xi) SEQUENCE DESCRIPTION: SEQ ID NO:30:

GGAGCAGGGG ATCTGCTCAG CTCTATGTTT GAGTTCAGTG AGAAGCTGAA TGCCCTCCAG      60

CTCAGTGATG AGGAAATGAG CTTGTTCACA GCAGTTGTTC TGGTATCTGC AG             112

(2) INFORMATION FOR SEQ ID NO:31:

(i) SEQUENCE CHARACTERISTICS:
            (A) LENGTH: 119 base pairs
            (B) TYPE: nucleic acid
            (C) STRANDEDNESS: single
            (D) TOPOLOGY: linear (xi) SEQUENCE DESCRIPTION: SEQ ID NO:31:

GATCGATCTG GAATTGAAAA TGTCAACTCA GTGGAGGCTT TGCAGGAAAC ACTCATCCGT      60

GCACTAAGGA CCTTAATAAT GAAAAACCAT CCAAATGAGG CCTCCATTTT TACAAAATT     119

(2) INFORMATION FOR SEQ ID NO:32:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (xi) SEQUENCE DESCRIPTION: SEQ ID NO:32:

AAAAACCATC CAAATGAGGC CTCCATTTTT ACAAAATTAC TTCTAAAGTT GCCAGATCTT      60

CGATCTTTAA ACAACATGCA CTC                                             83

(2) INFORMATION FOR SEQ ID NO:33:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (xi) SEQUENCE DESCRIPTION: SEQ ID NO:33:

GGTAAGAAGT ACAGTGTGGA TGACCTGCAC TCAATGGG                              38

(2) INFORMATION FOR SEQ ID NO:34:

(i) SEQUENCE CHARACTERISTICS:
            (A) LENGTH: 457 base pairs
            (B) TYPE: nucleic acid
            (C) STRANDEDNESS: single
            (D) TOPOLOGY: unknown (xi) SEQUENCE DESCRIPTION: SEQ ID NO:34:

CGCTGTCTCG GGAGGTCTGA AGACATGAAG CTGCTTCAGG TTCTCCTTGT TTTGCTGTTT      60

GTGGCACTTG CAGATGGTGC ACAGCCCAAA AGATGTTTTA GCAACGTAGA AGGCTACTGT     120

AGGAAGAAAT GCAGATTAGT GGAGATATCT GAGATGGGAT GCCTGCATGG GAAATACTGT     180

TGTGTTAATG AGCTGGAGAA CAAAAAGCAC AAGGAGCACT CAGTCGTTGA GGAGACAGTC     240

AAACTCCAAG ACAAGTCAAA AGTACAACAC TATATGATCC TGCCCACGGT CACATACTAC     300

ACCATCACTA TCTGAATGAA CCACTTGTTC ACGAAGGCCG TTGTCCCCTG CAGCCCCATG     360

GAATCCAGTG GGCTGCTTCT GTCCTGTCTC TTTCCTTCTG TGAAACTTGA GTCTGCACAC     420

AATAAAGTTC GACCCTTTTG GCTGAAAAAA AAAAAA                              457

(2) INFORMATION FOR SEQ ID NO:35:

(i) SEQUENCE CHARACTERISTICS:
        (A) LENGTH: 96 amino acids
        (B) TYPE: amino acid
        (C) STRANDEDNESS: single
        (D) TOPOLOGY: unknown (xi) SEQUENCE DESCRIPTION: SEQ ID NO:35:

```
Met Lys Leu Leu Gln Val Leu Leu Val Leu Leu Phe Val Ala Leu Ala
1               5                   10                  15

Asp Gly Ala Gln Pro Lys Arg Cys Phe Ser Asn Val Glu Gly Tyr Cys
            20                  25                  30

Arg Leu Leu Cys Arg Leu Leu Glu Ile Ser Glu Met Gly Cys Leu His
        35                  40                  45

Gly Lys Tyr Cys Cys Val Asn Glu Leu Glu Asn Lys Lys His Lys Glu
    50                  55                  60

His Ser Val Val Glu Glu Thr Val Lys Leu Gln Asp Lys Ser Lys Val
65                  70                  75                  80

Glu Asp Tyr Met Ile Leu Pro Thr Val Thr Tyr Thr Ile Ser Ile
                85                  90                  95
```

(2) INFORMATION FOR SEQ ID NO:36:

(i) SEQUENCE CHARACTERISTICS:
        (A) LENGTH: 1205 base pairs
        (B) TYPE: nucleic acid
        (C) STRANDEDNESS: single
        (D) TOPOLOGY: linear (xi) SEQUENCE DESCRIPTION: SEQ ID NO:36:

```
ATGGTTGGTT TCAAGGCCAC AGATGTGCCC CAACAGCCA CTGTGAAGTT CCTGGGGGCT      60
GGGACAGCTG CCTGCATTGC AGATCTCATC ACTTTCCCTC TGGATACCGC CAAGGTCCGG    120
CTGCAGATCC AAGGGGAGAG TCAAGGGCTA GTGCGCACCG CAGCCAGCGC CCAGTACCGT    180
GGCGTTCTGG GTACCATCCT AACCATGGTG CGCACTGAGG GTCCACGCAG CCTCTACAAT    240
GGGCTGGTCG CCGGCCTGCA GCGCCAGATG AGCCTTGCCT CCGTCCGCAT TGGCCTCTAC    300
GACTCTGTCA AACAGTTCTA CACCAAGGGC TCAGAGCATG GAGGCATCGG GAGCCGCCTC    360
CTGGCAGGTA GCACCACAGG TGCCCTGGCC GTGGTTGTAG CCCAGCCTAC AGATGTGGTA    420
AAGGTCCGCT TCCAGGCTCC AGGCCGGGCT GGTGGTGGTC GGAGATACAG AGCACTGTCG    480
AGCTACAAGA ACATCACGAG AGGAGGGATC CGGGGCCTCT GGAAGGGACT CTCCCAATGT    540
GCCCGTAATG CCATTGTCAA CTGTGCTGAG CTGGTGACCT ATGACCTCAT CAAAGATACT    600
CTCCTGAGCC ACCTCATGAC AGATGACCTC CCTTGCCACT TCACTTCTGC CTTCGGGGCG    660
GGCTTCTGCA CCACCGTCAT CGCCTCCCCT GTGGATGTGG TCAAGACGAG ATACATGACT    720
CTGCTGGGCC AGTACCACAG CGCAGGTCAC TGTGCCCTTA CATGCTCGGA GGAGGGACCC    780
GCGCTCTTCA ACCAGGGGGT TATGCCTTCC TTTCTCCGCT GGGATCCTG GAACGTAGTG    840
ATGTTTGTCA CCTATGAGCA GCTCCAAAGA GCCCTAATGG CTGCCTACCA ATCTCGGGAG    900
GCACCTTTCT GAGCCTCTCC ATGCTGACCT GGACCCTGCT TCCAGCCCT GCCCTGTCTT    960
TTTCTTCATC CTCTGCCCAG TCCCATTCTC TTCCCATTTC CTGCACCCCG ATTTACTTCC   1020
CACCTCACCT CCCTGTGCCT CTGTACTGAT GACTCACAGT GAGGAGGCCT GACACCAGAC   1080
CCTGAGCCCT CAGCCCTTTC TACAGCTAAG CCCACATCTT CATCTTCATC CCCAGCCCAG   1140
```

```
CCCAGCCCAG CTCAGCCAGC CTTCACCCAT AAAGCAAGCT CAATGTTAAA AAAAAAAAAA    1200

AAAAA                                                                1205
```

(2) INFORMATION FOR SEQ ID NO:37:

(i) SEQUENCE CHARACTERISTICS:
        (A) LENGTH: 303 amino acids
        (B) TYPE: amino acid
        (C) STRANDEDNESS: single
        (D) TOPOLOGY: unknown (xi) SEQUENCE DESCRIPTION: SEQ ID NO:37:

```
Met Val Gly Phe Lys Ala Thr Asp Val Pro Pro Thr Ala Thr Val Lys
1               5                  10                  15

Phe Leu Gly Ala Gly Thr Ala Ala Cys Ile Ala Asp Leu Ile Thr Phe
            20                  25                  30

Pro Leu Asp Thr Ala Lys Val Arg Leu Gln Ile Gln Gly Glu Ser Gln
        35                  40                  45

Gly Leu Val Arg Thr Ala Ala Ser Ala Gln Tyr Arg Gly Val Leu Gly
    50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Glu Met Ser Leu Ala Ser Val Arg
                85                  90                  95

Ile Gly Leu Tyr Asp Ser Val Lys Gln Phe Tyr Thr Lys Gly Ser Glu
            100                 105                 110

His Gly Gly Ile Gly Ser Arg Leu Leu Ala Gly Ser Thr Thr Gly Ala
        115                 120                 125

Leu Ala Val Val Val Ala Gln Pro Thr Asp Val Val Lys Val Arg Phe
    130                 135                 140

Gln Ala Pro Gly Arg Ala Gly Gly Arg Arg Tyr Arg Ala Leu Ser
145                 150                 155                 160

Ser Tyr Lys Asn Ile Thr Arg Gly Gly Ile Arg Gly Leu Trp Lys Gly
                165                 170                 175

Leu Ser Gln Cys Ala Arg Asn Ala Ile Val Asn Cys Ala Glu Leu Val
            180                 185                 190

Thr Tyr Asp Leu Ile Lys Asp Thr Leu Leu Ser His Leu Met Thr Asp
        195                 200                 205

Asp Leu Pro Cys His Phe Thr Ser Ala Phe Gly Ala Gly Phe Cys Thr
    210                 215                 220

Thr Val Ile Ala Ser Pro Val Asp Val Val Lys Thr Arg Tyr Met Thr
225                 230                 235                 240

Leu Leu Gly Gln Tyr His Ser Ala Gly His Cys Ala Leu Thr Cys Ser
                245                 250                 255

Glu Glu Gly Pro Ala Leu Phe Asn Gln Gly Val Met Pro Ser Phe Leu
            260                 265                 270

Arg Leu Gly Ser Trp Asn Val Val Met Phe Val Thr Tyr Glu Gln Leu
        275                 280                 285

Gln Arg Ala Leu Met Ala Ala Tyr Gln Ser Arg Glu Ala Pro Phe
    290                 295                 300
```

(2) INFORMATION FOR SEQ ID NO:38:

(i) SEQUENCE CHARACTERISTICS:
        (A) LENGTH: 1596 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:38:

| | | | | | |
|---|---|---|---|---|---|
| CCTCCGCCAG | CCGACAGACA | CAGCCGCACG | CACTGCCGTG | TTCTCCCTGC | GGCTCGGACA | 60 |
| CATAGTATGA | CCATTAGGTG | TTTCGTCTCC | CACCCATTTT | CTATGGAAAA | CCAAGGGGAT | 120 |
| CGGGCCATGA | TAGCCACTGG | CAGCTTTGAA | GAACGGGACA | CCTTTAGAGA | AGCTTGATCT | 180 |
| TGGAGGCCTC | ACCGTGAGAC | CTTACAAGGC | CGGATTCCGG | CAGAGTTCCT | CTATCTCGTC | 240 |
| TTGTTGCTGA | TTAAAGGTGC | CCCTGTCTCC | AGTTTTTCTC | CATCTCCTGG | GACGTAGCAG | 300 |
| GAAATCAGCA | TCATGGTTGG | GTTCAAGGCC | ACAGATGTGC | CCCCTACTGC | CACTGTGAAG | 360 |
| TTTCTTGGGG | CTGGCACAGC | TGCCTGCATC | GCAGATCTCA | TCACCTTTCC | TCTGGATACT | 420 |
| GCTAAAGTCC | GGTTACAGAT | CCAAGGAGAA | AGTCAGGGGC | CAGTGCGCGC | TACAGTCAGC | 480 |
| GCCCAGTACC | GCGGTGTGAT | GGGCACCATT | CTGACCATGG | TGCGTACTGA | GGGCCCCCGA | 540 |
| AGCCTCTACA | ATGGGCTGGT | TGCCGGCCTG | CAGCGCCAAA | TGAGCTTTGC | CTCTGTCCGC | 600 |
| ATCGGCCTGT | ATGATTCTGT | CAAACAGTTC | TACACCAAGG | GCTCTGAGCA | TGCCAGCATT | 660 |
| GGGAGCCGCC | TCCTAGCAGG | CAGCACCACA | GGTGCCCTGG | CTGTGGCTGT | GGCCCAGCCC | 720 |
| ACGGATGTGG | TAAAGGTCCG | ATTCCAAGCT | CAGGCCCGGG | CTGGAGGTGG | TCGGAGATAC | 780 |
| CAAAGCACCG | TCAATGCCTA | CAAGACCATT | GCCCGAGAGG | AAGGGTTCCG | GGGCCTCTGG | 840 |
| AAAGGGACCT | CTCCCAATGT | TGCTCGTAAT | GCCATTGTCA | ACTGTGCTGA | GCTGGTGACC | 900 |
| TATGACCTCA | TCAAGGATGC | CCTCCTGAAA | GCCAACCTCA | TGACAGATGA | CCTCCCTTGC | 960 |
| CACTTCACTT | CTGCCTTTGG | GGCAGGCTTC | TGCACCACTG | TCATCGCCTC | CCCTGTAGAC | 1020 |
| GTGGTCAAGA | CGAGATACAT | GAACTCTGCC | CTGGGCCAGT | ACAGTAGCGC | TGGCCACTGT | 1080 |
| GCCCTTACCA | TGCTCCAGAA | GGAGGGGCCC | CGAGCCTTCT | ACAAAGGGTT | CATGCCCTCC | 1140 |
| TTTCTCCGCT | TGGGTTCCTG | GAACGTGGTG | ATGTTCGTCA | CCTATGAGCA | GCTGAAACGA | 1200 |
| GCCCTCATGG | CTGCCTGCAC | TTCCCGAGAG | GCTCCCTTCT | GAGCCTCTCC | TGCTGCTGAC | 1260 |
| CTGATCACCT | CTGGCTTTGT | CTCTAGCCGG | GCCATGCTTT | CCTTTTCTTC | CTTCTTTCTC | 1320 |
| TTCCCTCCTT | CCCTTCTCTC | CTTCCCTCTT | TCCCCACCTC | TTCCTTCCGC | TCCTTTACCT | 1380 |
| ACCACCTTCC | CTCTTTCTAC | ATTCTCATCT | ACTCATTGTC | TCAGTGCTGG | TGGAGTTGAC | 1440 |
| ATTTGACAGT | GTGGGAGGCC | TCGTACCAGC | CAGGATCCCA | AGCGTCCCGT | CCCTTGGAAA | 1500 |
| GTTCAGCCAG | AATCTTCGTC | CTGCCCCCGA | CAGCCCAGCC | TAGCCCACTT | GTCATCCATA | 1560 |
| AAGCAAGCTC | AACCTTGAAA | AAAAAAAAAA | AAAAAA | | | 1596 |

(2) INFORMATION FOR SEQ ID NO:39:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:39:

AAAGGATGGA ATACCAAGGT CTTTTTATTC CTCGTGAAAA AAAAAAAA                   48

(2) INFORMATION FOR SEQ ID NO:40:

(i) SEQUENCE CHARACTERISTICS:
        (A) LENGTH: 84 base pairs
        (B) TYPE: nucleic acid

```
        (C) STRANDEDNESS: single
        (D) TOPOLOGY: linear (xi) SEQUENCE DESCRIPTION: SEQ ID NO:40:

AACCGTCGNT GGCACTGGAG CAGTGGCTCC CTATTTCTCT TCAAGTCATG GGCCACTGGA      60

GCTCCAAGCA CTGCCAACCG GGTT                                            84

(2) INFORMATION FOR SEQ ID NO:41:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:41:

AACGCCTATG GTTCCTACTG TTATTATCTA ATTGAAGACC GCTTGACCTG GGGGGAGGCT      60

GATCT                                                                 65

(2) INFORMATION FOR SEQ ID NO:42:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:42:

AGGATACAAA AAATGGGAGG ACGAAAACTG TGAGGCACAG TACTCCTTGG TCTTGAAGTT      60

CAGAGGCTAA                                                            70

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:43:

CCGACCAATG CATTGACAAC TGAATGGGTK GT                                   32

(2) INFORMATION FOR SEQ ID NO:44:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO:44:

AGCCTTGGGC TCCATCCCTA ATACTGCAAC AGGAGCAGGG GAATGCTGCT GGTGTCTTGG      60

TATCTGGGGC AAAGGTGGGG GG                                              82

(2) INFORMATION FOR SEQ ID NO:45:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:45:

GGGGGGGGTT CATGAAAAGC AACTCAGACT ACTGAATCAG ATACAGAAAG GCAAATAAAA      60
```

```
ATCAATGTGT TA                                                         72

(2) INFORMATION FOR SEQ ID NO:46:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (xi) SEQUENCE DESCRIPTION: SEQ ID NO:46:

GATCGATCTG GAATTGAAAA TGTCAACTCA GTGGAGGCTT TGCAGGAAAC ACTCATCCGT      60

GCACTAAGGA CCTTAATAAT GRAAAAACCA TCCAAATGAG GCCTCCATTT TTACAAAAT     119

(2) INFORMATION FOR SEQ ID NO:47:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO:47:

AAAAACCATC CAAATGAGGC CTCCATTTTT ACAAAATTAC TTCTAAAGTT GCCAGRTCTT      60

CGATCTTTAA ACAACATGCA CTC                                             83

(2) INFORMATION FOR SEQ ID NO:48:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:48:

GGTAAGAAGT ACAGTGTGGA TGACCTGCAC TCAATGGG                              38

(2) INFORMATION FOR SEQ ID NO:49:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (xi) SEQUENCE DESCRIPTION: SEQ ID NO:49:

GATCCCTGGC CAGAAGTACA AAGACACTAA CCTGCTAATA CTCTTTAAGG AAGATTACTT      60

TGCAAAAAAA AATGAAGAAA GAAAGCAGAG CAAAGTGGAA GCTAAATTAA AAGCTAAACA     120

AGAGCATGAA GGAAGACACA AGCCAGGAAG TACTGAAACC                           160

(2) INFORMATION FOR SEQ ID NO:50:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (xi) SEQUENCE DESCRIPTION: SEQ ID NO:50:

GATCCCTGGC CAGAAGTACA AAGACACTAA CCTGCTAATA CTCTTTAAGG AAGATTACTT      60

TGCAAAAAAA AATGAAGAAA GAAAGCAGAG CAAAGTGGAA GCTAAATTAA AAGCTAAACA     120

AGAGCATGAA GGAAGACACA AGCCAGGAAG TACTGAAACC                           160
```

(2) INFORMATION FOR SEQ ID NO:51:

(i) SEQUENCE CHARACTERISTICS:
        (A) LENGTH: 309 amino acids
        (B) TYPE: amino acid
        (C) STRANDEDNESS: single
        (D) TOPOLOGY: unknown (xi) SEQUENCE DESCRIPTION: SEQ ID NO:51:

```
Met Val Gly Phe Lys Ala Thr Asp Val Pro Thr Ala Thr Val Lys
1               5                   10                  15

Phe Leu Gly Ala Gly Thr Ala Ala Cys Ile Ala Asp Leu Ile Thr Phe
                20                  25                  30

Pro Leu Asp Thr Ala Lys Val Arg Leu Gln Ile Gln Gly Glu Ser Gln
                35                  40                  45

Gly Pro Val Arg Ala Thr Val Ser Ala Gln Tyr Arg Gly Val Met Gly
            50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
                100                 105                 110

His Ala Ser Ile Gly Ser Arg Leu Leu Ala Gly Ser Thr Thr Gly Ala
                115                 120                 125

Leu Ala Val Ala Val Ala Gln Pro Thr Asp Val Val Lys Val Arg Phe
130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
                180                 185                 190

Glu Leu Val Thr Tyr Asp Leu Ile Lys Asp Ala Leu Leu Lys Ala Asn
                195                 200                 205

Leu Met Thr Asp Asp Leu Pro Cys His Phe Thr Ser Ala Phe Gly Ala
                210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
                260                 265                 270

Phe Met Pro Ser Phe Leu Arg Leu Gly Ser Trp Asn Val Val Met Phe
                275                 280                 285

Val Thr Tyr Glu Gln Leu Lys Arg Ala Leu Met Ala Ala Cys Thr Ser
                290                 295                 300

Arg Glu Ala Pro Phe
305
```

(2) INFORMATION FOR SEQ ID NO:52:

(i) SEQUENCE CHARACTERISTICS:
        (A) LENGTH: 73 base pairs
        (B) TYPE: nucleic acid
        (C) STRANDEDNESS: single (D) TOPOLOGY: linear (xi) SEQUENCE DESCRIPTION: SEQ ID NO:52:

```
AGGGTCAGTG GTCTCCAGTC TTCTCCCAGT TTGGGCTTAT TGATGTCCAA TAAACAAGTT      60

CTGTGTCTGC AAA                                                         73
```

(2) INFORMATION FOR SEQ ID NO:53:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:53:

```
AGGGGCAGGG GCTCCATTCT TCTCCCCGGT TTGGTCTGAT TGATGTCCAA TAAACAACTT      60

CTGTATCTTC AAA                                                         73
```

(2) INFORMATION FOR SEQ ID NO:54:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:54:

```
CCCTACCAAC TCTGTGCAGT GGTTCGCTAA AGGGTCAGTG GTCTCCAGTC TTCTCCCAGT      60

TTGGG                                                                  65
```

(2) INFORMATION FOR SEQ ID NO:55:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:55:

```
CCTTACCAAC TCTGTGCAGT GGCTCGCTAG CAGGGGCAGG GGCTCCATTC TTCTCCCCGG      60

TTTGG                                                                  65
```

(2) INFORMATION FOR SEQ ID NO:56:

(i) SEQUENCE CHARACTERISTICS:
        (A) LENGTH: 307 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

```
Met Val Asn Pro Thr Thr Ser Glu Val Gln Pro Thr Met Gly Val Lys
 1               5                  10                  15

Ile Phe Ser Ala Gly Val Ser Ala Cys Leu Ala Asp Ile Ile Thr Phe
             20                  25                  30

Pro Leu Asp Thr Ala Lys Val Arg Leu Gln Ile Gln Gly Glu Gly Gln
         35                  40                  45

Ala Ser Ser Thr Ile Arg Tyr Lys Gly Val Leu Gly Thr Ile Thr Thr
     50                  55                  60

Leu Ala Lys Thr Glu Gly Leu Pro Lys Leu Tyr Ser Gly Leu Pro Ala
```

```
              65                  70                  75                  80
Gly Ile Gln Arg Gln Ile Ser Phe Ala Ser Leu Arg Ile Gly Leu Tyr
                85                  90                  95
Asp Ser Val Gln Glu Tyr Phe Ser Ser Gly Arg Glu Thr Pro Ala Ser
               100                 105                 110
Leu Gly Asn Lys Ile Ser Ala Gly Leu Met Thr Gly Val Ala Val
           115                 120                 125
Phe Ile Gly Gln Pro Thr Glu Val Val Lys Val Arg Met Gln Ala Gln
           130                 135                 140
Ser His Leu His Gly Ile Lys Pro Arg Tyr Thr Gly Thr Tyr Asn Ala
145                 150                 155                 160
Tyr Arg Val Ile Ala Thr Thr Glu Ser Leu Ser Thr Leu Trp Lys Gly
               165                 170                 175
Thr Thr Pro Asn Leu Met Arg Asn Val Ile Ile Asn Cys Thr Glu Leu
               180                 185                 190
Val Thr Tyr Asp Leu Met Lys Gly Ala Leu Val Asn Asn Lys Ile Leu
           195                 200                 205
Ala Asp Asp Val Pro Cys His Leu Leu Ser Ala Leu Val Ala Gly Phe
       210                 215                 220
Cys Thr Thr Leu Leu Ala Ser Pro Val Asp Val Val Lys Thr Arg Phe
225                 230                 235                 240
Ile Asn Ser Leu Pro Gly Gln Tyr Pro Ser Val Pro Ser Cys Ala Met
               245                 250                 255
Ser Met Tyr Thr Lys Glu Gly Pro Thr Ala Phe Lys Gly Phe Val
               260                 265                 270
Ala Ser Phe Leu Arg Leu Gly Ser Trp Asn Val Ile Met Phe Val Cys
           275                 280                 285
Phe Glu Gln Leu Lys Lys Glu Leu Met Lys Ser Arg Gln Thr Val Asp
       290                 295                 300
Cys Thr Thr
305

(2) INFORMATION FOR SEQ ID NO:57:

(i) SEQUENCE CHARACTERISTICS:
        (A) LENGTH: 1308 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:57:

GGAATTCGGC ACGAGGAACT AGTCTCGAGT AGCTCTGTGT GTGTAGACAC TCCCTAAGCC      60

ACCCGAGGGC TGCCTCTGTG TGGTGGGGAG GTAGGAGAGG GGAAGAGGGT TGCTATTCTC     120

ATTTTATACT TTTCCCACGG CTTCCAACTT TATGCCAATA ACTCACAATT AAACAGGTCT     180

CAGAACTAAG GGAGCTTTCA ACACTTGGGC TAACTCAAGT GCAGTGAGCG AACGGGTTCT     240

CCAAACCTGC TGGGTCCTGG CTACCTATGT CACACAGATG AGTGAGTCCA CCTGCCTTCC     300

ATTCTCTGAG CTTGTGGTCA CAGCAGGAGT CTTCCAGGGC ACTGCCTTGG STTGGAAATG     360

TAAGTCCGTC CGGAAATAGT ATCCCCATCA GCTCTCTGGT GTTTGTGAGC TCTAGCATGC     420

CATCCAGGTT CCAAGGAGGA GAGTCACGAA GGTCCCAGAG CCGCAAGGTG CACAGAGCAC     480

CCTATAAACC CTGCAGTCCT CTTTGAGTCA TGGGAGGAC TGTGGATCCC CTTCTTTGAG      540

TCTAAAGAGG CTCAGGAATC CATATTCTCC ACAAGGTCCA GGTGGAAGT GCATGCATGA      600
```

```
AATCAGACTC CAAAAAATGA ACCACAAGTC ACAGGAGAGA GAGAGAACTA GTCTCGAGCT    660

CGTGCCGAAT TCGGCACGAG GTGTAGCTCA GGTAGCCCAG GGAGCAATCA AGCTCTGCTT    720

CCTGCTGCGC AGCTGTGGCT CGCTCCTGCC CGAACTGAGT CTCGCCGAGA GGACAGAGTT    780

TGCTCACAAG ATCTGGGACA AACTTCAGCA GTTAGGTGTC GTATATGATG TCAGTCATTA    840

CAATGCTTTA CTTAAAGTAT ATCTTCAAAA TGAATACAAA TTTTCACCTA CTGACTTCCT    900

GGCAAAGATG GAGGGAGCAA ACATCCAACC AAATCGAGTA ACATACCAGA GGCTGATAGC    960

TGCCTACTGT AATGTTGGGG ACATTGAAGG TGCCAGCAAG ATCCTTGGAT TTATGAAAAC   1020

GAAAGACCTT CCGATCACAG AGGGCGTGTT CAGTGCTCTC GTCACAGGGC ATGCGAGAGC   1080

TGGGGATATG GAAAATGCAG AAAATATTCT CACAGTGATG AAACAGGCCG GCATTGAGCC   1140

TGGCCCAGAC ACGTATCTGG CCTTGTTGAA TGCACATGCT GAGAGGGGTG ACATTGGCCA   1200

GGTTAGGCAG ATTCTGGAGA AAGTGGAGAA GTCAGACCAT TACTTCATGG ACCGCGACTT   1260

CTTGCAGGTT ATTTTTAGCT TCAGTAAGGC TGGCTACCCT CACTCGAG               1308

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

CATGATGCTG ATTTCCTG                                                   18

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

CATGATGCTG ATTTCCTGCT ACGT                                            24

(2) INFORMATION FOR SEQ ID NO:60:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:60:

CATGATGCTG ATTTCCTGCT ACGTCCCAGG AGA                                  33

(2) INFORMATION FOR SEQ ID NO:61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear
```

-continued

```
    (ii) MOLECULE TYPE: DNA (xi) SEQUENCE DESCRIPTION: SEQ ID NO:61:

CAACCATGAT GCTGATTTCC TGCTACGTCC CAG                              33

(2) INFORMATION FOR SEQ ID NO:62:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:62:

CAACCATGAT GCTGATTTCC TGCTACG                                     27

(2) INFORMATION FOR SEQ ID NO:63:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:63:

CAACCATGAT GCTGATTTCC TGCTACG                                     27

(2) INFORMATION FOR SEQ ID NO:64:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:64:

CAACCATGAT GCTGATT                                                17
```